US011519011B2

(12) United States Patent
Yuan et al.

(10) Patent No.: US 11,519,011 B2
(45) Date of Patent: Dec. 6, 2022

(54) CONVERSION OF LIGNIN INTO BIOPLASTICS AND LIPID FUELS

(71) Applicant: The Texas A&M University System, College Station, TX (US)

(72) Inventors: Shuhua Yuan, College Station, TX (US); Shangxian Xie, College Station, TX (US); Xin Wang, College Station, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 15/561,939

(22) PCT Filed: Mar. 28, 2016

(86) PCT No.: PCT/US2016/024579
§ 371 (c)(1),
(2) Date: Sep. 26, 2017

(87) PCT Pub. No.: WO2016/154631
PCT Pub. Date: Sep. 29, 2016

(65) Prior Publication Data
US 2018/0216141 A1    Aug. 2, 2018

Related U.S. Application Data
(60) Provisional application No. 62/138,916, filed on Mar. 26, 2015.

(51) Int. Cl.
*C12P 19/02* (2006.01)
*C12N 1/21* (2006.01)
*C12N 9/02* (2006.01)
*C12N 9/08* (2006.01)
*C12P 7/14* (2006.01)
*C12N 9/04* (2006.01)
*C12P 7/6463* (2022.01)
*C12P 7/649* (2022.01)
*C12P 7/06* (2006.01)

(52) U.S. Cl.
CPC .............. *C12P 7/14* (2013.01); *C12N 9/0006* (2013.01); *C12N 9/0061* (2013.01); *C12N 9/0065* (2013.01); *C12P 7/065* (2013.01); *C12P 7/649* (2013.01); *C12P 7/6463* (2013.01); *Y02E 50/10* (2013.01)

(58) Field of Classification Search
None
See application file for complete search history.

(56) References Cited

U.S. PATENT DOCUMENTS

2013/0309730 A1* 11/2013 Leonetti .................. C12N 1/22
                                                        435/105
2017/0096558 A1*  4/2017 Slaghek .................. C08L 95/00

FOREIGN PATENT DOCUMENTS

EP            2468857 A1 *  6/2012  .............. C12P 21/02
WO    WO 2008/100251       8/2008
WO       2013055890 A1     4/2013

OTHER PUBLICATIONS

Kosa et al., "Direct and Multistep Conversion of Lignin to Biofuels", Dissertation, Georgia Institute of Technology, Dec. 2012 (Year: 2012).*
You et al., "Alternative Materials for Sustainable Transportation", Michigan Technological University, 2012, 133 pages (Year: 2012).*
Janusz et al., Int. J. Mol. Sci. 21:966, 2020 (Year: 2020).*
Ece et al., AMB Expr. 7:86, 2017 (Year: 2017).*
Xie et al., Adv. Sci. 6:1801980, 2019 (Year: 2019).*
Freudl, Microb. Cell Fact. 17:52, 2018 (Year: 2018).*
Kalscheuer et al., Appl. Microbiol. Biotechnol. 52:508-515, 1999 (Year: 1999).*
Yuan, S., "Synthetic Design Microorganisms for Lignin Fuels and Chemicals", DOE Bioenergy Technologies Office (BETO) 2015 Project Peer Review, Mar. 26, 2015 (Year: 2015).*
International Search Report and Written Opinion regarding International Application No. PCT/US2016/024579, dated Jun. 24, 2016.
Choi et al., "Secretory and extracellular production of recombinant proteins using *Escherichia coli*," *Appl. Microbiol. Biotechnol.* 64:625-635, 2004.
Gerischer, "Specific and Global Regulation of Genes Associated with the Degradation of Aromatic Compounds in Bacteria," *J. Mol. Microbiol. Biotechnol.* 4:111-121, 2002.
Pollegioni et al., "Lignin-degrading enzymes," *FEBS Journal* 282:1190-1213, 2015.
Solaiman et al., "Rapid Genetic Characterization of Poly(hydroxyalkanoate) Synthase and Its Applications," *Biomacromolecules* 6:532-537, 2005.
Ahmad et al., "Development of novel assays for lignin degradation: comparative analysis of bacterial and fungal lignin degraders," *Mol. BioSyst.* 6:815-821, 2010.
Aremu et al., "Production of Polyhydroxybutyrate (PHB) by Pseudomonas Putida Strain KT2440 on Cassava Hydrolysate Medium," *Res. J. Chem. Sci.* 1(4):67-73, 2011.
Brown et al., "Identification and Characterization of a Multifunctional Dye Peroxidase from a Lignin-Reactive Bacterium," *ACS Chem. Biol.* 7(12):2074-2081, 2012.
Brune, "Symbiotic digestion of lignocellulose in termite guts," *Nature Reviews—Microbiology* 12:169-180, 2014.

(Continued)

*Primary Examiner* — David Steadman
(74) *Attorney, Agent, or Firm* — Dentons US LLP

(57) ABSTRACT

The present invention provides methods and compositions for increasing lignin degradation to produce a biological product. Also provided are methods for increasing expression of laccase in a bacterial species to produce increased lignin degradation. Also provided are bacterial cells and commodities or commodity produces produced from such methods.

8 Claims, 44 Drawing Sheets
Specification includes a Sequence Listing.

(56) References Cited

OTHER PUBLICATIONS

Bugg et al., "Pathways for degradation of lignin in bacteria and fungi," *Nat. Prod. Rep.* 28:1883-1896, 2011.
Bugg et al., "The emerging role for bacteria in lignin degradation and bio-product formation," *Current Opinion in Biotechnology* 22:394-400, 2011.
Chen et al., "Lignin modification improves fermentable sugar yields for biofuel production," *Nature Biotechnology* 25(7):759-761, 2007.
Chen et al., "Preparation of lignin/glycerol-based bis(cyclic carbonate) for the synthesis of polyurethanes," *Green Chem.* 17:4546-4551, 2015.
Dammeyer et al., "Efficient production of soluble recombinant single chain Fv fragments by a *Pseudomonas putida* strain KT2440 cell factory," *Microbial Cell Factories* 10:11, 2011.
Doddapaneni et al., "A comparative genomic analysis of the oxidative enzymes potentially involved in lignin degradation by *Agaricus bisporus*," *Fungal Genetics and Biology* 55:22-31, 2013.
Du et al., "The promoting effect of byproducts from *Irpex lacteus* on subsequent enzymatic hydrolysis of bio-pretreated cornstalks," *Biotechnology for Biofuels* 4:37, 2011.
Dugar et al., "Relative potential of biosynthetic pathways for biofuels and bio-based products," *Nature Biotechnology* 29(12):1074-1078, 2011.
Eastwood et al., "The Plant Cell Wall-Decomposing Machinery Underlies the Functional Diversity of Forest Fungi," *Science* 333:762-765, 2011.
Floudas et al., "The Paleozoic Origin of Enzymatic Lignin Decomposition Reconstructed from 31 Fungal Genomes," *Science* 336:1715-1719, 2012.
GenBank Accession No. JSVW00000000, dated Dec. 14, 2016.
Henriksson et al., "Cellobiose dehydrogenase (cellobiose oxidase) from *Phanerochaete chrysosporium* as a wood-degrading enzyme. Studies on cellulose, xylan and synthetic lignin," *Applied Microbiology and Biotechnology* 42(5):790-796, 1995.
Hori et al., "Genomewide analysis of polysaccharides degrading enzymes in 11 white- and brown-rot Polyporales provides insight into mechanisms of wood decay," *Mycologia* 105-1412-1427, 2013.
Jensen et al., "An NADH:Quinone Oxidoreductase Active during Biodegradation by the Brown-Rot Basidiomycete *Gloeophyllum trabeum*," *Applied and Environmental Microbiology* 68(6):2699-2703, 2002.
Jimenez et al., "Genomic analysis of the aromatic catabolic pathways from Pseudomonas putida KT2440," *Environmental Microbiology* 4(12):824-841, 2002.
Kadla et al., "The Reactions of Peroxides with Lignin and Lignin Model Compounds." DOI: 10.1021/bk-2001-0785.ch006, 2001.
Kersten et al., "Extracellular oxidative systems of the lignin-degrading Basidiomycete *Phanerochaete chrysosporium*," *Fungal Genetics and Biology* 44:77-87, 2007.
Kinne et al., "Oxidative Cleavage of Diverse Ethers by an Extracellular Fungal Peroxygenase," *The Journal of Biological Chemistry* 284(43):29343-29349, 2009.
Kosa et al., "Lignin to lipid bioconversion by oleaginous Rhodococci," *Green Chem.* 15:2070-2074, 2013.
Kurosawa et al, "High-cell-density batch fermentation of *Rhodococcus opacus* PD630 using a high glucose concentration for triacylglycerol production," *Journal of Biotechnology* 147:212-218, 2010.
Liers et al., "Patterns of lignin degradation and oxidative enzyme secretion by different wood- and litter-colonizing basidiomycetes and ascomycetes grown on beech-wood," *FEMS Microbiol. Ecol.* 78:91-102, 2011.
Lu et al., "Function of the iron-binding chelator produced by *Coriolus versicolor* in lignin biodegradation," *Science in China Series C: Life Sciences* 51:214, 2008.
Lynd et al., "How biotech can transform biofuels," *Nature Biotechnology* 26(2):169-172, 2008.
Martinez et al., "Genome sequence of the lignocellulose degrading fungus *Phanerochaete chrysosporium* strain RP78," *Nature Biotechnology* 22(6):695-700, 2004.
Martinez et al., "Genome, transcriptome, and secretome analysis of wood decay fungus *Postia placenta* supports unique mechanisms of lignocellulose conversion," *PNAS* 106(6):1954-1959, 2009.
Masai et al., "Genetic and Biochemical Investigations on Bacterial Catabolic Pathways for Lignin-Derived Aromatic Compounds," *Biosci. Biotechnol. Biochem.* 71(1):1-15, 2007.
Munk et al., "Can laccases catalyze bond cleavage in lignin?," *Biotechnology Advances* 33:13-24, 2015.
Nikel et al., "Biotechnological domestication of pseudomonads using synthetic biology," *Nature Reviews—Microbiology* 12:368-379, 2014.
Nikodinovic-Runic et al., "Analysis of the *Pseudomonas putida* CA-3 proteome during growth on styrene under nitrogen-limiting and non-limiting conditions," *Microbiology* 155:3348-3361, 2009.
Peralta-Yahya et al., "Identification and microbial production of a terpene-based advanced biofuel," *Nature Communications* 2:483, 2011.
Peralta-Yahya et al., "Microbial engineering for the production of advanced biofuels," *Nature* 488:320-328, 2012.
Ragauskas et al., "Lignin Valorization: Improving Lignin Processing in the Biorefinery," *Science* 344:1246843, 2014.
Rohr et al., "A First Insight into *Pycnoporus sanguineus* BAFC 2126 Transcriptome," *PLOS ONE* 8(12):e81033, 2013.
Singh et al., "Investigation of wheat straw biodegradation by *Phanerochaete chrysosporium*," *Biomass and Bioenergy* 35:1030-1040, 2011.
Tomizawa et al., "Understanding the Limitations in the Biosynthesis of Polyhydroxyalkanoate (PHA) from Lignin Derivatives," *ACS Sustainable Chem. Eng.* 2:1106-1113, 2014.
Wei et al., "Genomic, Proteomic, and Biochemical Analyses of Oleaginous *Mucor circinelloides*: Evaluating Its Capability in Utilizing Cellulolytic Substrates for Lipid Production," *PLOS ONE* 8(9):e71068, 2013.
Wu et al., "Comparative genomics and functional analysis of niche-specific adaptation in *Pseudomonas putida*," *FEMS Microbiol. Rev.* 35:299-323, 2011.
Wymelenberg et al., "Comparative Transcriptome and Secretome Analysis of Wood Decay Fungi *Postia placenta* and *Phanerochaete chrysosporium*," *Applied and Environmental Microbiology* 76(11):3599-3610, 2010.
Wymelenberg et al., "Structure, Organization, and Transcriptional Regulation of a Family of Copper Radical Oxidase Genes in the Lignin-Degrading Basidiomycete Phanerochaete chrysosporium," *Applied and Environmental Microbiology* 72(7):4871-4877, 2006.
Xie et al., "Exploration of Natural Biomass Utilization Systems (NBUS) for advanced biofuel—from systems biology to synthetic design," *Current Opinion in Biotechnology* 27:195-203, 2014.
Yuan et al., "Plants to power: bioenergy to fuel the future," *Trends in Plant Science* 13(8):421-429, 2008.
Zeng et al., "Lignocellulosic biomass as a carbohydrate source for lipid production by *Mortierella isabellina*," *Bioresource Technology* 128:385-391, 2013.
Zhao et al., "Synergistic enzymatic and microbial lignin conversion," *Green Chem.* 18:1306-1312, 2016.
Partial European Search Report regarding Europe Application No. 16769843.0, dated Aug. 1, 2018, 13 pages.
Kudanga T et al., "Laccase applications in biofuels production: Current status and future prospects," Applied Microbiology and Biotechnology, 98(15): 6525-6542; Aug. 2014.
Matyas Kosa et al. "Lignin to lipid bioconversion by oleaginous Rhodococci," Green Chemistry, 15(8): 2070, Jan. 2013.
Williams, R. Christopher "Using Lignin as an Asphalt Antioxidant," Iowa State University—Digital Repository, May 2008, Retrieved from the Internet: URL:https://lib.dr.iastate.edu/cgi/viewcontent.cgi?referer=https://www.google.com/&httpsredir=1&article=1013&context—intrans_techtransfer [retrieved on Jul. 11, 2018].

\* cited by examiner

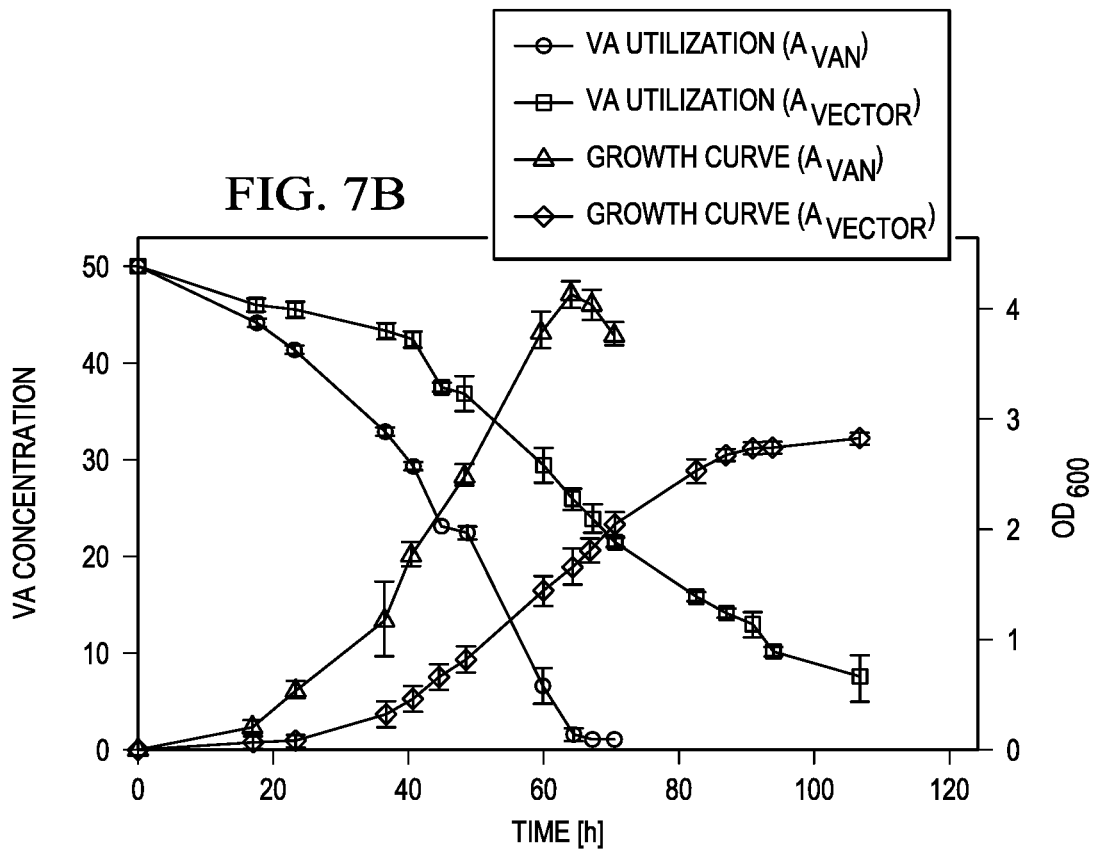
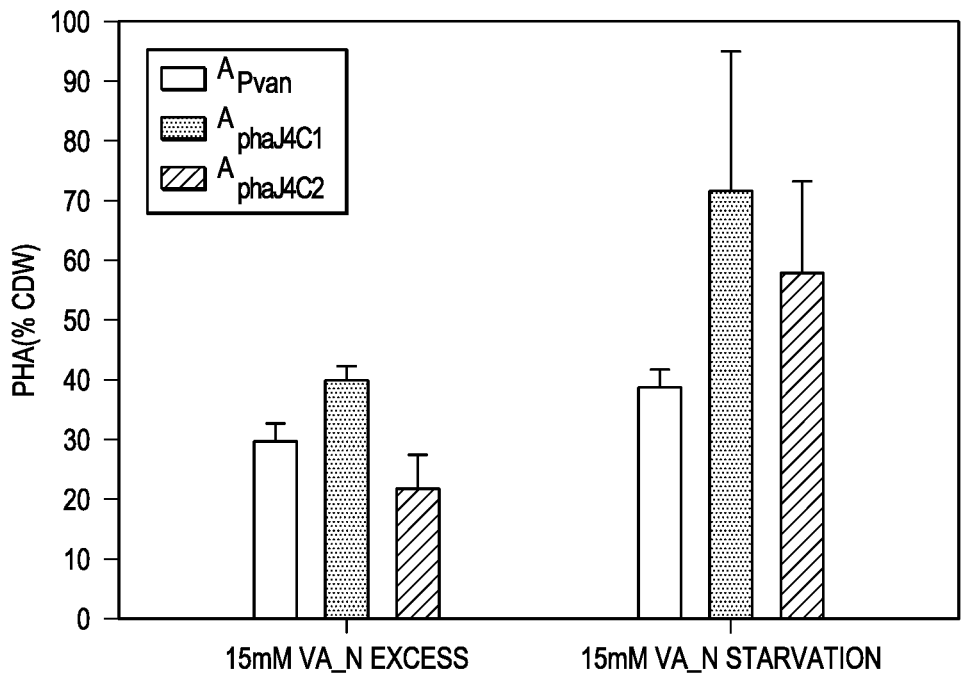

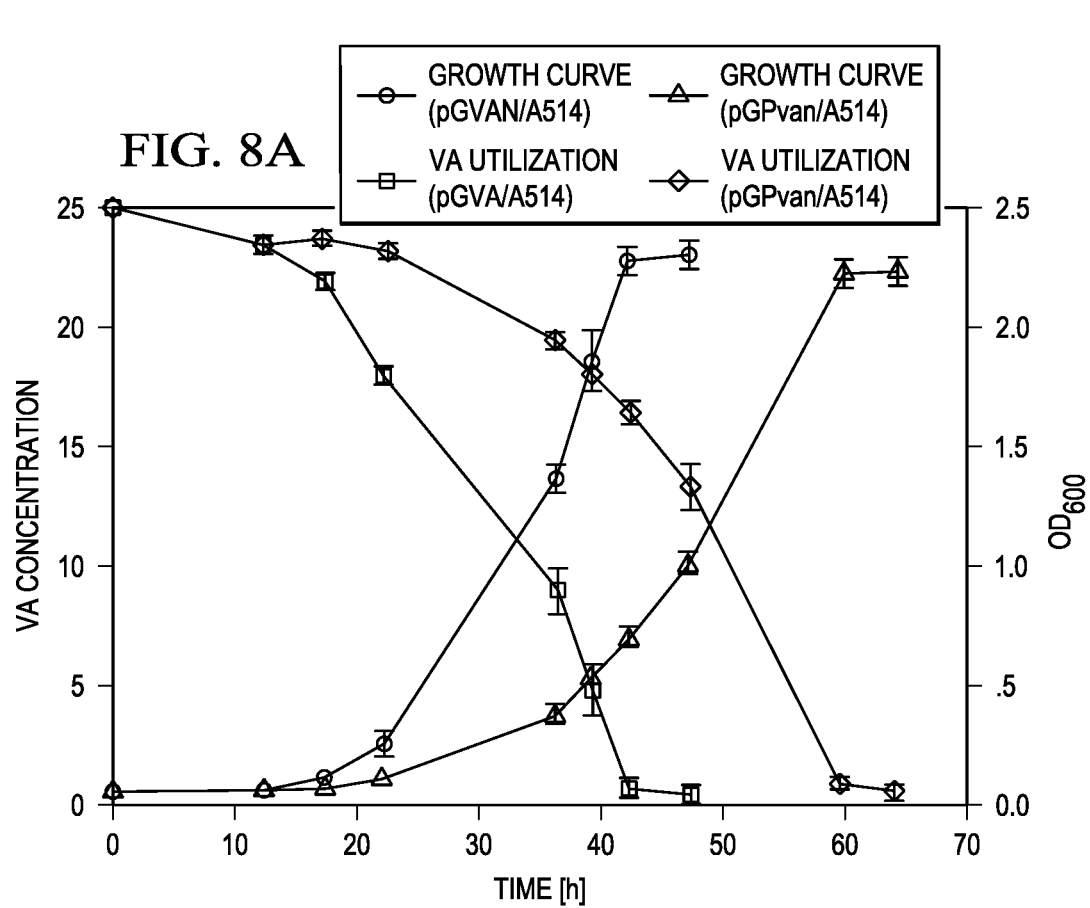

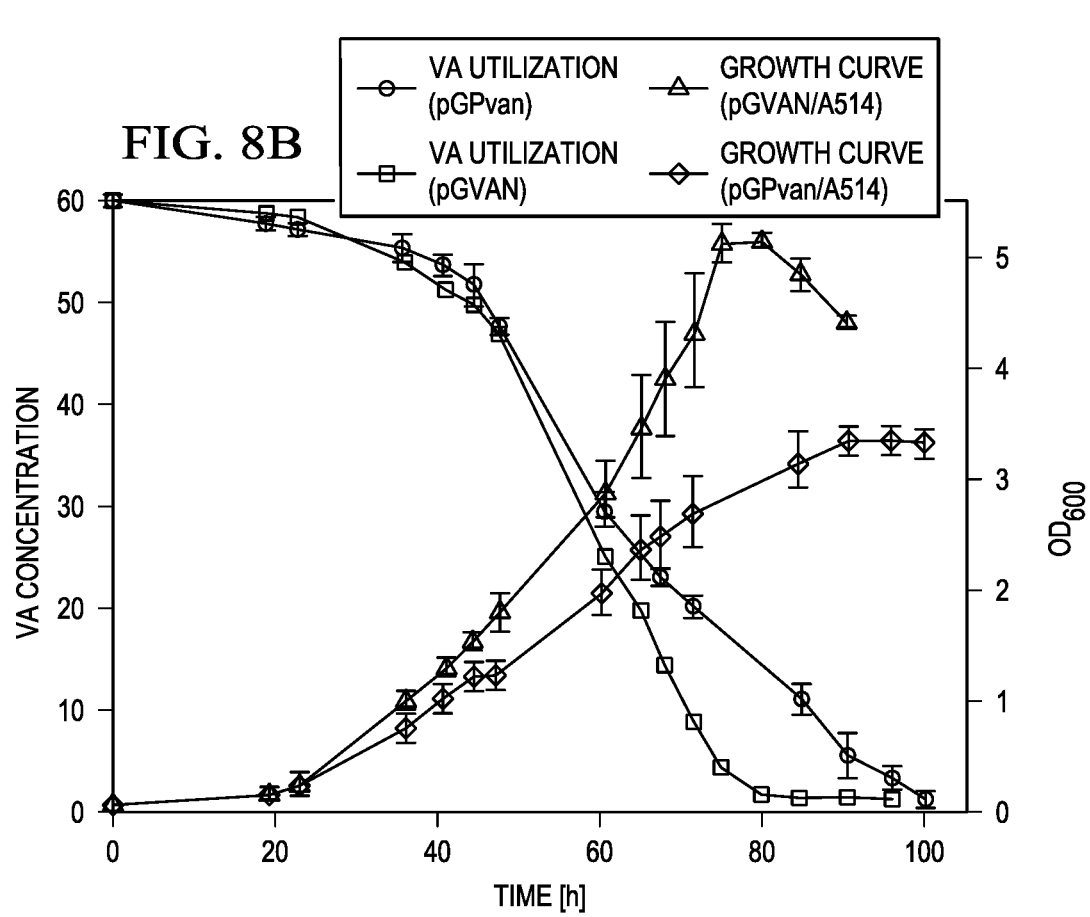

SEQUENCE LISTING

<160> NUMBER OF SEQ ID NOS: 35

<210> SEQ ID NO 1
<211> LENGTH: 120
<212> TYPE: DNA
<213> ORGANISM: Rhodococcus opacus

<400> SEQUENCE: 1

```
gtgattgtca cagcaacgaa gccgtcacat ggttggttac gaggcgtcgt ccggctgatg        60
gttgccgtgg tgatcctgcc gctggcgttc gtcctcgtcg gcggcggaac ggcctccgcc       120
```

<210> SEQ ID NO 2
<211> LENGTH: 400
<212> TYPE: DNA
<213> ORGANISM: Rhodococcus opacus

<400> SEQUENCE: 2

```
gctcgcgctc ggcggcggca tcgcccgttc cggtgcggcc gacggcacca ccaccgtcgc        60
gatcgccggg tggggttcgg gtgcgactgc cgacgcgaac ggcgtcgact cgtcggtgc        120
cctgtccctc gcgttcaacg tgaacaccgg tcaggtctgc gcgatgcgct gatcgcccgg       180
cgcaccggtt ccgtcccgac cttgcactca ccctgtccga gtgctaaaaa tgcacttggc       240
actcacgacg cgtgagtgcc aggtcgggac ggtgagaccg ggaaccaaag acaccccctgg      300
tcgtccgtcg cgggcaccga actcggccga aggcgtaaat gaggcgaccc gactagcggt       360
cgccttgtgt gtcaccccca atccggagga tcacttcgca                             400
```

<210> SEQ ID NO 3
<211> LENGTH: 32
<212> TYPE: PRT
<213> ORGANISM: Rhodococcus opacus

<400> SEQUENCE: 3

```
Met Asn Arg Arg His Phe Gly Arg Arg Val Ala Ala Gly Leu Thr Ala
 1               5                  10                  15
Ala Val Ala Ala Thr Met Met Phe Thr Gly Val Val Ser Ala Gln Pro
            20                  25                  30
```

<210> SEQ ID NO 4
<211> LENGTH: 43
<212> TYPE: PRT
<213> ORGANISM: Rhodococcus opacus

<400> SEQUENCE: 4

```
Met Arg Val Gly Gly Ser Thr Arg Thr Ser Gly Trp Ala Arg Arg Thr
 1               5                  10                  15
Ala Ala Ala Ile Ala Leu Ala Val Ala Leu Pro Leu Gly Val Thr Met
            20                  25                  30
Val Gly Gly Gly Ala Thr Ala Ser Ala Ala Phe
        35                  40
```

<210> SEQ ID NO 5
<211> LENGTH: 24
<212> TYPE: PRT
<213> ORGANISM: Rhodococcus opacus

<400> SEQUENCE: 5

```
Met Arg Thr Ser Arg Ala Ser Arg Arg Cys Arg Leu Arg Ser Arg Pro
 1               5                  10                  15
Pro Pro Pro Arg Ser Gly Ser Cys
            20
```

<210> SEQ ID NO 6
<211> LENGTH: 32
<212> TYPE: PRT
<213> ORGANISM: Rhodococcus opacus

<400> SEQUENCE: 6

Met Asp Gly Met Ser Val Met Arg Arg Thr Ile Ala Ala Thr Val
1               5                   10                  15

Gly Ile Ala Ala Thr Phe Gly Leu Ser Gly Thr Ala Ala Glu Pro
            20                  25                  30

<210> SEQ ID NO 7
<211> LENGTH: 47
<212> TYPE: PRT
<213> ORGANISM: Rhodococcus opacus

<400> SEQUENCE: 7

Met Glu Arg Arg Val Ser Ala Arg Lys Val Ala His Arg Arg Ile
1               5                   10                  15

Ala Gly Ser Leu Ile Ala Pro Gly Ala Leu Gly Leu Ala Ala Leu Leu
            20                  25                  30

Ala Thr Pro Trp Ser Asn Pro Gly Ser Pro Ala Thr Thr Ala Thr
            35                  40                  45

<210> SEQ ID NO 8
<211> LENGTH: 50
<212> TYPE: PRT
<213> ORGANISM: Rhodococcus opacus

<400> SEQUENCE: 8

Met His Thr Ser Ser Asn Glu Ser Gly His Met Gly Lys Ser Gly Ile
1               5                   10                  15

Gly Phe Ser Arg Asn Lys His Trp Ser Ser Arg Val Ala Val Ala Leu
            20                  25                  30

Thr Gly Ala Val Val Ser Gly Thr Ala Leu Val Gly Ala Ala Gln Ala
            35                  40                  45

Ala Pro
    50

<210> SEQ ID NO 9
<211> LENGTH: 45
<212> TYPE: PRT
<213> ORGANISM: Rhodococcus opacus

<400> SEQUENCE: 9

Met Thr Ser Gln Arg Arg Arg Thr Met Val Asn Arg Thr Ala Ala Gly
1               5                   10                  15

Arg Tyr Gly Val Arg Phe Ala Leu Ala Val Ala Leu Thr Ala Ala Ile
            20                  25                  30

Pro Cys Leu Gly Val Gln Ala Ser Ala Ser Ala Asp Pro
            35                  40                  45

<210> SEQ ID NO 10
<211> LENGTH: 34
<212> TYPE: PRT
<213> ORGANISM: Rhodococcus opacus

<400> SEQUENCE: 10

Met Thr Arg Leu Arg Arg Val Ala Ser Leu Ala Met Pro Ala Leu Leu
1               5                   10                  15

Ala Ser Thr Cys Thr Phe Phe Thr Met Thr Pro Pro Val Ala Thr Ala
            20                  25                  30

Ala Pro

<210> SEQ ID NO 11
<211> LENGTH: 37
<212> TYPE: PRT
<213> ORGANISM: Rhodococcus opacus

<400> SEQUENCE: 11

Met Ser Glu Ile Arg Lys Ser Gly Leu Arg Arg Gly Ala Arg Val Ala
1               5                   10                  15

Gly Leu Gly Ala Ala Ala Ala Val Ala Leu Gly Leu Met Ser Thr Gly
            20                  25                  30

Ala Ala Asn Ala Asp
        35

<210> SEQ ID NO 12
<211> LENGTH: 40
<212> TYPE: PRT
<213> ORGANISM: Rhodococcus opacus

<400> SEQUENCE: 12

Met Ser Gly Arg His Arg Lys Pro Thr Thr Thr Gly Arg Thr Val Ala
1               5                   10                  15

Lys Val Ala Val Thr Gly Ala Ile Met Gly Val Ala Gly Ala Ala Phe
            20                  25                  30

Ser Gly Thr Ala Asn Ala Ala Pro
        35                  40

<210> SEQ ID NO 13
<211> LENGTH: 37
<212> TYPE: PRT
<213> ORGANISM: Rhodococcus opacus

<400> SEQUENCE: 13

Met Ser Glu Asn Arg Lys Thr Gly Leu Arg Arg Gly Ala Arg Ile Ala
1               5                   10                  15

Gly Leu Gly Ala Ala Ala Ala Val Val Leu Gly Leu Met Ser Thr Gly
            20                  25                  30

Ala Ala Asn Ala Asp
        35

<210> SEQ ID NO 14
<211> LENGTH: 45
<212> TYPE: PRT
<213> ORGANISM: Rhodococcus opacus

<400> SEQUENCE: 14

Met Arg Pro Arg Gly Asn Cys Glu Gln Thr Asn Ile Arg Lys Ala Pro
1               5                   10                  15

Met Arg Ser Ser Ile Ala Arg Arg Ala Ala Val Phe Gly Ser Ala Ala
            20                  25                  30

Leu Leu Leu Leu Gly Pro Val Ala Ala Ser Ala Gln Ala
        35                  40                  45

<210> SEQ ID NO 15
<211> LENGTH: 38
<212> TYPE: PRT
<213> ORGANISM: Rhodococcus opacus

<400> SEQUENCE: 15

Met Gln Thr Gly Thr Ser Arg Gly Met Lys Arg Leu Ala Gly Gly Ala
1               5                   10                  15

```
Ala Leu Ala Ala Ala Ala Ala Thr Val Ala Val Thr Met Pro Ala
            20                  25                  30

Thr Ala Ser Ala Ala Thr
        35
```

<210> SEQ ID NO 16
<211> LENGTH: 48
<212> TYPE: PRT
<213> ORGANISM: Rhodococcus opacus

<400> SEQUENCE: 16

```
Met Val Ser Ser Gly His Ala Val Pro Pro Ala Ala Arg Asp Gly Val
1               5                   10                  15

Ser Phe Val Lys Arg Thr Arg Ala Leu Ala Ala Ser Leu Val Gly
            20                  25                  30

Ala Ala Val Thr Leu Ile Ala Phe Ala Gly Pro Ala Ala Ala Asn Pro
        35                  40                  45
```

<210> SEQ ID NO 17
<211> LENGTH: 32
<212> TYPE: PRT
<213> ORGANISM: Rhodococcus opacus

<400> SEQUENCE: 17

```
Met Pro His Arg Arg Pro Lys Pro Ser Ile Val Leu Gly Ala Val Ala
1               5                   10                  15

Ala Leu Ala Val Ala Ser Pro Val Ala Val Tyr Gly Ile Ser Ser Ala
            20                  25                  30
```

<210> SEQ ID NO 18
<211> LENGTH: 40
<212> TYPE: PRT
<213> ORGANISM: Rhodococcus opacus

<400> SEQUENCE: 18

```
Met Ile Val Thr Ala Thr Lys Pro Ser His Gly Trp Leu Arg Gly Val
1               5                   10                  15

Val Arg Leu Met Val Ala Val Val Ile Leu Pro Leu Ala Phe Val Leu
            20                  25                  30

Val Gly Gly Gly Thr Ala Ser Ala
        35                  40
```

<210> SEQ ID NO 19
<211> LENGTH: 37
<212> TYPE: PRT
<213> ORGANISM: Rhodococcus opacus

<400> SEQUENCE: 19

```
Met Thr Asp Ile Ser Thr Ser Arg Phe Gly Tyr Lys Arg Phe Thr Arg
1               5                   10                  15

Ser Val Ala Val Ala Gly Ile Ala Ala Leu Ala Met Val Met Gly Asn
            20                  25                  30

Gly Thr Ala Ser Ala
        35
```

<210> SEQ ID NO 20
<211> LENGTH: 30
<212> TYPE: PRT
<213> ORGANISM: Rhodococcus opacus

<400> SEQUENCE: 20

Met Leu Arg Thr Arg Gly Met Arg Arg Ala Val Thr Ala Leu Ala Val
1               5                   10                  15

Ala Ala Ala Ala Ala Met Ala Val Pro Ala Gln Ala Asn Ala
            20                  25                  30

<210> SEQ ID NO 21
<211> LENGTH: 21
<212> TYPE: PRT
<213> ORGANISM: Rhodococcus opacus

<400> SEQUENCE: 21

Met Thr Ala Ala Phe Cys Leu Ala Leu Ala Val Ser Thr Thr Ala Thr
1               5                   10                  15

Ala Ser Ala Ser Ala
            20

<210> SEQ ID NO 22
<211> LENGTH: 464
<212> TYPE: DNA
<213> ORGANISM: Rhodococcus opacus

<400> SEQUENCE: 22

```
ccggcgagaa cgacgaacga tcccacccag gcggacagcg acaccgcgac cgccttcggg      60
gtggcatcgg tggggtggc gcgcagcggg gtgaccgcga actccggacg cggcggtacg      120
ggtcgcggcg gttccggccg gcgtggcggc tgctcgggtg tcgtcacgca gcgatccta t    180
cgacctgcag taccgtggcg ggccgacgcg cgggtccgtg tcggcggccc cgaagcacgc     240
cgccgaaaca cggcgcccga acaaaatgtg ggcatccggg aacaaatctc cgcacccctc     300
cgttgagcct tacggcaaca tgagcgtgca agactcaagt tcgaattgac tcccgacggt     360
gtcggagtgc aaacttgagc ggagggcgct cactaagcgc caacatcgca gttcagtaat     420
gaaaaacctg cccacaggac tgcaaaacga aagtgaggaa cact                      464
```

<210> SEQ ID NO 23
<211> LENGTH: 400
<212> TYPE: DNA
<213> ORGANISM: Rhodococcus opacus

<400> SEQUENCE: 23

```
gctcgcgctc ggcggcggca tcgcccgttc cggtgcggcc gacggcacca ccaccgtcgc      60
gatcgccggg tggggttcgg gtgcgactgc cgacgcgaac ggcgtcgact gcgtcggtgc     120
cctgtccctc gcgttcaacg tgaacaccgg tcaggtctgc gcgatgcgct gatcgcccgg     180
cgcaccggtt ccgtcccgac cttgcactca ccctgtccga gtgctaaaaa tgcacttggc     240
actcacgacg cgtgagtgcc aggtcgggac ggtgagaccg gaaccaaag acaccctgg      300
tcgtccgtcg cgggcaccga actcggccga aggcgtaaat gaggcgaccc gactagcggt     360
cgccttgtgt gtcaccccca atccggagga tcacttcgca                            400
```

<210> SEQ ID NO 24
<211> LENGTH: 508
<212> TYPE: DNA
<213> ORGANISM: Rhodococcus opacus

<400> SEQUENCE: 24

```
tcgacgtggc gacgatgacg cagccgatct gctcgggatc gatcccgctc gcttcgatcg      60
ccttgcgccc ggcggcgatg gacatcgtga cgacgttctc gtcctccgcc gcgaaccgcc     120
ggttgcggat ccccgagcgc gactggatcc actcgtcgtt cgagtcgatc agttcacaga     180
tctcgtcgtt ggtgacgacc cgttcgggcc ggtacacgcc gagcccgaga agggcggact     240
gccgacctcc agccacggtg gcaatctgct ttcccatcga tcgatctcct catcaggtcc     300
cgcgtggtta cgcgcagtgt ggacttgtcg ccagcacacg ttacgtcggc gaccgcccag     360
cgggtagcac cggttcctgt tactcgtcgg taatatcggt tcgtggtgg tgccgatgaa      420
acgaacaggg cggtcaaacc gacactgtcg taagaacaga cttgttagac ttctggcgat     480
ttccagcagt tgatcaccgg taggggga                                        508
```

<210> SEQ ID NO 25
<211> LENGTH: 527
<212> TYPE: DNA
<213> ORGANISM: Rhodococcus opacus

<400> SEQUENCE: 25

```
tgtctcgtgc gggcggaacg cggaaccggt gaagggtgc acgtattcga aacgcatcgg       60
ggactgggcg tcgaccaggt ggacgtccgt gagctggacg agggaggcga gggcggtgcc     120
ccggtcctcg cgcccgctgc gggcctcggc gagttcggtg cggacgatcg tcggccaccc     180
cggtcccgcg ccgagcctgc ggtagccgga gctgccgacg ggacggcca ccgcttcgag      240
ggtggtgccg gccccggacg tgggaagcgg cgccgcgccc gcgtactgca accccacgg      300
gcgtgcttcg aatcccactg ccccgatcgc cccgagtccg gcaaatgtca ggaatttacg     360
ccgattgatg tcagacacca ggggaacctt aggtgacgac ccgtgagaca ggccgatatt     420
cggctcggcg cggtctacca ccccttctc cttgagcgtt ggcactctca cgtatagagt      480
gccaagtggc gccgatcgag ctccggcacc cgcgacgacg gggctgt                   527
```

<210> SEQ ID NO 26
<211> LENGTH: 586
<212> TYPE: DNA
<213> ORGANISM: Rhodococcus opacus

<400> SEQUENCE: 26

```
aatgatcgac aagcacccgt ggatgcccgg attcctcgac gaggaatggg tgaccgaggc      60
gcgggtcgcg ctcacgtgcc ccgagacgca ggacctgctg acgtcgtatc ggtcggaact     120
gacgtggccg cgattcaagc agaatttcaa ggatgcgctg catttcgcga gttaccgatt     180
cgagcgagtg cccgcatatg aaattcagcg gtgcaatctc gagccgccgt tcccggaacc     240
ggccaaatag ggcgaaccgg gcggggcgtg gtcaccggg gcgtcccggg cagatctcga      300
tgtcggaaca tcagatctcg tttgtgtaac gctggaactg tcggcgacga tgtacgtcga     360
tgatgagtca tcgtgacggt ggtctggaag ttccgtggaa aacgttccgt gagcgtttgt     420
cagggaagtt cgtgtgacat acagtccacc gagcgcagtg tgacttggaa gaggtccgct     480
gccgacccgg cttcatgccc gggccggcag gtcgcctgtt ccccgacgga atccgccgga     540
gccgcctagt ggcggagtcc gcagacgaag agagtgagca gtattc                   586
```

<210> SEQ ID NO 27
<211> LENGTH: 500
<212> TYPE: DNA

<213> ORGANISM: Rhodococcus opacus

<400> SEQUENCE: 27

```
ccgggggcgt gcggagtgac ggtcggatca ccctccgcgg gcgtcgtcgg ctggtgggta    60
cagttccaga cggggcggc agacccgtgt gaagcggcat cgacgcttgc ggatctgacg    120
ctcaatctga gtagttgatg tgcccgtgtc cgtaccgaca gctccgagca gtaccccaca    180
tcgcaggtca gcccttacca ctgccagccc actttgacct tccggcgcgc cgccgggtat    240
cgttgtgggt cgtgtccggc atgcccgggc cgatctgtgt gcctagcgag gtattgccgt    300
gcgcgcgttc gtgcagattt ctgcatggaa cgagcatccg gctgcctgtg tgggggtatg    360
cgacacaccc gacctcgggt gcagctcgag gtgcgggtga ggggcagcag ctctcttgcc    420
ccaactgcta gatccctaat ttcagaacag ccaaggttgc ttgtccagag cagtctgttc    480
aacacgaaga aagccggtaa                                                500
```

<210> SEQ ID NO 28
<211> LENGTH: 500
<212> TYPE: DNA
<213> ORGANISM: Rhodococcus opacus

<400> SEQUENCE: 28

```
gaagcactcg agcaggcgcg cgagaagacc ggtaccgatc cggtcgtcac cctcaagcgc    60
gcactggaca acgtcaagcc tgccctcgag gtccgcagcc gccgtgtcgg tggcgccacc    120
taccaggtgc cggtcgaggt ccgtccgggc cgctccacca ccctcgcgct ccgctggctc    180
gtgaccttct cccggcagcg ccgcgagaag accatggtcg agcgtctcgc caacgagctc    240
ctcgatgcca gcaacggctt gggtgccgct gtgaagcgcc gtgaggacac tcacaagatg    300
gccgaagcca acaaggcatt cgcccactac cgctggtgac gtcacgtcgg agcagtcacc    360
taccgtgact gctccggcgt cgtcgcacgt cgggcccta ccggggaccg gctgatctac    420
aactcgagac aatggccccg ctggtggaac accggggagg ccgacacccg atacacgagc    480
tacgagcggg gaagaatcct                                                500
```

<210> SEQ ID NO 29
<211> LENGTH: 500
<212> TYPE: DNA
<213> ORGANISM: Rhodococcus opacus

<400> SEQUENCE: 29

```
agttctgcag gtcgctggac agcggattct ccagatggac cagtgagcgt gccgcgaccg    60
cgaagaacca ttcccacatc gtctggtcct ggccgctgcg caccagatag ccggtcccga    120
ggtgttttcca ctggcgggcc aacacgaatg cggcgaggcc gacatagaag acgatcgccg    180
cgacgtcggc cgggtggggc cggagacggg agcggagagg gcgagcagtg gtgccggtgc    240
tctctgcctg ccgagtggtc tcgacctggg tgagtatctc agtcacgcag ctgcgcctcc    300
ggttctcggg tcgatgtcaa tcgaccgagg gtaccggagg tcgctgagag cttcctgggt    360
tgcgatcgcg tgattgttgc gtgtatcaca tcaagttgat ttgtgaactt ctgatcaata    420
cagggatatt ctcctgcccc actgttacg ctcagcatgc tttttcgtat cggttgcagt    480
gcactctgaa tggggtcggc                                                500
```

<210> SEQ ID NO 30
<211> LENGTH: 501
<212> TYPE: DNA
<213> ORGANISM: Rhodococcus opacus

<400> SEQUENCE: 30

```
ggagagcgct ctggtttcgc cgtcgctggc cgccaacggc gcgggccgca cggcttgggt    60
ttcgggcgat gcgttcgctg agctcggcgg cgagatcccg gaggaaggcg cgacgctgac   120
caccggttac atcgtggggtt gccagctcga catcaccggc ctcgaggccg gaatcagcgg   180
cagcatgtcg ctcgacggac cgagcgcgag cggtgcgctg agcctgccga tcgcaccggg   240
tgaggtcaag ttcgcgaaga tccgaccaa ggaagacctg aagccgggtg tctcggcgat    300
ccagtaccgc gatcagcaga tcgaggttca gggttgcggt ggctacgcgc aggctcgtgc   360
gtacaccggt ctcgaaattc cggggaacca ctacgtcaag tcgaccctct acgggcagcc   420
gttcagcatc ggctgattgc tcgtaagcag atcccacttc acgacttctc gcgtaagcga   480
cattcaccct agaggggaac a                                             501
```

<210> SEQ ID NO 31
<211> LENGTH: 541
<212> TYPE: DNA
<213> ORGANISM: Rhodococcus opacus

<400> SEQUENCE: 31

```
ggccaagatc gcccgcaacg cggagagcgc tctggtttcg ccgtcgctgg ccgccaatgg    60
cgcgggccgc gttgcgtggg tgtcgggcga cgcgttcgct gagctcggcg gcgagatccc   120
ggaggaaggc gcgacgctga ccaccggtta catcgtgggt tgccagctcg acatcaccgg   180
cctcgaggcc ggtatcagcg gcagcatgtc gctcgacggg ccgagcgcga gcggtgcgct   240
gagcctgccg atcgctccgg gtgaggtcaa gttcgccaag atcaagtcga agacggatct   300
gaagccgggt gtctcggcga tccagtaccg cgatcagcag atcgaggttc agggttgcgg   360
tggctacgcg caggctcgcg cgtacaccgt cctcgaaatt ccggggaacc actacgtcaa   420
gtcgaccctc tacgggcagc cgttcagcat cggctgatcg ccgcgaccga acaaccaacc   480
ttttcgagtc ctgtgggcgg ccacgggcat gcccactgta agaaaccacta gaggggaaca   540
a                                                                    541
```

<210> SEQ ID NO 32
<211> LENGTH: 500
<212> TYPE: DNA
<213> ORGANISM: Rhodococcus opacus

<400> SEQUENCE: 32

```
ggcacccgag gggtttgccc tgggtgcccg agaatgactt ggtgtaagtc tcaacattct    60
cggggtgcgc cgaacttggt gatgtgcttg tcggcggagc agcgacgcca tgcgggtacg   120
gatgcgaaga gcgcgtgaag ctgcatcatg tccgtacctt tccgcgtgtc gttgctggtt   180
ggtagatgac cgtacagcac cggttgaggg tttgcacttc cattatccgg ccactgcgcc   240
gaaatgcagg gttgagcagc ggctcttggc tgagagttgc cgtcccgttc acctccgcgc   300
acggattcgt cagatgtacg gcgtgtggct gatcggtgcg catctgtcga atcccacact   360
ttggtcacag gttgctttcg atccggcctc gggctgccca cacgcacggt gcagctgatt   420
cactcggggc tgatgtgact cgagtggcac ctgtggaagg agagtggcgc ccggactgcg   480
acggtgcgcc cattcccgtt                                                500
```

<210> SEQ ID NO 33
<211> LENGTH: 500
<212> TYPE: DNA

<213> ORGANISM: Rhodococcus opacus

<400> SEQUENCE: 33

```
caacacccgc gccttccagg tgcgtctggc caccctcggt gtcccggcca ccttcgactt      60
ccccgccaac ggcacgcact cgtggccgta ctggggtgcc gagctgtgga aggcacgcgg     120
ccagatcctg gacaccctgg gcgcctggtg atctgacacc accgtcgtga cgactgccgc     180
cccgcctctc cggcggggcg gcactcgtgc gctccggggc gcccgggcct tgcccgggga     240
cgtgagggaa aacccaggat tcccttcccc cgggagtgca caacggaacg ttttgtcagt     300
aaggtgatcc cgtcgagacg ccacccgcgc agcgagcgct gcgcgggtgg cgtctgtacg     360
tgagattttc acgagagtta tcgagaggtt gccgcggccg cggcgcgaga cggatcaagc     420
ggagggaaga cgagttcatg cgtgttgggg gttcgacgag aacaagcgga tgggccaggc     480
gtactgccgc cgcaattgct                                                 500
```

<210> SEQ ID NO 34
<211> LENGTH: 500
<212> TYPE: DNA
<213> ORGANISM: Rhodococcus opacus

<400> SEQUENCE: 34

```
cgatcctcaa accgctcgac ttctacgaca agacggcatt ggtgctggtc atggtgctgt      60
cgctggtgat cgtgctggga gcggaaacat tcggagtcct gggaaccaag gcgccgtacg     120
tcgagccgac gccgtcggac gacgccggat cgccggaatc ggacgataag tagtactacg     180
agatgtagta aaattgaatc gacccggacc ccgtctacac aacgtcgtag atgacttgct     240
aaggtctggg tcaagcgaga gcaatgagag tgcgagtaag ttactcgccg gtattgcatg     300
cttgtaggtg gccgcacttt cagggccgcc gagtcgacga gagtcgccga caccgacaga     360
cgctggactc gaacagtccg cagcagctga cgaatacgcg agtcgagctt gtcgacttgt     420
ttgatcgtca atgtccgatc gaaccgcagt caacgaaggc tgcggaccga ctacgggaga     480
gaacgctgag cgtcatcaac                                                500
```

<210> SEQ ID NO 35
<211> LENGTH: 6
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 35

Leu Ala Xaa Gly Cys Xaa
1               5

CONVERSION OF LIGNIN INTO BIOPLASTICS AND LIPID FUELS

CROSS REFERENCE TO RELATED APPLICATIONS

This application is a 371 National Stage application of International Application No. PCT/US2016/24579, filed Mar. 28, 2016, which claims the benefit of, and priority to, U.S. Provisional Patent Application Ser. No. 62/138,916, entitled "CONVERSION OF LIGNIN INTO BIOPLASTICS AND LIPID FUELS," filed Mar. 26, 2015, which are herein incorporated by reference in their entireties.

STATEMENT REGARDING FEDERALLY SPONSORED RESEARCH

This invention was made with government support under grant number DE-EE0006112 awarded by the Department of Energy. The government has certain rights in the invention.

INCORPORATION OF SEQUENCE LISTING

The substitute sequence listing contained in the file named "TAMC035-revised.txt," which is 19 kilobytes (size as measured in Microsoft Windows®) and was created on Jul. 24, 2019, and which was filed on Nov. 1, 2019 by electronic submission, is incorporated by reference herein. The sequence listing contains no new matter.

INCORPORATION OF SEQUENCE LISTING

The sequence listing that is contained in the file named "TAMC035WO_ST25.txt," which is 18.2 kilobytes as measured in Microsoft Windows operating system and was created on Mar. 28, 2016, is filed electronically herewith and incorporated herein by reference.

FIELD OF THE INVENTION

The present invention relates to the field of molecular biology and genetic engineering. More specifically, the present invention relates to methods for modifying gene expression in microorganisms to achieve synergistic degradation of lignin and increased production of bioproducts.

BACKGROUND OF THE INVENTION

Lignin is the second most abundant biopolymer on the earth and a major component of the plant cell wall. Lignin is also a major waste product for several industries, including the paper and pulping industry and the lignocellulosic biorefinery. Due to the recalcitrant nature of the complex polyphenolic structure, the utilization of lignin for fungible biofuels and bioproducts is a major challenge for both biorefineries and paper/pulping industry. As compared to cellulose and hemicellulose, the methods and systems for utilization of lignin are very limited. The invention included the methods to modify and process lignin toward various bioproducts, all of which are novel approaches and provided important enablement for biofuel, bioproduct, paper, and pulping industry.

SUMMARY OF THE INVENTION

In one aspect, the invention provides a method of lignin depolymerization comprising contacting a sample of biomass comprising lignin with a lignin degradation enzyme and a) at least one electron mediator; or b) at least one bacterium, wherein said lignin degradation enzyme is from a bacterial species different than the at least one bacterium, and wherein said lignin is depolymerized. In one embodiment, the lignin degradation enzyme is selected from the group consisting of a peroxidase, laccase, and cellobiose dehydrogenase. In another embodiment, the peroxidase is selected from the group consisting of a dye-decolorizing peroxidase, a lignin peroxidase, a manganese peroxidase, and a versatile peroxidase. In another embodiment, the dye-decolorizing peroxidase is from *Amycolatopsis* sp. 75iv2. In further embodiments, the at least one electron mediator selected from the group consisting of 1-hydroxybenzotriazole (HBT), 2,2'-azino-bis-(3-ethylbenzothiazoline-6-sulfonic acid) (ABTS), acetosyringone, phenol, and violuric acid, or the at least one bacterium is selected from the group consisting of *Rhodococcus, Pseudomonas, Bacillius cupriavidus, Streptomyces* and *Ralstonia*. In Another embodiment, such a method further comprises processing the resulting depolymerized lignin to produce a biological product or to separate the depolymerized lignin into different parts, or the processing comprises fermentation, mixing with asphalt at a high temperature, or electrospinning. In other embodiments, the biological product is selected from the group consisting of a biofuel, a biofuel intermediate, a therapeutic compound, a bioplastic, a lipid, a terpene, a nutraceutical compound, a terpenoid-derived compound, an asphalt binder, a carbon fiber, and a carbon containing compound, or the bioplastic is PHA. In a still further embodiment, said depolymerization and fermentation occur simultaneously.

In another aspect, the invention provides a lignin depolymerization composition comprising: a) a lignin degradation enzyme; and i) at least one electron mediator; or ii) at least one bacterium, wherein said lignin degradation enzyme is from a bacterial species different than the at least one bacterium. In some embodiments, the lignin degradation enzyme is selected from the group consisting of a peroxidase, laccase, and cellobiose dehydrogenase, or the peroxidase is selected from the group consisting of a dye-decolorizing peroxidase, a lignin peroxidase, a manganese peroxidase, and a versatile peroxidase, or said dye-decolorizing peroxidase is from *Amycolatopsis* sp. 75iv2. In another embodiment, the at least one electron mediator selected from the group consisting of 1-hydroxybenzotriazole (HBT), 2,2'-azino-bis-(3-ethylbenzothiazoline-6-sulfonic acid) (ABTS), acetosyringone, phenol, and violuric acid. In another embodiment, the at least one bacterium is selected from the group consisting of *Rhodococcus, Pseudomonas, Bacillius cupriavidus, Streptomyces* and *Ralstonia*.

In another aspect, the invention provides a method of producing a biological product, said method comprising expressing in a bacterium a first expression cassette comprising a lignin depolymerization module and a second expression cassette comprising PHA production module, wherein said lignin depolymerization module comprises a lignin degradation enzyme, a promoter driving expression of the lignin degradation enzyme, and a secretion signal peptide and said PHA production module comprises a PHA synthesis gene and a promoter driving expression of the PHA synthesis gene, and wherein expression of said first and second expression cassettes results in lignin depolymerization and production of the biological product. In one embodiment, the PHA synthesis gene comprises phaC1, phaC2, phaJ, phaJ4, phaF and phaI. In another embodiment, such a method further comprises expressing in the bacterium a third expression cassette comprising an aromatic compound degradation module comprising an aromatic degradation gene and a promoter driving expression of the aromatic degradation gene. In other embodiments, the aromatic degradation gene comprises a vanA or vanB gene, or the first and second expression cassettes are comprised in a single DNA construct, or the first, second and third expression cassettes are comprised in a single DNA construct. In a still further embodiment, the biological product is selected from the group consisting of a biofuel, a biofuel intermediate, a therapeutic compound, a bioplastic, a lipid, a terpene, a nutraceutical compound, a terpenoid-derived compound, an asphalt binder, a carbon fiber, and a carbon containing compound, or the bioplastic is PHA. In other embodiments, said lignin degradation enzyme is selected from the group consisting of a peroxidase, laccase, and cellobiose dehydrogenase, or the peroxidase is selected from the group consisting of a dye-decolorizing peroxidase, a lignin peroxidase, a manganese peroxidase, and a versatile peroxidase, or said dye-decolorizing peroxidase is from *Amycolatopsis* sp. 75iv2. In further embodiments, said method is used to pretreat biomass, or said secretion signal peptide comprises a Sec-pathway-dependent type II peptide comprising an A-X-A and/or a L-A-X-G-C-X (SEQ ID NO:35) motif, or said secretion signal peptide is selected from the group consisting of OprI, OprF, Pbp and PelB. In a further embodiment, such a method further comprises overexpression of FASI, atf2, or FASI and atf2.

In another aspect, the invention provides an engineered bacterium comprising a lignin depolymerization module and a PHA production module, wherein said lignin depolymerization module comprises a lignin degradation enzyme, a promoter driving expression of the lignin degradation enzyme, and a secretion signal peptide and said PHA production module comprises a PHA synthesis gene and a promoter driving expression of the PHA synthesis gene. In one embodiment, the PHA synthesis gene comprises phaC1, phaC2, phaJ, phaJ4, phaF and phaI. In another embodiment, such a bacterium further comprises an aromatic compound degradation module comprising an aromatic degradation gene and a promoter driving expression of the aromatic degradation gene. In another embodiment, the aromatic degradation gene comprises a vanA or vanB gene. In other embodiments, said lignin degradation enzyme is selected from the group consisting of a peroxidase, laccase, and cellobiose dehydrogenase, or the peroxidase is selected from the group consisting of a dye-decolorizing peroxidase, a lignin peroxidase, a manganese peroxidase, and a versatile peroxidase, or said dye-decolorizing peroxidase is from *Amycolatopsis* sp. 75iv2. In further embodiments, said secretion signal peptide comprises a Sec-pathway-dependent type II peptide comprising an A-X-A and/or a L-A-X-G-C-X (SEQ ID NO:35) motif, or said secretion signal peptide is selected from the group consisting of OprI, OprF, Pbp and PelB, or said engineered bacterium is used to pretreat biomass. In another embodiment, the invention provides a composition produced from culturing such an engineered bacterium.

In another aspect, the invention provides a method for increasing expression of protein of value in a Gram positive bacterial species, said method comprising expressing in said bacterial species a DNA construct comprising a gene encoding the protein of value, a signal peptide, a promoter, a ribosomal binding site, and a transporter, wherein expression of said DNA construct results in degradation of lignin. In some embodiments, such a method may comprise expression, overexpression, and/or secretion of any protein of value. In a further embodiment, such a method may comprise expression, overexpression, and/or secretion of more than one protein of value. In one embodiment, expression of said DNA construct results in increased production of laccase, a lipid, or a therapeutic protein. In some embodiments, said signal peptide is a twin-arginine translocation (Tat) signal peptide selected from the group consisting of S2587, TatA, and TatC, or said DNA construct comprises both TatA and TatC, or said TatA and TatC are in the same operon as laccase, or wherein TatA and TatC are present in the same bacterial strain with laccase. In another embodiment, said ribosomal binding site is selected from the group consisting of R704 and R756. In still further embodiments, the protein of value is a laccase, an endoglucanase, an exoglucanase, a xylanase, or lunasin, or said bacterial species is Gram positive *Rhodococcus opacus*.

BRIEF DESCRIPTION OF THE FIGURES

FIG. 8—Shows growth curves and vanillate degradation curves of *P. putida* A514 with the pPROBE-GT plasmid containing only the van promoter (control) or the promoter and the vanAB genes. Strains were grown in M9 medium with 25 mM (A) and 60 mM (B) vanillate as the sole carbon source.

*R. opacus* PD630 showed an exponential increase of cell growth associated with laccase concentration. B) The Fenton reaction has limited synergistic effect with laccase treatment to promote *R. opacus* PD630 cells growth in lignin fermentation. Except the no laccase control, all treatments contained laccase at a concentration of 1.0 U/ml in RM medium. Without Fe$^{2+}$ medium: RM medium without FeSO$_4$. Fe$^{2+}$: addition of 0.2 mM FeSO$_4$. FeCl$_3$: addition of 0.2 mM FeCl$_3$. NaFeEDTA: 0.2 mM NaFeEDTA. Control: only the *R. opacus* cells were added to fermentation medium.

Figure 12A:
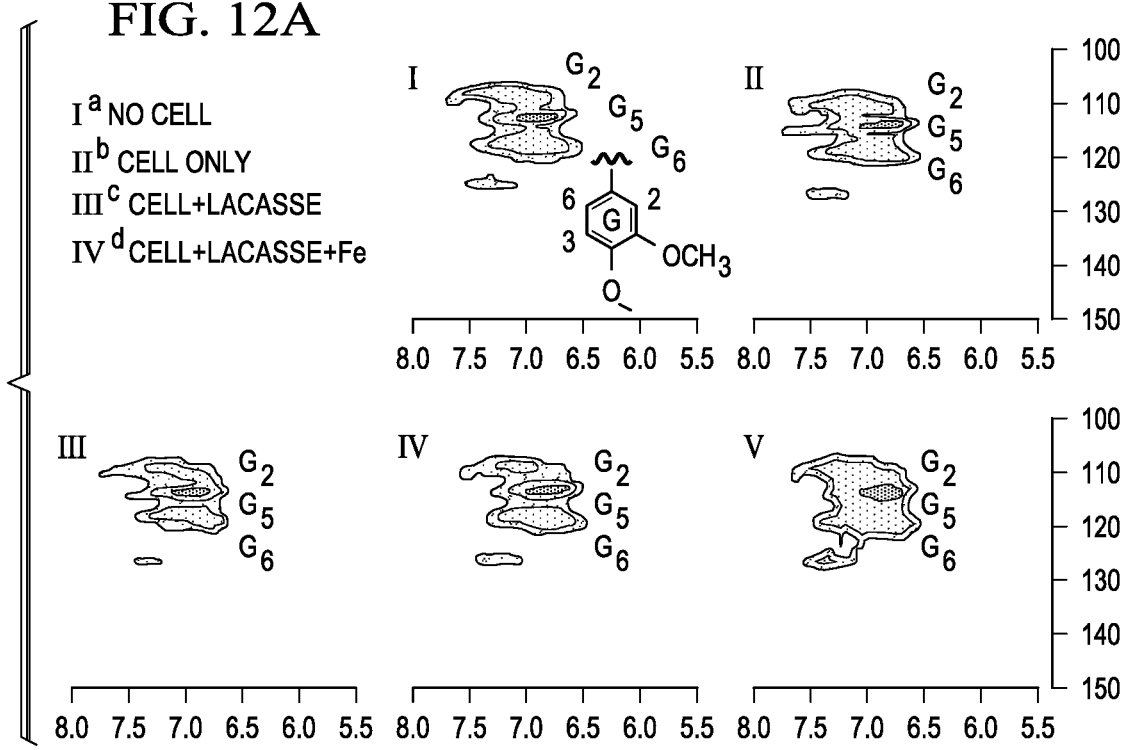
Figure 12B:
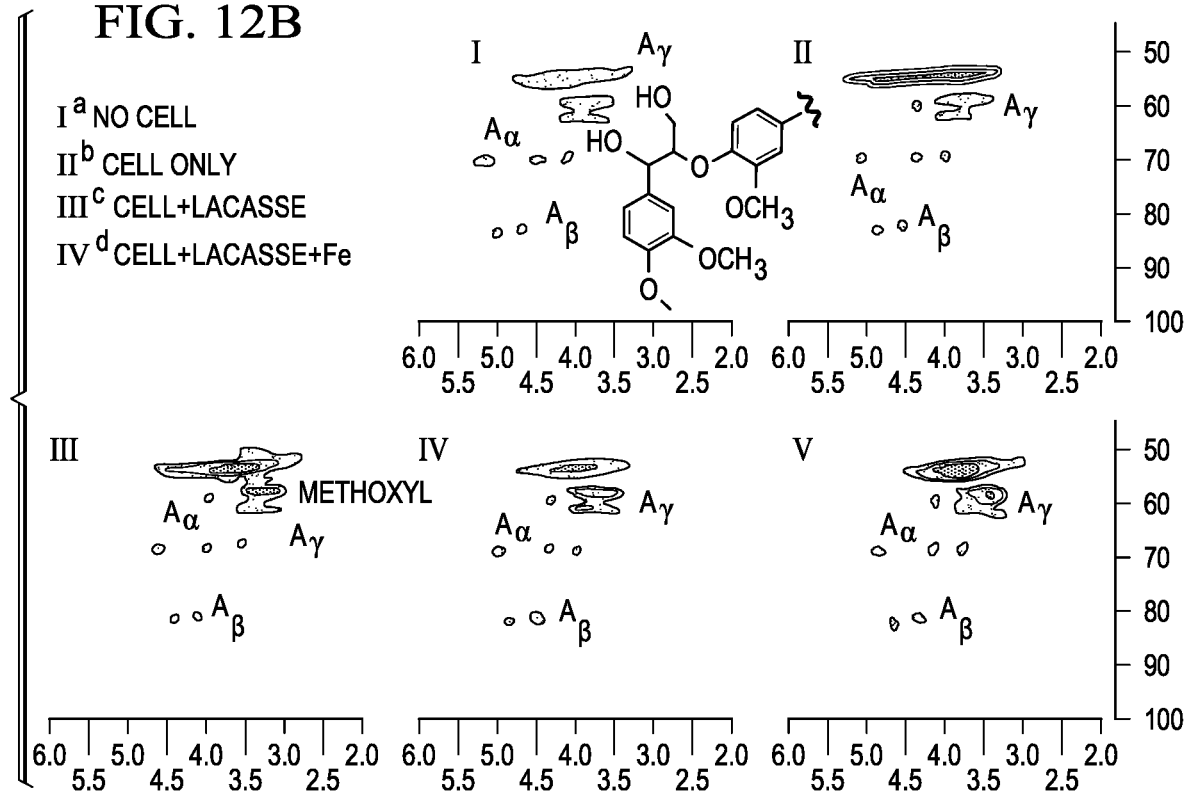

FIG. 12—Shows HSQC analysis of lignin after different treatment. A) The aromatic region of HSQC NMR spectra of lignin obtained after treatments: (I) no cell, (II) cell only, (III) laccase, (IV) laccase and Fe$^{2+}$, and (V) laccase and Fenton reagent. B) Aliphatic region of HSQC NMR spectra of lignin obtained after treatments: (I) no cell, (II) cell only, (III) laccase, (IV) laccase and Fe$^{2+}$, and (V) laccase and Fenton reagent.

Figure 13:
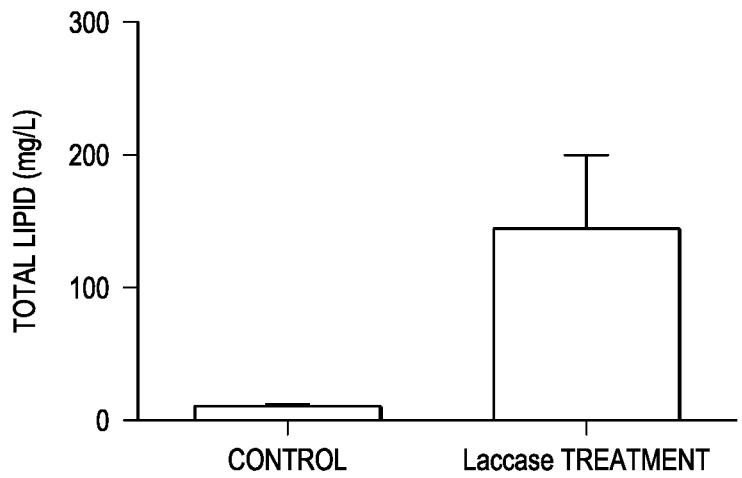

FIG. 13—Shows lipid yield of *Rhodoccocus opacus* PD630 with and without laccase treatment. Laccase increased lipid yield from *R. opacus* PD630. For the control group, *R. opacus* PD630 cells were added to fermentation medium without laccase treatment. For laccase treatment, the cells and laccase were added to fermentation medium simultaneously.

Figure 14A:
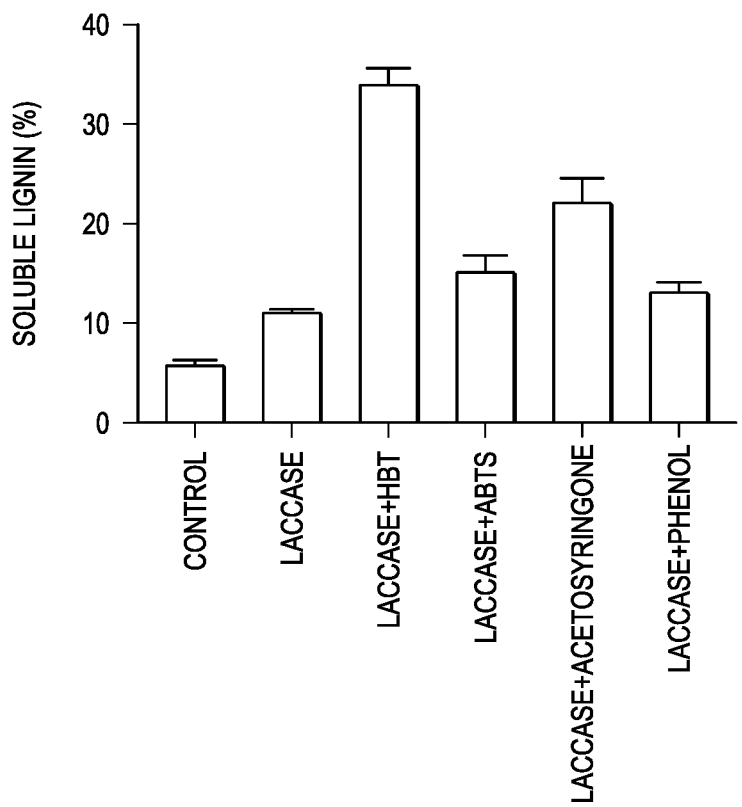
Figure 14B:
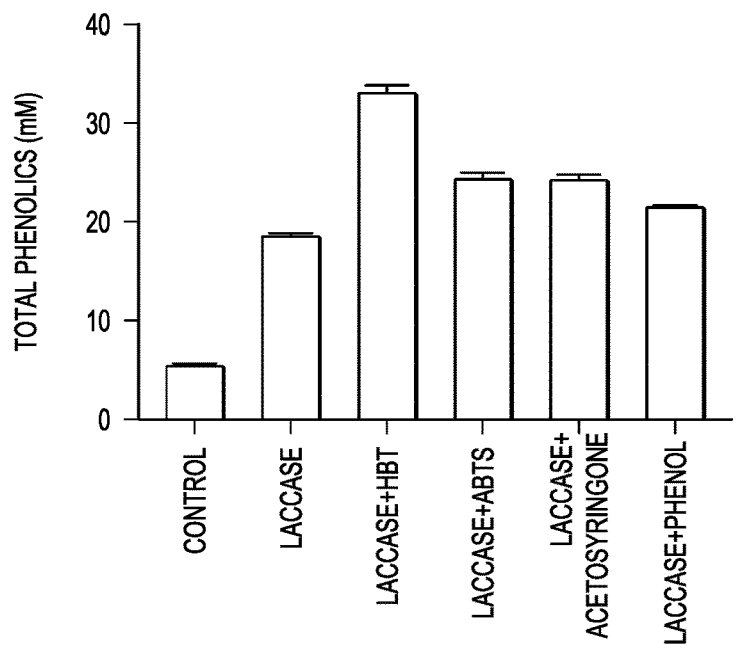
Figure 14C:
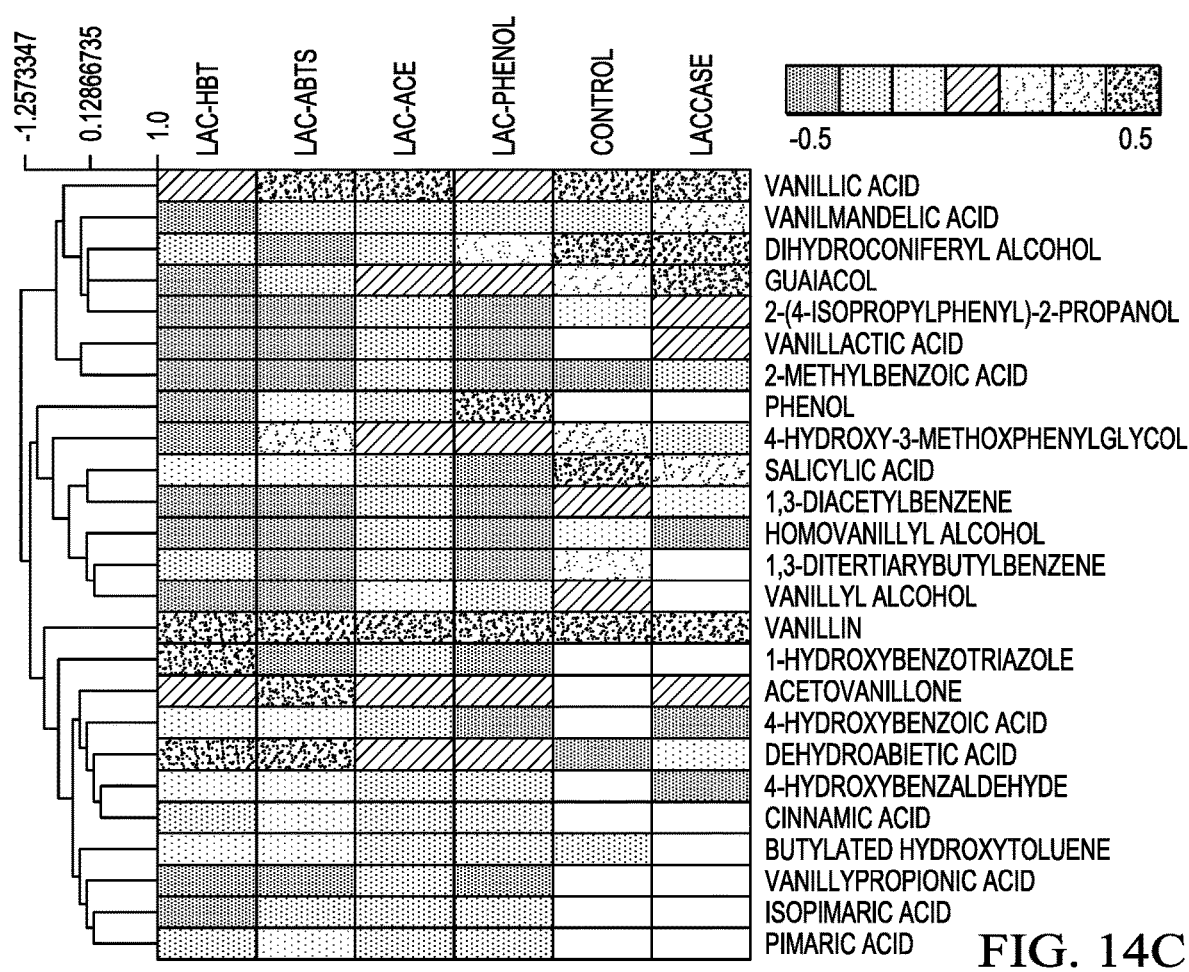

FIG. 14—Shows the depolymerization and solubilization of kraft lignin by different laccase-mediator systems. (A) The percentage of the solubilized lignin as calculated from the weight loss of the kraft lignin after the different laccase-mediator treatments. (B) The estimated total soluble aromatic compounds in solution determined by Prussian Blue assay. (C) The heatmap of the relative abundance of the monomer aromatic compounds in the solubilized lignin solution as detected by GC-MS analysis.

FIG. 15—Shows the molecular weight properties of the insoluble fraction of kraft lignin after laccase and laccase-HBT treatments as revealed by GPC analysis. The changes of Mw (A), Mn (B) and PDI (C) for kraft lignin after the laccase-HBT (Lac+HBT) treatment and laccase only (Lac) treatment.

FIG. 16—Shows pretreated lignin with laccase. Electron mediator promoted lignin solubilization and lipid production. A) Solubilization of lignin by laccase and electron mediator treatment. B) Increase of cell growth. C) Increase of lipid.

Figure 17:
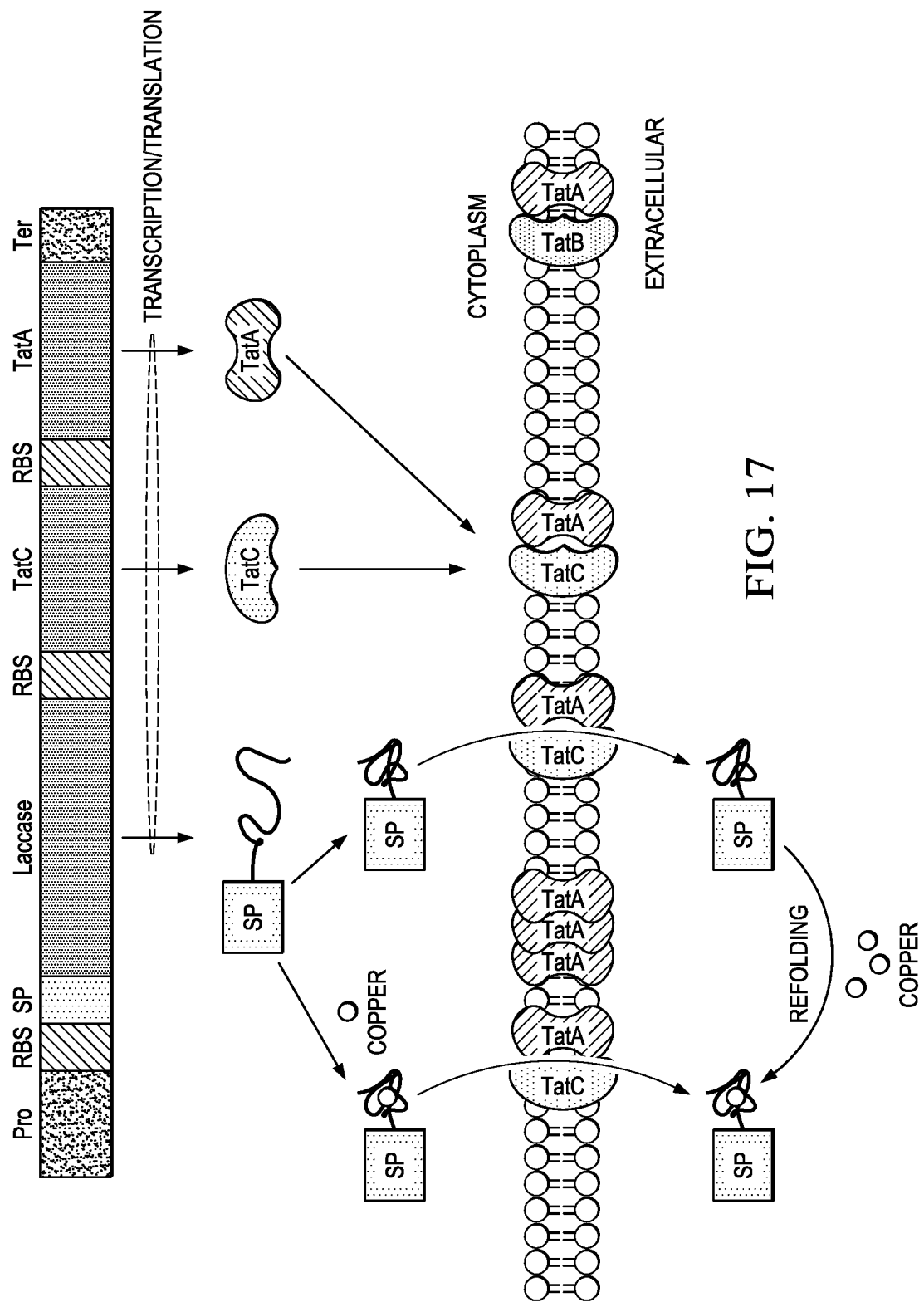

FIG. 17—Shows the secretion system can be engineered to increase laccase secretion.

Figure 18:
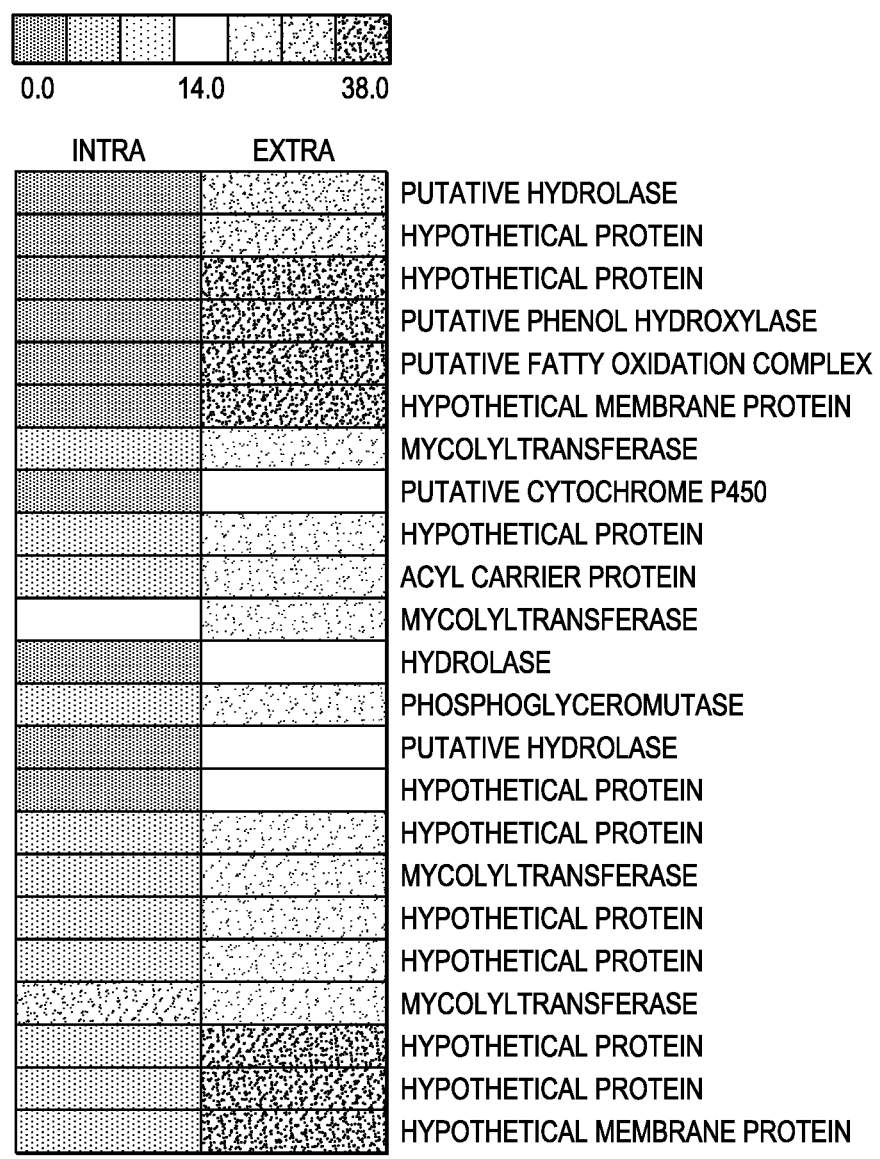

FIG. 18—Shows the comparative entracellular proteomics and extracellular secretomics of *Rhodooccus opacus* to discover the signal peptides for laccase secretive expression.

Figure 19:
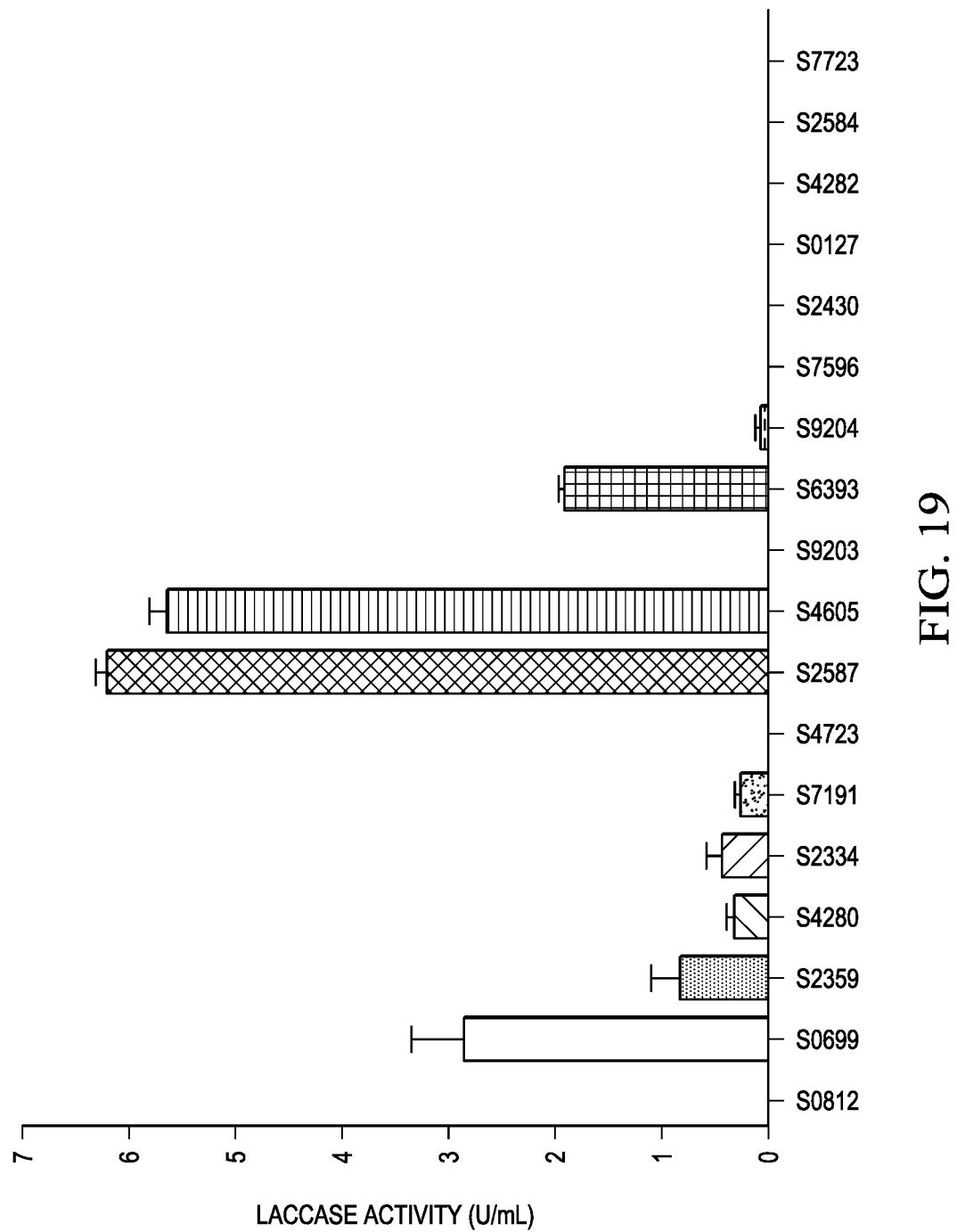

FIG. 19—Shows different signal peptides for laccase secretive expression.

Figure 20A:
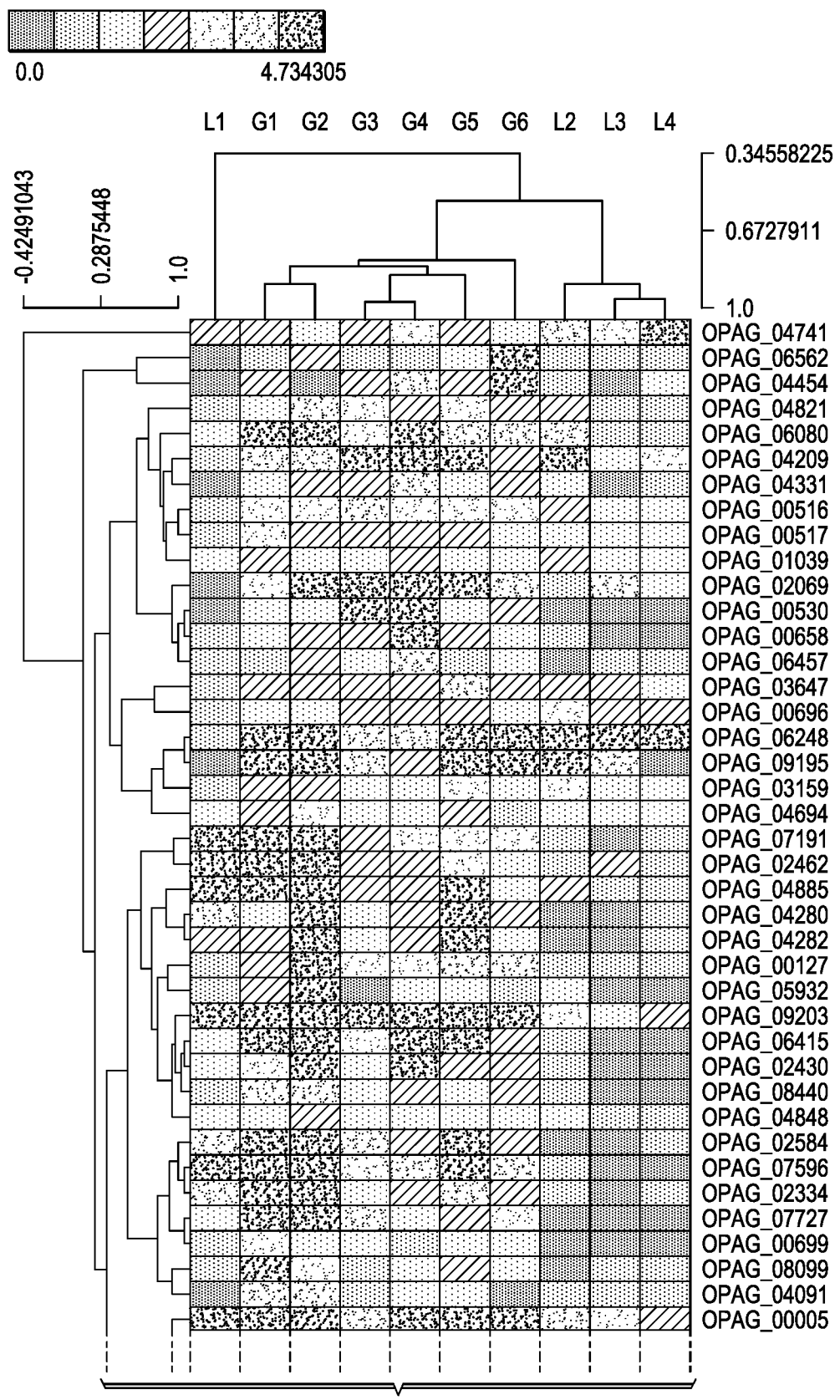
Figure 20B:
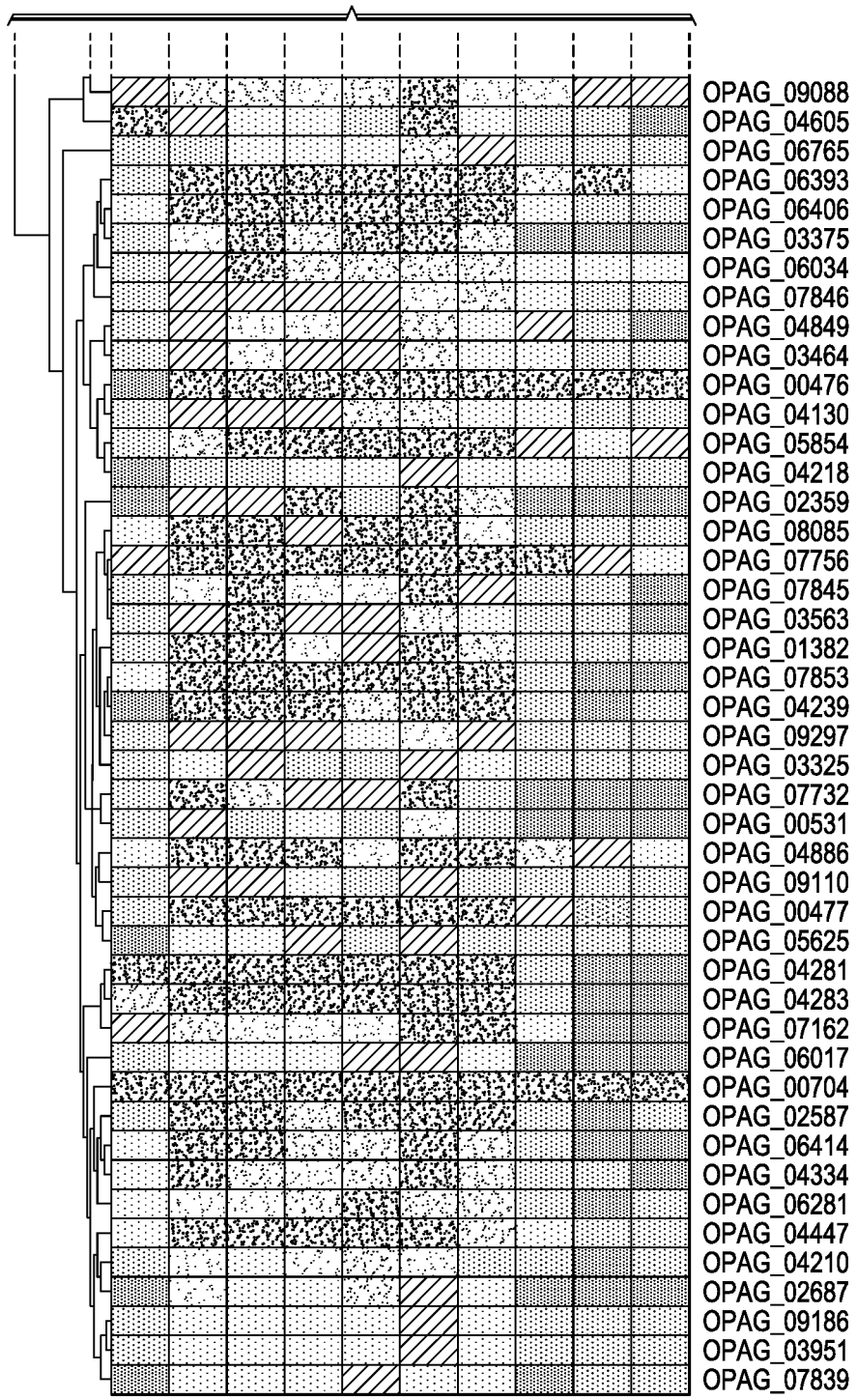

FIG. 20—Shows comparative proteomics for discovery of promoters and RBS for protein heterologous expression in *Rhodooccus opacus*.

Figure 21:
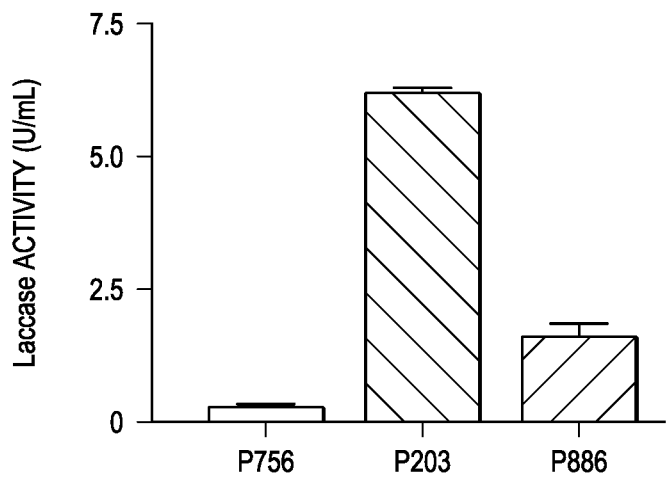

FIG. 21—Shows different promoters and RBS to promote laccase expression.

Figure 22:
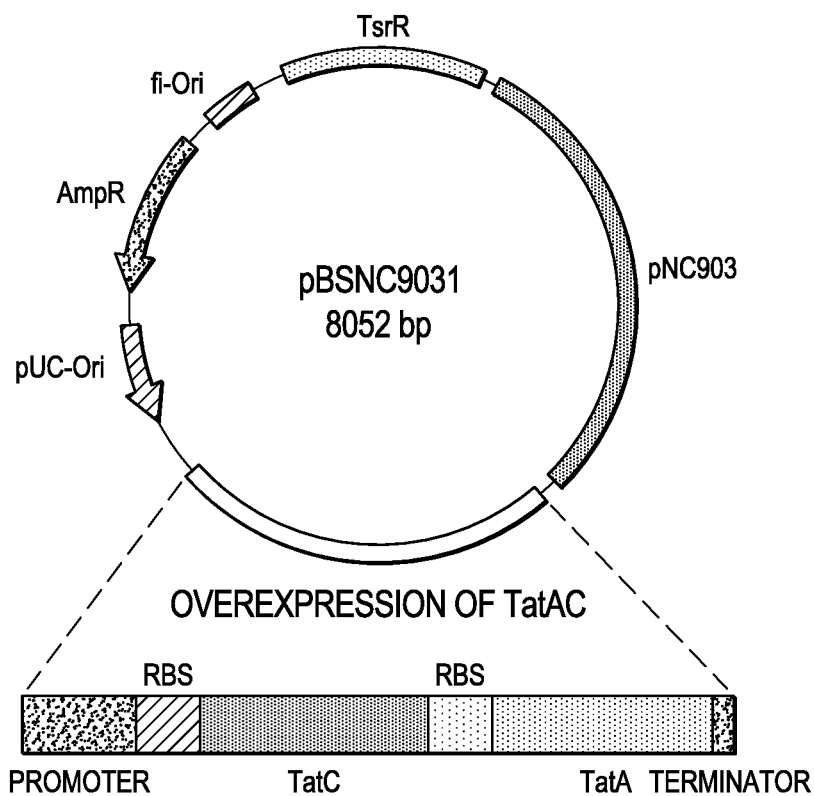

FIG. 22—Shows the construct design for overexpression of key components of TatA and TatC in the Tat transportation system.

Figure 23:
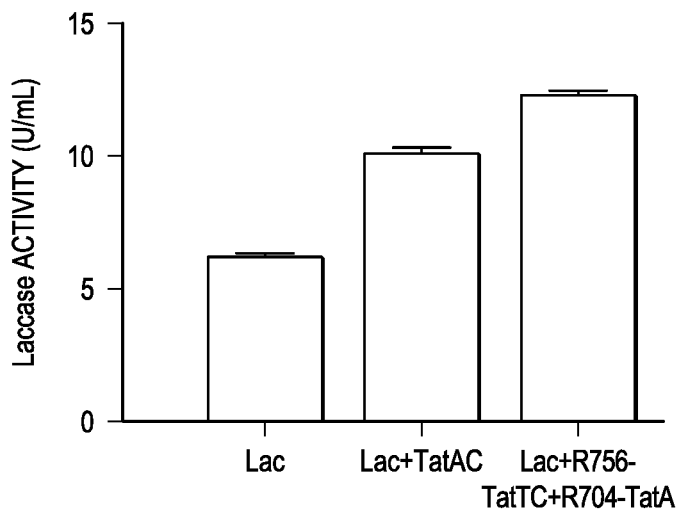

FIG. 23—Shows expression of laccase at high activity through integration of secretion system engineering and enzyme engineering.

Figure 24:
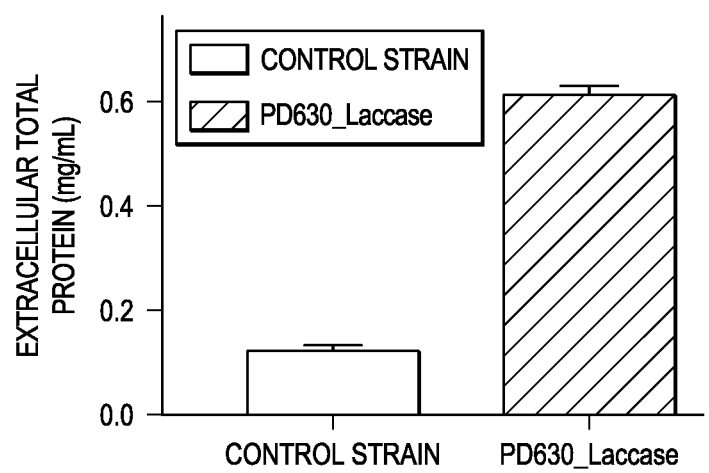

FIG. 24—Shows significant increase of total secretion protein by multiple step engineering.

Figure 25:
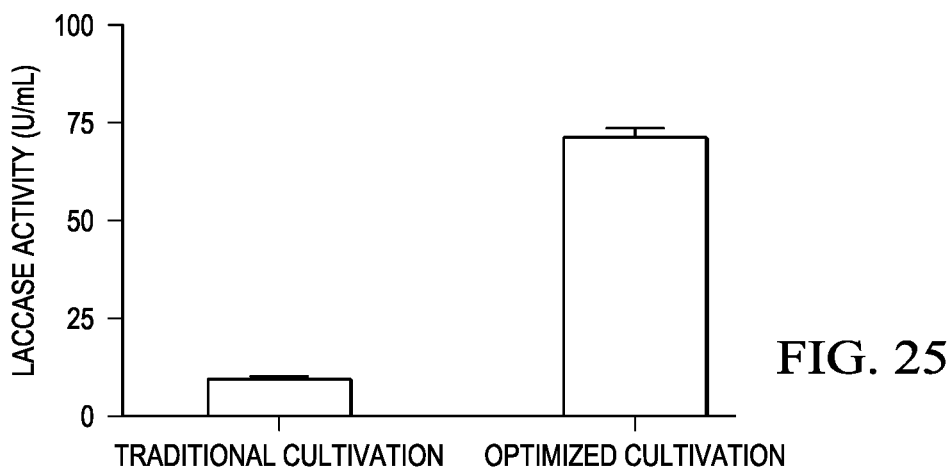

FIG. 25—Shows record high laccase activity by optimizing copper conditions in the media.

Figure 26:
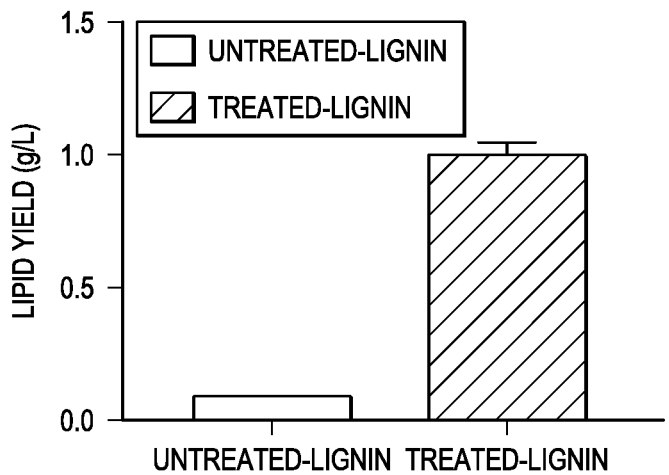

FIG. 26—Shows increased lipid yield by laccase treatment.

Figure 27:
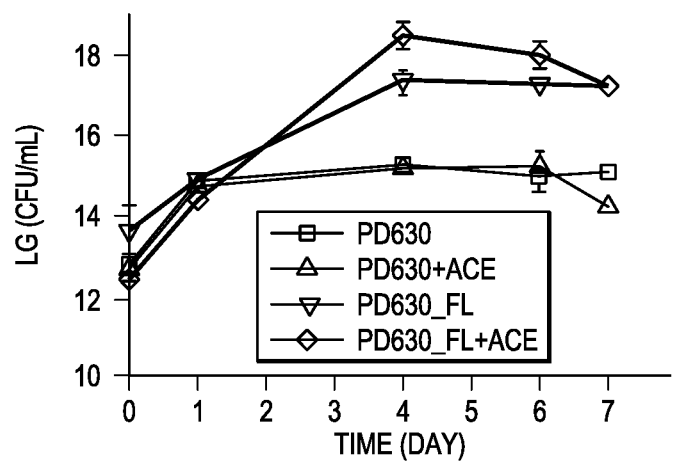

FIG. 27—Shows >1000-fold increase in cell growth by laccase engineering.

Figure 28:
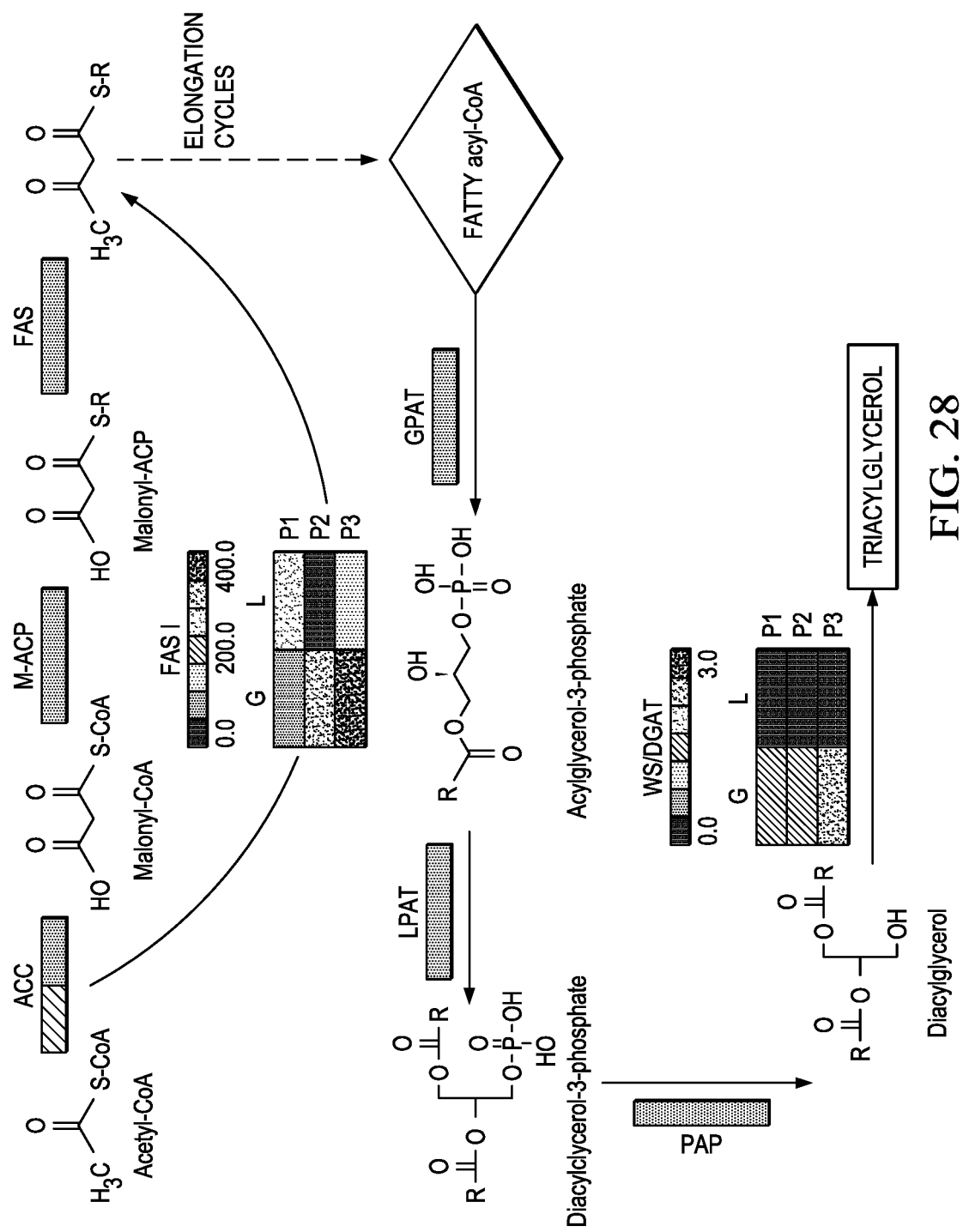

FIG. 28—Shows identification of FAS1 as a key enzyme for lipid biosynthesis.

Figure 29:
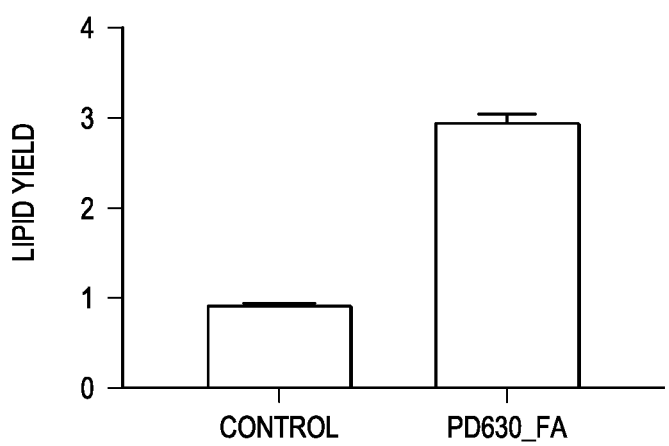

FIG. 29—Shows engineering of FAS1 alone or FAS1 and atf will increase lipid yield in bacteria.

Figure 30:
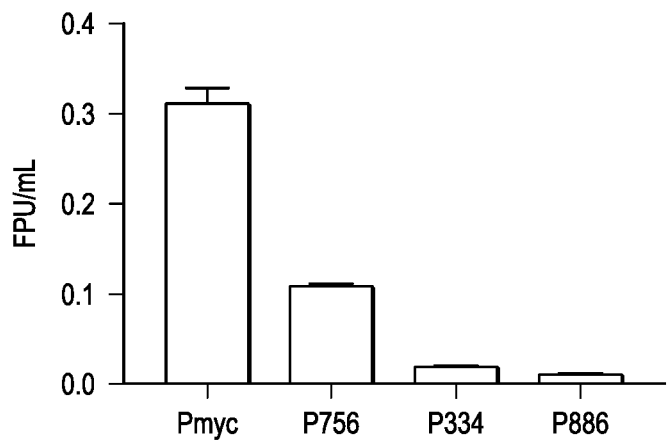

FIG. 30—Shows heterologous expression of termite endogluconanse in *Rhodococcus* with the aforementation engineered secretive system.

Figure 31A:
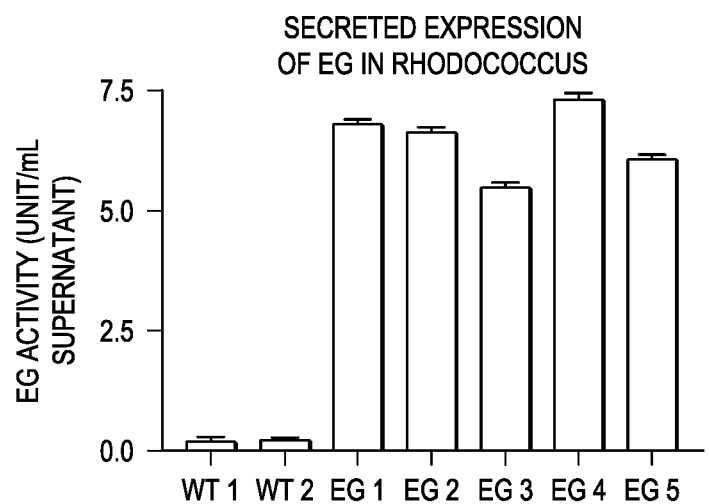
Figure 31B:
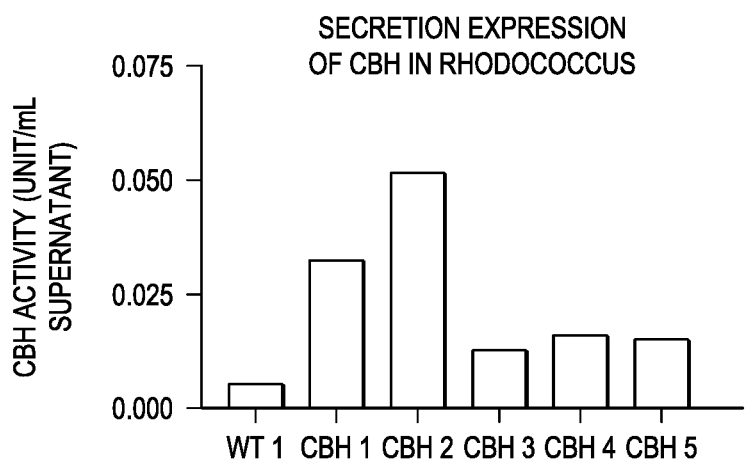
Figure 31C:
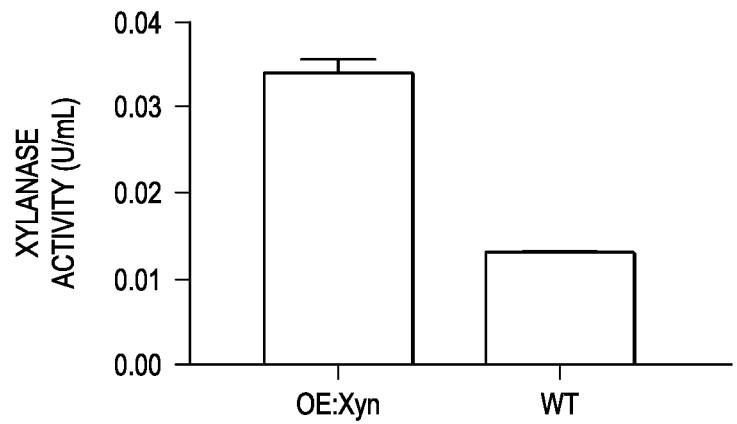

FIG. 31—Shows the heterologous expression of cattle rumen endogluconanse (A), cellobiohydrolase (B), and xylanase (C) in *Rhodococcus* with the aforementation engineered secretive system.

Figure 32:
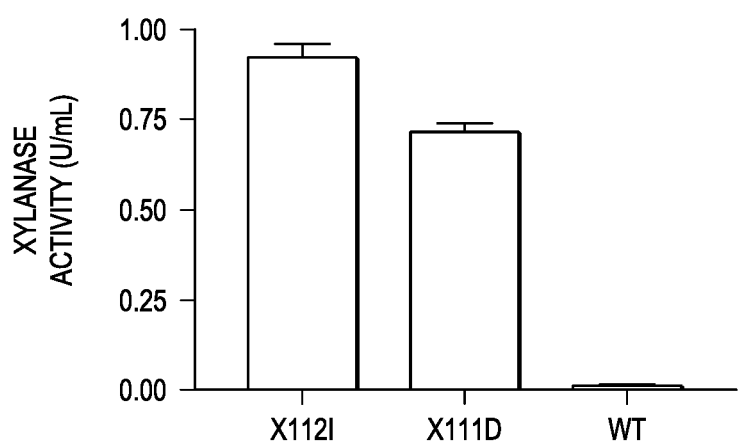

FIG. 32—Shows heterologous expression of filementous fungi *Trichoderma reesei* xylanase in *Rhodococcus*.

Figure 33:
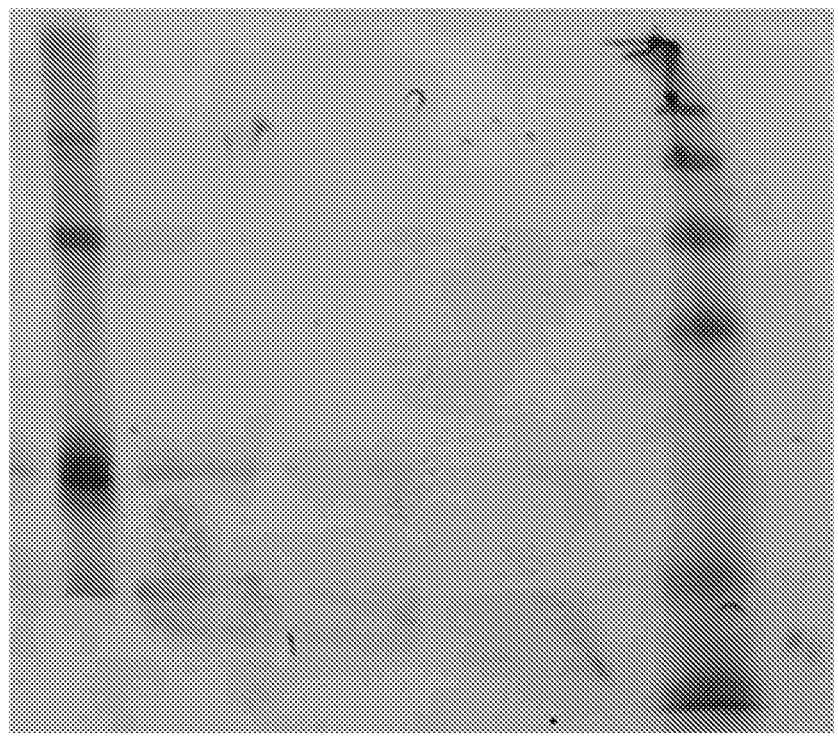

FIG. 33—Shows heterologous expression of the anti-cancer peptide lunasin in *Rhodococcus*.

Figure 34A:
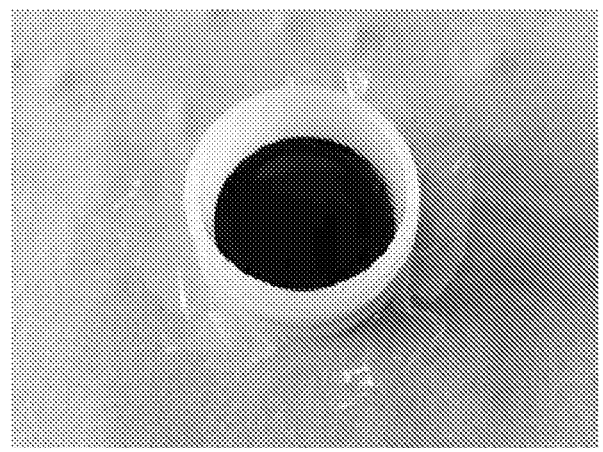
Figure 34B:
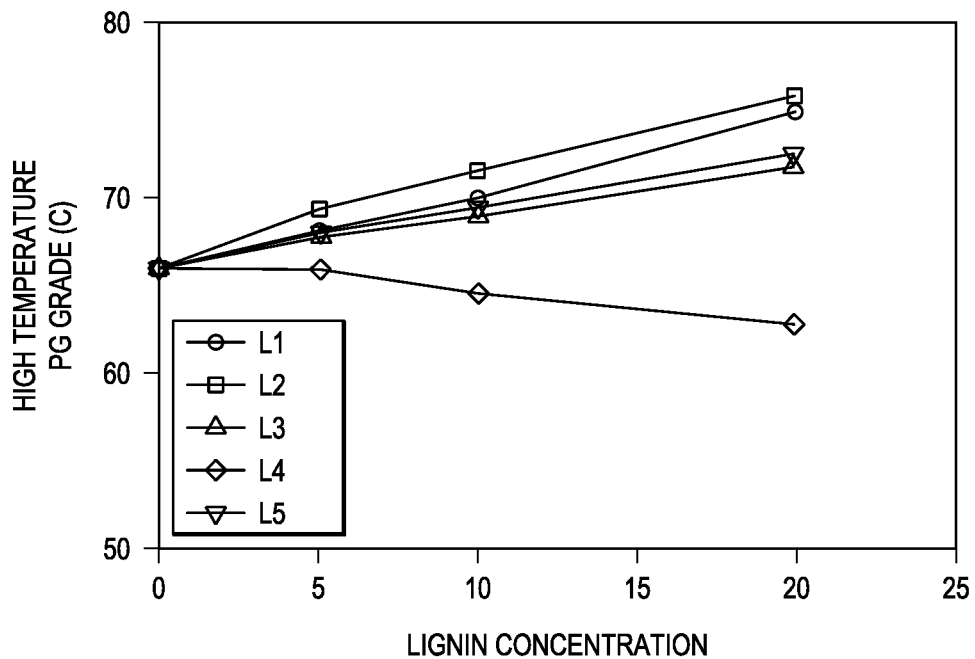
Figure 34C:
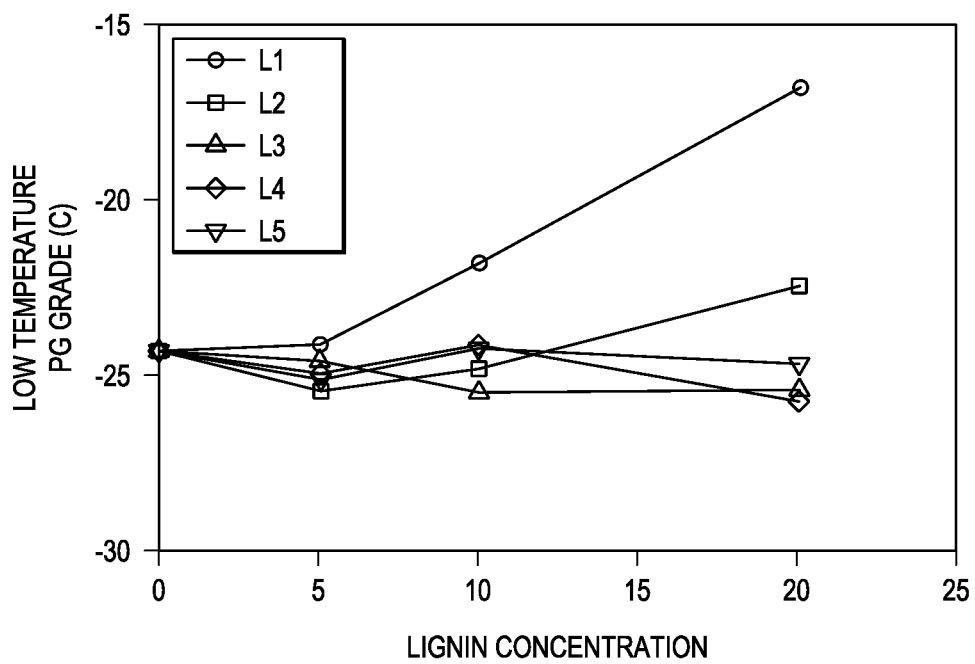

FIG. 34—Shows the improved properties of asphalt binder mixed with lignin treated by laccase or formic acid. The insoluble part of laccase-HBT treated lignin could significantly improve high-temperature properties and reduce low-temperature cracking of asphalt binder. The insoluble part of formic acid-treated lignin reduced high temperature property a little bit, but did not improve low temperature cracking property much. The soluble part of lignin treated by either laccase-HBT or formic acid significantly improve high temperature property without reduce low temperature cracking property of asphalt binder. (A) The picture of asphalt binder made by adding treated lignin; (B) the high temperature property of asphalt binder made by adding different treated lignin; (C) the low temperature cracking property of asphalt binder made by adding different treated lignin. L1: raw lignin; L2: Laccase treated insoluble part; L3: Laccase treated soluble part; L4: Formic acid treated soluble part; L5: Formic acid treated insoluble part.

Figure 35:
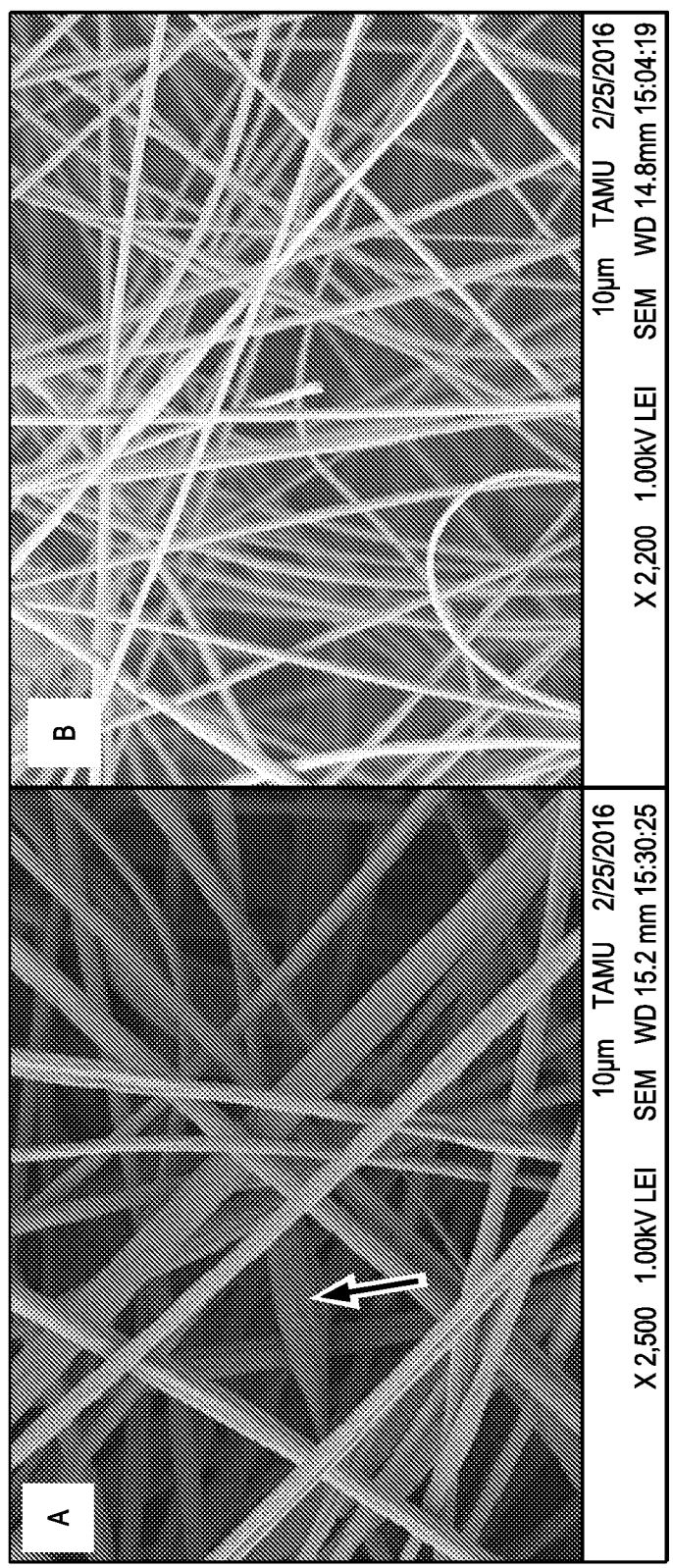

FIG. 35—Shows electronspun lignin fibers. (A), Kraft lignin fiber, (B), Laccase-HBT treated Kraft lignin fiber. Both fibers were made after blending 50% lignin with 50% PAN.

DETAILED DESCRIPTION OF THE INVENTION

The present invention provides methods for processing of lignin and biorefinery waste using enzymes, chemical mediators, bacterial cells, and redox inducing agents, along with combinations thereof to result in lignin and biorefinery waste more processable for producing lipid, PHA, carbon fibers, and asphalt binders of distinct qualities. From a holistic point of view, the invention is based on the understanding of lignin degradation in a redox environment, and thus provides the systems and methods with different embodiments to convert lignin and biorefinery waste. In particular, the enzyme treatment involves laccase and peroxidase. The mediator includes HBT (1-hydroxybenzotriazole), ABTS (2,2'-azino-bis(3-ethylbenzothiazoline-6-sulphonic acid)), acetosyringone, phenol, and violuric acid. The chemicals include various iron ions (such as $Fe^{2+}$, $Fe^{3+}$, and NaFeEDTA), hydrogen peroxide, and formic acid. The different combination of these treatment will make biorefinery waste and render lignin more processible toward bioconversion using engineered strains, asphalt binders to change performance of road material, and the carbon fibers.

The present invention provides systems and methods of degrading lignin more efficiently to produce various products. For example, the treatment of lignin and biorefinery waste with laccase and HBT, an electron mediator, will significantly promote the lignin depolymerization and thus make lignin more processible for PHA and lipid. Moreover, the processed lignin can serve as an asphalt binder to improve the performance of asphalt. Moreover, the lignin derived from this process can be used for electro-spinning to make carbon fiber of improved quality.

In addition, the present invention provides systems and methods for producing a biological product comprising expressing in *Pseudomonas putida* strain A514 at least a first DNA construct comprising a lignin depolymerization module, an aromatic compound degradation module, and a PHA production module; wherein the lignin depolymerization module comprises a lignin degradation enzyme, a promoter, and a secretion signal peptide; wherein the aromatic compound degradation module comprises a Pvan promoter and a vanAB gene; and wherein the PHA production module comprises a Pvan promoter, and one of phaJ4 or phaC1; wherein expression of the DNA construct results in increased degradation of lignin and increased production of the bioproduct. Also provided are bacterial cells produced by such methods, as well as compositions produced from culturing such bacterial cells.

The invention also provides systems and methods for increasing expression of laccase in a Gram positive bacterial species, comprising expressing in the bacterial species a DNA construct comprising laccase, a signal peptide, and a promoter; wherein the promoter is selected from the group consisting of p1099, wherein expression of the DNA construct results in increased degradation of lignin. Besides the lignin degradation, the system and method can be used to produce a variety of proteins of values including endoglucanase, exoglucanase, anti-cancer lunasin proteins and such. These proteins are from, plant, bacteria, fungus and insects. The invention thus teaches a method to produce a valuable protein in secretion from different sources and for different functions. The secretion expression significantly simplifies the purification and thus is of significant value. In accordance with the invention, such methods produce increased production of laccase, lipids, or therapeutic proteins.

In embodiments of the invention, biological and chemical modification of lignin results in lignin being more easily processed into various products. Therefore, the combination of engineered microorganisms, as well as biological and chemical processing, allows lignin to be converted into a broad range of products, including, but not limited to, PHA (bioplastics), lipid, asphalt binder, and carbon fiber. The invention further provides various combinations of biological and chemical treatments to enable lignin to be reactive for production of different compounds. The invention also provides methods for treatment of lignin, including biological, chemical, and other approaches. Genetic engineering may be used heavily to allow higher enzyme production and modified metabolism.

Bioethanol represents one of the most mature form of biofuel to displace fossil fuels and mitigate global climate changes. Current U.S. bioethanol production (~15 billion gallons annually), derived primarily from corn, contributes ~10% to the gasoline transportation fuel supply. However, the U.S. Energy Independence and Security Act (EISA) bill contains provisions that increase the Renewable Fuel Standard (RFS) to 36 billion gallons by 2022, among which 22 billion gallons must be advanced biofuel derived from nonfood-based biomass, the majority of which will be lignocellulosic biofuels. The USDA/DOE Updated Billion Ton report reviewed these demands and concluded that these goals can be addressed using lignocellulosic biomass including: perennial crops, wheat straw, corn stover, other agricultural crop residues, forest residues, tree farms (i.e., hybrid poplar), secondary forest industry waste materials, and other energy crops.

Lignocellulosic biomass has been sought after as the primary feedstock for sustainable production of fuels and chemicals. Even though significant progress has been made to process cellulose and hemicellulose to advanced biofuels, the efficient utilization of lignin remains a major technical barrier for modern biorefineries. Despite the potential, the bioprocessing of lignin into fungible bioproducts is highly challenging due to the recalcitrant chemical structure.

Despite the recent advances in processing carbohydrate in lignocellulosics, the utilization of lignin for fungible fuels or chemicals has yet to be achieved. As a main constituent of lignocellulosic biomass (15-30% by weight, up to 40% by energy), lignin is the second most abundant biopolymer on Earth. Nevertheless, lignin has received little attention relative to cellulose in terms of R&D efforts in biofuel production. In 2004, the pulp and paper industry alone produced 50 million tons of extracted lignin, yet only approximately 2% of the lignin available from the pulp and paper industry is used commercially, with the remainder burned as a low value fuel. Nearly 300 million tons of lignin may be available if the Billion Ton initiative is implemented, and the lignin-containing biorefinery residues represent a significant resource for the sustainable production of fuels and chemicals.

From a holistic point of view, the use of lignin-containing biorefinery waste stream will add in new bioproducts to enable the integrated biorefinery. Lignocellulosic biorefineries need to develop bioproduct streams other than ethanol for both sustainability and cost-effectiveness. Lignin utilization therefore is a major factor to enable integrated biorefinery to reduce cost, minimize carbon emissions, and maximize sustainability of lignocellulosic biofuels. Lignocellulosic biomass is naturally recalcitrant to deconstruction by microorganisms and enzymes. To facilitate the enzymatic saccharification of cellulose, biomass typically requires pretreatment at elevated temperatures (i.e., ~150-220° C.) and acidic, alkaline or neutral processing conditions. Regardless of the exact bioprocessing technology employed, almost all biological processing platforms for the conversion of plant polysaccharides to bioethanol (or biobutanol) result in the formation of a significant lignin process stream. This lignin fraction can be frequently utilized as an energy resource for power/electrical generation, partially because there are few efficient chemical conversion processes available that can convert lignin into transportation biofuels or higher value chemical substrates. Although a certain amount of lignin (~30-40%) is needed for the thermal requirements of bioethanol production including pretreatment and alcohol distillation, a modern biological cellulosic processing plant will have ~60% excess lignin. The utilization of this excess lignin as feedstock for renewable fuels offers a significant opportunity to enhance the overall operational efficiency and impact of a lignocellulosic biorefinery.

Technologies being pursued to convert lignin to fungible fuels include catalytic pyrolysis, hydrotreatment, alkaline fragmentation/alkylation and gasification. Several studies have dealt with chemical treatments to fragment lignin into smaller fragments (i.e., C6 to C22) that could be used as an additive to gasoline and/or diesel. Recent reports describe a two-step method to yield a reformulated, partially oxygenated gasoline product, which includes a mixture of C6-C10 substituted phenyl/methyl ethers, cycloalkyl methyl ethers branched paraffins, and alkylated and polyalkylated cycloalkanes. Further technical requirements/challenges are still needed for this approach to achieve cost-effectiveness. Catalytic hydrotreatment of lignin has also been examined as a means of acquiring a low DP lignin for biofuels application. It has been reported that thermal treatment of softwood and hardwood lignin at 400° C. for 40 min in the presence of a metal catalyst and hydrogen resulted in 49-71% yield of a bio-oil. Pyrolysis is an alternative methodology that can convert lignin into a bio-oil. As produced, the bio-oils are very complex mixtures and are generally chemically unstable, corrosive, and have a high O:C ratio which makes their direct use for fuels problematic. Even though thermo-chemical or chemical processes provide a potentially viable approach to a lignin-to-fuel platform, these methods are often hindered by the low quality fuel product needing up-grading, corrosive intermediates or end products, and significant cost for waste management. This requires a costly hydro-deoxygenation step that is still being researched. Further technical requirements/challenges are still needed for this approach to achieve cost-effectiveness.

Lignin represents 15-30% of the dry weight of lignocellulose, and contains a higher energy content than carbohydrates. Lignin conversion is a major roadblock for the bioeconomy, largely because essentially all current bioconversion platforms lead to lignin-containing waste streams. Previous studies have reported conversion of aromatic compounds or lignin into bioproducts, although the studies were limited due to the extremely low yield of target bioproducts. In addition, previous research demonstrated the use of lignin for making carbon fiber and such material. However, the studies are limited in producing high quality product. The present invention first represents several effective ways to treat lignin and then combined with different downstream processes to produce various products. The present invention thus represents a significant advantage over current technology by providing an in-depth systems analysis and synthetic biology design for conversion of lignin to beneficial products such as polyhydroxyalkanoate (PHA), carbon fiber, asphalt binder, and lipids.

Lignin is one of the most recalcitrant biopolymers, with an aromatic compound base units cross-linked by more than ten types of stable chemical bounds. The conversion of lignin must first starts from the depolymerization of lignin. However, lignin depolymerization differs drastically from the hydrolysis for cellulose and hemiceullulose degradation. Lignin degradation involves redox reaction catalyzed by enzyme or chemicals. The key for efficient lignin conversion toward different products are the generation of redox environment to depolymerize the polymer lignin into more processible pieces. Based on this principle and motivation, the invention provides a general system and method to combine enzyme, bacterial cell, electron mediators and other chemicals in a way to promote the lignin degradation.

In particular, the invention has demonstrated that laccase and electron mediators like HBT can be combined to depolymerize lignin. The depolymerized lignin can be used to produce the bioproducts including lipid at a high titer. Traditionally, various laccase-mediator systems have been exploited to improve lignin removal in paper pulping, to degrade hazardous aromatics for environmental remediation, and to modify lignocellulosics in biorefinery pretreatment. Despite the progress, the application of a laccase-mediator system in lignin conversion and the understanding of chemical mechanisms for recalcitrant lignin depolymerization by electron mediators are both still very limited. First, even though laccase-mediator system has been used for delignification in paper pulping, the concept of using an enzyme-mediator system for solubilization of purified lignin toward bioconversion is yet to be proven. No study has established a process for lignin solubilization and conversion using an efficient laccase-mediator system. It is still unclear if development of such a process is attainable, as different electron mediators have various impacts on enzymatic oxidation of lignin, making the outcome of biological-chemical catalytic system unpredictable. Second, the molecular and chemical mechanisms for electron mediators to facilitate lignin depolymerization during the solubilization of purified lignin are yet to be revealed. Previous studies mostly exploited model compounds to illustrate how an electron mediator could facilitate the cleavage of certain chemical bonds in the model compounds. Some studies also investigated the effects of laccase-mediator system on the lignin-carbohydrate complex during the delignification of paper pulp. However, very few studies have comprehensively revealed what chemical groups the laccase-mediator system can efficiently degrade in purified lignin, which has hindered the application of such a system in lignin conversion and processing. Third, no research has established how the fragmented lignin out of laccase-mediator treatment can be integrated with microbial fermentation for bioconversion. The invention not only teaches how to use the new laccase-electron mediator system to treat lignin to produce carbon fiber and asphalt binder of quality and function, but also teaches the system and method to be combined with or implemented with engineered microorganisms as below.

Even though the lignin degradation capacity of bacteria is weaker than other organisms such as fungi, some Actinobacteria, α-Proteobacteria, and γ-Proteobacteria (including *Pseudomonas putida*) have evolved the capacity for mineralization and degradation of aromatic compounds or lignin, including lignin derivatives and toxic aromatic pollutants. Further, bacteria such as *P. putida* and *Rhodococcus opacus* have the advantage of producing or accumulating energy storage components such as lipid and PHA at high concentrations. In addition, bacterial species such as those described herein are more amenable to genetic engineering for biodesign and systems biology. Thus, in the present invention, a unique *P. putida* strain was discovered with lignin utilization capacity and exploited as a research model to elucidate the molecular mechanisms for bioconversion of lignin to bioproducts using systems biology. The integration of multiple functional modules allows for consolidated lignin bioconversion.

In another aspect, the invention provides systems and methods for enhanced degradation of lignin and increased production of lipids by utilizing *Rhodococcus opacus* bacteria in synergy with laccase, which has the capacity to self-generate radicals. Among lignin depolymerization systems, laccase is unique in that it plays critical roles in both lignin depolymerization and polymerization, thus providing more efficient lignin conversion and enabling the development of a consolidated lignin conversion mechanism. The methods described herein therefore provide environmentally useful and beneficial methods for degrading lignin and producing beneficial intermediates and compounds using genetic recombination techniques in microorganisms. In an embodiment, the methods described herein may be useful for treatment of wastewater. In an embodiment, the method can be used to produce high value proteins. As used herein, a "protein of value" or "valuable protein" or "high value protein" refers to any protein of interest that may be useful in accordance with the invention, such as a protein of commercial, pharmaceutical, agronomic, or medical interest.

As used herein, the term "bioproduct" or "biological product" refers to a product produced as a result of a biological process, such as lignin degradation or depolymerization, or from a biological material, such as a bacterial cell, plant, or a plant part. A bioproduct in accordance with the invention may include, but is not limited to, biofuel, a biofuel intermediate, a therapeutic compound, a bioplastic, a terpene, a nutraceutical compound, a terpenoid-derived compound, and a carbon containing compound. Many bioproducts have important commercial value. For example, β-caryophyllene, a major component of *Copaifera* oleoresin, can be directly used as a diesel fuel. In addition, Artemisinin is an antimalarial drug isolated from *Artemisia annua* L. Squalene recently has been shown to be an important nutraceutical and can be widely used as a vaccine carrier. Carotenoids such as lycopene, β-carotene, and astaxanthin are used as food colorants, animal feed supplements, and for nutritional and cosmetic purposes. More recently, carotenoids have received attention for their significant antioxidant activities and for their roles in inhibiting the onset of chronic diseases. PHA, PHB, and PLA are promising bioplastics. Supply of these useful compounds from natural sources is limiting and expensive, and the cost of their total synthesis is prohibitive, and thus novel methods for their production are needed.

As used herein, a lignin degradation enzyme refers to an enzyme that is capable of inducing, promoting, or participating in the degradation or depolymerization of lignin. For example, a lignin degradation enzyme may include but is not limited to a dye-decolorizing peroxidase, laccase, lignin peroxidase, manganese peroxidase, versatile peroxidase, and cellobiose dehydrogenase. In accordance with the invention, a lignin degradation enzyme may be heterologously expressed in a bacterial species described herein, or it may be endogenously expressed.

As used here in, an "electron mediator" refers to a chemical compound that can continuously be oxidized by an enzyme and subsequently reduced by the substrate. In particular, an electron mediator in accordance with the invention may refer to a chemical compound that can be oxidized by the laccase enzyme. In general, these mediators are much smaller in molecular size as compared to the laccase enzyme, allowing better penetration of redox reaction components into lignin and reaction with chemical bonds that are not accessible to laccase.

As used herein, a "module" or "functional module" refers to a construct comprising one or more genes or enzymes for performing a desired reaction in a host cell, as well as one or more promoters, signal peptides, secretion peptides, enhancers, ribosomal binding sites, or the like. In an embodiment, an effective functional module may comprise a peroxidase enzyme, a promoter, and a suitable secretion signal peptide. For example, in accordance with the invention, a lignin depolymerization module may comprise a dye peroxidase (DYP2), for example from a lignin-degrading bacterial species such as *Amycolatopsis* sp. 75iv2, a strong constitutive promoter such as the p1099 promoter from a cold-shock DNA-binding domain-containing protein, and a secretion signal peptide. In an embodiment, a secretion signal peptide may be from a Sec-pathway-dependent type II secretion system comprising a A-X-A and/or a L-A-X-G-C-X (SEQ ID NO:35) motif. In a further embodiment, such a signal peptide may include, but is not limited to, OprI, OprF, Pbp, or PelB.

As used herein, "secretion" or "protein secretion" refers to the movement of material in a cell, such as a protein, from one point to another. Secretion in bacterial cells refers to transport or translocation of proteins, enzymes, or toxins. Several protein secretion pathways have been described, including direct translocation of proteins across the plasma membrane through membrane transporters, blebbing, lysosomal secretion, and release via exosomes derived from multivesicular bodies. Proteins may also be released from cells by mechanical or physiological wounding or transient pores in the plasma membrane induced by washing cells with serum-free media or buffers. Secretion is also found in all domains of life. For example, ATP binding cassette (ABC) type transporters are found in both eukaryotic and prokaryotic organisms, the Sec system constituting the Sec Y-E-G complex is a conserved secretion system, homologous to the translocon in the eukaryotic endoplasmic reticulum and the Sec 61 translocon complex of yeast, and the twin-arginine translocation pathway (Tat) are common secretion pathways.

In another embodiment, an aromatic compound degradation module may comprise a gene encoding an enzyme from the β-ketoadipate pathway, such as an enzyme including, but not limited to VanA, VanB, or VanAB. In another embodiment, a PHA production module may comprise a gene encoding a PHA biosynthetic protein including, but not limited, to PhaC1, PhaC2, PhaJ, PhaJ4, PhaF and PhaI, and a promoter such as the Pvan promoter. Modules in accordance with the invention may be present in a single construct, such as a vector, for introduction into a host, or may be introduced into a host cell individually on more than one construct. A module or construct of the invention may also comprise a ribosomal binding site (RBS). In some embodiments, a promoter/RBS may be a native promoter/RBS, or it may be a heterologous promoter/RBS. For example, a RBS in accordance with the invention may include, but is not limited to, a RBS from TatAC, the R704 (SEQ ID NO:2) RBS from gene OPAG_00704, or the R756 RBS from gene OPAG_07756. A promoter useful in accordance with the invention may be any promoter that results in efficient expression of the gene of interest, and may include, but is not limited to, any promoter described herein, for example, P1099, $P_{VAN}$, P756, P203, P886, or the like.

A "signal peptide" in accordance with the invention may be used in combination with or synergistically with an enzyme such as laccase to produce increased lignin degradation or depolymerization. In an embodiment, such synergistic activity may also result in increased lipid production in a host cell. In one embodiment, a signal peptide may be a twin-arginine translocation (Tat) signal peptide, including, but not limited to S2587 (SEQ ID NO:1), TatA, and TatC. In an embodiment, more than one signal peptide as described herein may be used in a module for introduction into a host cell. In another embodiment, more than one signal peptide may be present in the same operon as a gene encoding an enzyme useful in accordance with the invention.

A "transporter" as used herein refers to a protein that participates in active transport of a cellular protein. In accordance with the invention, a transporter may be a major facilitator superfamily (MSF) transporter, a porin, an ABC transporter, or any transporter useful with the methods and compositions described herein. For example, a transporter useful for the present invention may be an MFS transporter or an outer membrane porin, including, but not limited to, PputA514_4268, PputA514_4696, PputA514_3332, and PputA514_1372, or an ABC transporter including, but not limited to, PputA514_5668, PputA514_1753, and PputA514_3310.

Bacterial species useful for the present invention include, but are not limited to a *Pseudomonas putida* strain, for example *P. putida* A514, a Gram positive bacterial species such as a *Rhodococcus opacus* strain. In an embodiment, the *Rhodococcus opacus* strain is *R. opacus* PD630. In another embodiment, the invention provides recombinant bacterial strains $A_{pelB\_DyP2}$ and $A_{oprI\_DyP2}$.

In a further embodiment, a bacterial cell or culture thereof in accordance with the invention may be grown in media lacking copper ions in order to avoid toxicity to the cells at high levels of heterologous expression of laccase in *R. opacus* PD630. In a further embodiment, *R. opacus* PD630 may be combined with laccase and one or more electron mediators to promote lignin depolymerization and lipid production. In another embodiment, such a combination may result in higher lignin consumption and increased lipid yield. An electron mediator in accordance with the invention may include, but is not limited to, 1-hydroxybenzotriazole (HBT), 2,2'-azino-bis-(3-ethylbenzothiazoline-6-sulfonic acid) (ABTS), acetosyringone, or phenol.

As used herein, a "bioplastic," for example PHA, refers to a compound made from agricultural byproducts such as lignin degradation or depolymerization. Bioplastics and other compounds made by similar methods may be used in the production of commodities or commodity products. Agronomically and commercially important products and/or compositions including but not limited to commodities, and by-products that are intended for use as therapeutic compounds, or for use in compositions and commodities are intended to be within the scope of the present invention. For example, lipids, therapeutic compounds, neutraceutical compounds, or other commodities and commodity products may be produced using the methods and bacterial species described herein.

An asphalt binder refers to an often water proof and thermoplastic adhesive for asphalt. Over 95% of US road pavement is done by asphalt, with a majority using hot-mix method. An asphalt binder serves as a glue to mix the asphalt together. Normally asphalt binders are produced from petroleum with an expensive process to carefully choose the crude oil type and process into a grade. Asphalt binders are normally polymers that can react well with the asphalt to improve priorities. Lignin can serve asphalt binder due to its polymer property and the water proof property. We hereby demonstrated that lignin fractions out of biological and chemical processes react well with asphalt to improve properties.

A carbon fiber refers to fibers that are composed mostly of carbon atoms. Carbon atoms need to be bonded together in crystals to produce the carbon fiber of quality. In particular, the carbon molecules need to be bundled together to form a row or a crystal alignment. Lignin carbon fiber has been proposed before, however, most of the previous study use lignin to simply mix with PAN to produce fiber, or use a certain type of lignin like C-lignin, which is not commonly existed. We hereby showed that the treatment of lignin with Laccase-Mediator system makes lignin much better to be processed into carbon fibers, which is most likely due to the more uniform chemical bonds after treatment, and therefore making it easier to achieve crystallinity.

DNA Molecules

As used herein, the term "DNA" or "DNA molecule" refers to a double-stranded DNA molecule of genomic or synthetic origin, i.e. a polymer of deoxyribonucleotide bases or a polynucleotide molecule, read from the 5' (upstream) end to the 3' (downstream) end. As used herein, the term "DNA sequence" refers to the nucleotide sequence of a DNA molecule. The nomenclature used herein corresponds to that of Title 37 of the United States Code of Federal Regulations § 1.822, and set forth in the tables in WIPO Standard ST.25 (1998), Appendix 2, Tables 1 and 3.

As used herein, the term "isolated DNA molecule" refers to a DNA molecule at least partially separated from other molecules normally associated with it in its native or natural state. In one embodiment, the term "isolated" refers to a DNA molecule that is at least partially separated from some of the nucleic acids that normally flank the DNA molecule in its native or natural state. Thus, DNA molecules fused to regulatory or coding sequences with which they are not normally associated, for example as the result of recombinant techniques, are considered isolated herein. Such molecules are considered isolated when integrated into the chromosome of a host cell or present in a nucleic acid solution with other DNA molecules, in that they are not in their native state.

Any number of methods well known to those skilled in the art can be used to isolate and manipulate a DNA molecule, or fragment thereof, as disclosed in the present invention. For example, polymerase chain reaction (PCR) technology can be used to amplify a particular starting DNA molecule and/or to produce variants of the original molecule. DNA molecules, or fragment thereof, can also be obtained by other techniques, such as by directly synthesizing the fragment by chemical means, as is commonly practiced by using an automated oligonucleotide synthesizer.

Regulatory Elements

A regulatory element is a DNA molecule having gene regulatory activity, i.e. one that has the ability to affect the transcription and/or translation of an operably linked transcribable polynucleotide molecule. Regulatory elements in accordance with the present invention may be any regulatory element useful for degradation or depolymerization of lignin, and production of compounds such as aromatic compounds, lipids, PHA, or therapeutic compounds. The term "gene regulatory activity" thus refers to the ability to affect the expression pattern of an operably linked transcribable polynucleotide molecule by affecting the transcription and/or translation of that operably linked transcribable polynucleotide molecule. As used herein, a transcriptional regulatory expression element group may be comprised of expression elements, such as enhancers, promoters, leaders, and introns, operably linked. A promoter may include a ribosomal binding site, which may be heterologous or naturally occurring. Thus, a transcriptional regulatory expression element group may be comprised, for instance, of a promoter operably linked 5' to a leader sequence, which is in turn operably linked 5' to an intron sequence. The intron sequence may be comprised of a sequence beginning at the point of the first intron/exon splice junction of the native sequence and may be further comprised of a small leader fragment comprising the second intron/exon splice junction so as to provide for proper intron/exon processing to facilitate transcription and proper processing of the resulting transcript. Leaders and introns may positively affect transcription of an operably linked transcribable polynucleotide molecule, as well as translation of the resulting transcribed RNA. The pre-processed RNA molecule comprises leaders and introns, which may affect the post-transcriptional processing of the transcribed RNA and/or the export of the transcribed RNA molecule from the cell nucleus into the cytoplasm. Following post-transcriptional processing of the transcribed RNA molecule, the leader sequence may be retained as part of the final messenger RNA and may positively affect the translation of the messenger RNA molecule.

Regulatory elements such as promoters, leaders, introns, and transcription termination regions are DNA molecules that have gene regulatory activity and play an integral part in the overall expression of genes in living cells. Isolated regulatory elements, such as promoters and leaders, that function in host cells are therefore useful for modifying host cell phenotypes through the methods of genetic engineering.

Regulatory elements may be characterized by their expression pattern effects (qualitatively and/or quantitatively), e.g. positive or negative effects and/or constitutive or other effects, such as by their temporal, spatial, developmental, tissue, environmental, physiological, pathological, cell cycle, and/or chemically responsive expression pattern, and any combination thereof, as well as by quantitative or qualitative indications. A promoter may be useful as a regulatory element for modulating the expression of an operably linked transcribable polynucleotide molecule.

As used herein, a "gene expression pattern" is any pattern of transcription of an operably linked DNA molecule into a transcribed RNA molecule. The transcribed RNA molecule may be translated to produce a protein molecule or may provide an antisense or other regulatory RNA molecule, such as an mRNA, a dsRNA, a tRNA, an rRNA, a miRNA, and the like.

As used herein, the term "protein expression" is any pattern of translation of a transcribed RNA molecule into a protein molecule. Protein expression may be characterized by its temporal, spatial, developmental, or morphological qualities, as well as by quantitative or qualitative indications.

As used herein, the term "promoter" refers generally to a DNA molecule that is involved in recognition and binding of RNA polymerase II and other proteins (trans-acting transcription factors) to initiate transcription. A promoter may be initially isolated from the 5' untranslated region (5' UTR) of a genomic copy of a gene. Alternately, promoters may be synthetically produced or manipulated DNA molecules. Promoters may also be chimeric, i.e. a promoter produced through the fusion of two or more heterologous DNA molecules. In specific embodiments of the invention, such molecules and any variants or derivatives thereof as described herein are further defined as comprising promoter activity, i.e., are capable of acting as a promoter in a host cell, such as in a transgenic bacterial cell or transgenic plant. In still further specific embodiments, a fragment may be defined as exhibiting promoter activity possessed by the starting promoter molecule from which it is derived, or a fragment may comprise a "minimal promoter" that provides a basal level of transcription and is comprised of a TATA box or equivalent sequence for recognition and binding of the RNA polymerase II complex for initiation of transcription.

Compositions derived from a promoter useful for the present invention, such as internal or 5' deletions, for example, can be produced using methods known in the art to improve or alter expression, including by removing elements that have either positive or negative effects on expression; duplicating elements that have positive or negative effects on expression; and/or duplicating or removing elements that have tissue- or cell-specific effects on expression. Further deletions can be made to remove any elements that have positive or negative; tissue specific; cell specific; or timing specific (such as, but not limited to, circadian rhythms) effects on expression. The efficacy of the modifications, duplications or deletions described herein on the desired expression aspects of a particular transgene may be tested empirically in stable and transient assays, such as those described in the working examples herein, so as to validate the results, which may vary depending upon the changes made and the goal of the change in the starting molecule.

As used herein, the term "leader" refers to a DNA molecule isolated from the untranslated 5' region (5' UTR) of a genomic copy of a gene and defined generally as a nucleotide segment between the transcription start site (TSS) and the protein coding sequence start site. Alternately, leaders may be synthetically produced or manipulated DNA elements. A leader can be used as a 5' regulatory element for modulating expression of an operably linked transcribable polynucleotide molecule. Leader molecules may be used with a heterologous promoter or with their native promoter. Promoter molecules of the present invention may thus be operably linked to their native leader or may be operably linked to a heterologous leader. In specific embodiments, such sequences may be provided defined as being capable of acting as a leader in a host cell, including, for example, a transgenic bacterial cell. In one embodiment, such sequences are decoded as comprising leader activity.

A leader sequence (5' UTR) in accordance with the present invention may be comprised of regulatory elements or may adopt secondary structures that can have an effect on transcription or translation of a transgene. Such a leader sequence may be used in accordance with the present invention to make chimeric regulatory elements that affect transcription or translation of a transgene. In addition, such a leader sequence may be used to make chimeric leader sequences that affect transcription or translation of a transgene.

The introduction of a foreign gene into a new bacterial, fungal, or plant host does not always result in high expression of the incoming gene. Furthermore, if dealing with complex traits, it is sometimes necessary to modulate several genes with spatially or temporally different expression patterns. Introns can principally provide such modulation. However, multiple uses of the same intron in one host cell has been shown to exhibit disadvantages. In those cases, it is necessary to have a collection of basic control elements for the construction of appropriate recombinant DNA elements. The number of introns known in the art to have expression-enhancing properties is limited, and thus, alternatives are needed.

In accordance with the present invention, a promoter or promoter fragment may be analyzed for the presence of known promoter elements, i.e. DNA sequence characteristics, such as a TATA-box and other known transcription factor binding site motifs. Identification of such known promoter elements may be used by one of skill in the art to design variants of a promoter having a similar expression pattern to the original promoter.

As used herein, the term "enhancer" or "enhancer element" refers to a cis-acting transcriptional regulatory element (a cis-element), which confers an aspect of the overall expression pattern, but is usually insufficient alone to drive transcription of an operably linked polynucleotide sequence. Unlike promoters, enhancer elements do not usually include a transcription start site (TSS), or TATA box or equivalent sequence. A promoter may naturally comprise one or more enhancer elements that affect the transcription of an operably linked polynucleotide sequence. An isolated enhancer element may also be fused to a promoter to produce a chimeric promoter cis-element, which confers an aspect of the overall modulation of gene expression. A promoter or promoter fragment may comprise one or more enhancer elements that affect the transcription of operably linked genes. Many promoter enhancer elements are believed to bind DNA-binding proteins and/or affect DNA topology, producing local conformations that selectively allow or restrict access of RNA polymerase to the DNA template, or that facilitate selective opening of the double helix at the site of transcriptional initiation. An enhancer element may function to bind transcription factors that regulate transcription. Some enhancer elements bind more than one transcription factor, and transcription factors may interact with different affinities with more than one enhancer domain. Enhancer elements can be identified by a number of techniques, including deletion analysis, i.e. deleting one or more nucleotides from the 5' end or internal to a promoter; DNA binding protein analysis using DNase I footprinting, methylation interference, electrophoresis mobility-shift assays, in vivo genomic footprinting by ligation-mediated PCR, and other conventional assays; or by DNA sequence similarity analysis using known cis-element motifs or enhancer elements as a target sequence or target motif with conventional DNA sequence comparison methods, such as BLAST. The fine structure of an enhancer domain can be further studied by mutagenesis (or substitution) of one or more nucleotides or by other conventional methods. Enhancer elements can be obtained by chemical synthesis or by isolation from regulatory elements that include such elements, and they can be synthesized with additional flanking nucleotides that contain useful restriction enzyme sites to facilitate subsequence manipulation. Thus, the design, construction, and use of enhancer elements according to the methods disclosed herein for modulating the expression of operably linked transcribable polynucleotide molecules are encompassed by the present invention.

In plants, the inclusion of some introns in gene constructs leads to increased mRNA and protein accumulation relative to constructs lacking the intron. This effect has been termed "intron mediated enhancement" (IME) of gene expression (Mascarenhas et al., (1990) *Plant Mol. Biol.* 15:913-920). Introns known to stimulate expression in plants have been identified in maize genes [e.g., tubA1, Adh1, Sh1, Ubi1 (Jeon et al., *Plant Physiol.* 123:1005-1014, 2000; Callis et al., *Genes Dev.* 1:1183-1200, 1987; Vasil et al., *Plant Physiol.* 91:1575-1579, 1989; Christiansen et al., *Plant Mol. Biol.* 18:675-689, 1992) and in rice genes (e.g., salt, tpi: McElroy et al., *Plant Cell* 2:163-171, 1990; Xu et al., *Plant Physiol.* 106:459-467, 1994). Similarly, introns from dicotyledonous plant genes such as *petunia* (e.g., rbcS), potato (e.g., st-ls1) and *Arabidopsis thaliana* (e.g., ubq3 and pat1) have been found to elevate gene expression rates (Dean et al., *Plant Cell* 1:201-208, 1989; Leon et al., *Plant Physiol.* 95:968-972, 1991; Norris et al., *Plant Mol Biol.* 21:895-906, 1993; Rose and Last, *Plant J.* 11:455-464, 1997). It has been shown that deletions or mutations within the splice sites of an intron reduce gene expression, indicating that splicing might be needed for IME (Mascarenhas et al., *Plant Mol Biol.* 15:913-920, 1990; Clancy and Hannah, *Plant Physiol.* 130:918-929, 2002). However, such splicing is not required for a certain IME in dicotyledonous plants, as shown by point mutations within the splice sites of the pat1 gene from *A. thaliana* (Rose and Beliakoff, *Plant Physiol.* 122:535-542, 2000).

Enhancement of gene expression by introns is not a general phenomenon because some intron insertions into recombinant expression cassettes fail to enhance expression (e.g., introns from dicot genes such as the rbcS gene from pea, the phaseolin gene from bean, and the stls-1 gene from *Solanum tuberosum*) and introns from maize genes (the ninth intron of the adh1 gene, and the first intron of the hsp81 gene) (Chee et al., *Gene* 41:47-57, 1986; Kuhlemeier et al., *Mol Gen Genet* 212:405-411, 1988; Mascarenhas et al., *Plant Mol. Biol.* 15:913-920, 1990; *Sinibaldi and Mettler, In W E Cohn, K Moldave, eds, Progress in Nucleic Acid Research and Molecular Biology, Vol* 42. *Academic Press*, New York, pp 229-257, 1992; Vancanneyt et al., *Mol. Gen. Genet.* 220:245-250, 1990). Therefore, not every intron can be employed to manipulate the gene expression level of non-endogenous genes or endogenous genes in transgenic plants. What characteristics or specific sequence features must be present in an intron sequence in order to enhance the expression rate of a given gene is not known in the art, and therefore it is not possible to predict whether a given plant intron, when used heterologously, will cause IME.

As used herein, the term "chimeric" refers to a single DNA molecule produced by fusing a first DNA molecule to a second DNA molecule, where neither the first nor the second DNA molecule would normally be found in that configuration, i.e. fused to the other. The chimeric DNA molecule is thus a new DNA molecule not otherwise normally found in nature. As used herein, the term "chimeric promoter" refers to a promoter produced through such manipulation of DNA molecules. A chimeric promoter may combine two or more DNA fragments, for example the fusion of a promoter to an enhancer element. Thus, the design, construction, and use of chimeric promoters according to the methods disclosed herein for modulating the expression of operably linked transcribable polynucleotide molecules are encompassed by the present invention.

As used herein, the term "variant" refers to a second DNA molecule that is similar in composition, but not identical to, a first DNA molecule, and yet the second DNA molecule still maintains the general functionality, i.e. same or similar expression pattern, of the first DNA molecule. A variant may be a shorter or truncated version of the first DNA molecule and/or an altered version of the sequence of the first DNA molecule, such as one with different restriction enzyme sites and/or internal deletions, substitutions, and/or insertions. A "variant" may also encompass a regulatory element having a nucleotide sequence comprising a substitution, deletion, and/or insertion of one or more nucleotides of a reference sequence, wherein the derivative regulatory element has more or less or equivalent transcriptional or translational activity than the corresponding parent regulatory molecule. The regulatory element "variants" will also encompass variants arising from mutations that naturally occur in bacterial, fungal, and plant cell transformation. In the present invention, a polynucleotide sequence may be used to create variants that are similar in composition, but not identical to, the polynucleotide sequence of the original regulatory element, while still maintaining the general functionality, i.e. same or similar expression pattern, of the original regulatory element. Production of such variants of the present invention is well within the ordinary skill of the art in light of the disclosure and is encompassed within the scope of the present invention. Chimeric regulatory element "variants" comprise the same constituent elements as a reference sequence, but the constituent elements comprising the chimeric regulatory element may be operatively linked by various methods known in the art, such as restriction enzyme digestion and ligation, ligation independent cloning, modular assembly of PCR products during amplification, or direct chemical synthesis of the regulatory element, as well as other methods known in the art. The resulting chimeric regulatory element "variant" can be comprised of the same, or variants of the same, constituent elements of the reference sequence but differ in the sequence or sequences that comprise the linking sequence or sequences which allow the constituent parts to be operatively linked.

Constructs

As used herein, the term "construct" refers to any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule, where one or more polynucleotide molecules has been linked in a functionally operative manner, i.e. operably linked. As used herein, the term "vector" means any recombinant polynucleotide construct that may be used for the purpose of transformation, i.e. the introduction of heterologous DNA into a host cell. A vector according to the present invention may include an expression cassette or transgene cassette isolated from any of the aforementioned molecules. In an embodiment, a vector in accordance with the invention may comprise more than one expression cassette or module comprising a desired polynucleotide molecule.

As used herein, the term "operably linked" refers to a first molecule joined to a second molecule, wherein the molecules are so arranged that the first molecule affects the function of the second molecule. The two molecules may or may not be part of a single contiguous molecule and may or may not be adjacent. For example, a promoter is operably linked to a transcribable polynucleotide molecule if the promoter modulates transcription of the transcribable polynucleotide molecule of interest in a cell. A leader, for example, is operably linked to coding sequence when it is capable of serving as a leader for the polypeptide encoded by the coding sequence.

Constructs of the present invention may be provided, in one embodiment, as double Ti plasmid border DNA constructs that have right border (RB or AGRtu.RB) and left border (LB or AGRtu.LB) regions of the Ti plasmid isolated from *Agrobacterium tumefaciens* comprising a T-DNA, that along with transfer molecules provided by the *A. tumefaciens* cells that permit the integration of the T-DNA into the genome of a host cell (see, for example, U.S. Pat. No. 6,603,061). The constructs may also contain the plasmid backbone DNA segments that provide replication function and antibiotic selection in bacterial cells, for example, an *Escherichia coli* origin of replication such as ori322, a broad host range origin of replication such as oriV or oriRi, and a coding region for a selectable marker such as Spec/Strp that encodes a Tn7 aminoglycoside adenyltransferase (aadA) conferring resistance to spectinomycin or streptomycin, or a gentamicin (Gm, Gent) selectable marker gene. For plant transformation, the host bacterial strain is often *A. tumefaciens* ABI, C58, or LBA4404; however, other strains known to those skilled in the art of transformation can function in the present invention.

Methods are known in the art for assembling and introducing constructs into a cell in such a manner that the transcribable polynucleotide molecule is transcribed into a functional mRNA molecule that is translated and expressed as a protein product. For the practice of the present invention, conventional compositions and methods for preparing and using constructs and host cells are well known to one skilled in the art (see, for example, Molecular Cloning: A Laboratory Manual, 3rd edition Volumes 1, 2, and 3, J. Sambrook, D. W. Russell, and N. Irwin, Cold Spring Harbor Laboratory Press, 2000). Methods for making recombinant vectors particularly suited to bacterial, fungal, or plant transformation are well known in the art. These types of vectors have also been reviewed in the scientific literature (see, for example, Rodriguez, et al., Vectors: A Survey of Molecular Cloning Vectors and Their Uses, Butterworths, Boston, 1988; and Glick et al., Methods in Plant Molecular Biology and Biotechnology, CRC Press, Boca Raton, Fla., 1993). Typical vectors useful for expression of nucleic acids in bacteria, fungi, and plants are well known in the art and may include, for example, plasmid pPROBE-GT, and vectors derived from the tumor-inducing (Ti) plasmid of *A. tumefaciens* (Rogers et al., Methods in Enzymology 153: 253-277, 1987). Other recombinant vectors useful for bacterial, fungal, or plant transformation are well known in the art.

Various regulatory elements may be included in a construct, including any of those provided herein. Any such regulatory elements may be provided in combination with other regulatory elements. Such combinations can be designed or modified to produce desirable regulatory features. In one embodiment, constructs of the present invention comprise at least one regulatory element operably linked to a transcribable polynucleotide molecule operably linked to a 3' transcription termination molecule.

Constructs of the present invention may include any promoter or leader provided herein or known in the art. For example, a promoter of the present invention may be operably linked to a heterologous non-translated 5' leader such as one derived from a heat shock protein gene (see, for example, U.S. Pat. Nos. 5,659,122 and 5,362,865). Alternatively, a leader of the present invention may be operably linked to a heterologous promoter such as the Cauliflower Mosaic Virus (CaMV) 35S transcript promoter (see, for example, U.S. Pat. No. 5,352,605).

As used herein, the term "intron" refers to a DNA molecule that may be isolated or identified from the genomic copy of a gene and may be defined generally as a region spliced out during mRNA processing prior to translation. Alternately, an intron may be a synthetically produced or manipulated DNA element. An intron may contain enhancer elements that effect the transcription of operably linked genes. An intron may be used as a regulatory element for modulating expression of an operably linked transcribable polynucleotide molecule. A DNA construct may comprise an intron, and the intron may or may not be heterologous with respect to the transcribable polynucleotide molecule sequence. Examples of introns in the art include the rice actin intron (U.S. Pat. No. 5,641,876) and the corn HSP70 intron (U.S. Pat. No. 5,859,347). Further, when modifying intron/exon boundary sequences, it may be preferable to avoid using the nucleotide sequence AT or the nucleotide A just prior to the 5' end of the splice site (GT) and the nucleotide G or the nucleotide sequence TG, respectively, immediately after 3' end of the splice site (AG) to eliminate the potential of unwanted start codons formed during processing of the messenger RNA into the final transcript. The sequence around the 5' or 3' end splice junction sites of the intron can thus be modified in this manner.

As used herein, the term "3' transcription termination molecule" or "3' UTR" refers to a DNA molecule that is used during transcription to produce the 3' untranslated region (3' UTR) of an mRNA molecule. The 3' untranslated region of an mRNA molecule may be generated by specific cleavage and 3' polyadenylation (polyA tail). A 3' UTR may be operably linked to and located downstream of a transcribable polynucleotide molecule and may include polynucleotides that provide a polyadenylation signal and other regulatory signals capable of affecting transcription, mRNA processing, or gene expression. PolyA tails are thought to function in mRNA stability and in initiation of translation. Examples of 3' transcription termination molecules in the art are the nopaline synthase 3' region (see, Fraley, et al., Proc. Natl. Acad. Sci. USA, 80: 4803-4807, 1983); wheat hsp17 3' region; pea rubisco small subunit 3' region; cotton E6 3' region (U.S. Pat. No. 6,096,950); 3' regions disclosed in WO/0011200 A2; and the coixin 3' UTR (U.S. Pat. No. 6,635,806).

3' UTRs typically find beneficial use for the recombinant expression of specific genes. In animal systems, machinery of 3' UTRs has been well defined (e.g., Zhao et al., *Microbiol Mol Biol Rev* 63:405-445, 1999; Proudfoot, *Nature* 322:562-565, 1986; Kim et al., *Biotechnology Progress* 19:1620-1622, 2003; Yonaha and Proudfoot, *EMBO J.* 19:3770-3777, 2000; Cramer et al., *FEBS Letters* 498:179-182, 2001; Kuerstem and Goodwin, *Nature Reviews Genetics* 4:626-637, 2003). Effective termination of RNA transcription is required to prevent unwanted transcription of trait-unrelated (downstream) sequences, which may interfere with trait performance. Arrangement of multiple gene expression cassettes in local proximity to one another (e.g. within one T-DNA) may cause suppression of gene expression of one or more genes in said construct in comparison to independent insertions (Padidam and Cao, *BioTechniques* 31:328-334, 2001). This may interfere with achieving adequate levels of expression, for instance in cases where strong gene expression from all cassettes is desired.

In plants, for example, clearly defined polyadenylation signal sequences are not known. Hasegawa et al. (*Plant J.* 33:1063-1072, 2003) were not able to identify conserved polyadenylation signal sequences in both in vitro and in vivo systems in *Nicotiana sylvestris* and to determine the actual length of the primary (non-polyadenylated) transcript. A weak 3' UTR may generate read-through, which may affect the expression of the genes located in neighboring expression cassettes (Padidam and Cao, *BioTechniques* 31:328-334, 2001). Appropriate control of transcription termination can prevent read-through into sequences (e.g., other expression cassettes) localized downstream and can further allow efficient recycling of RNA polymerase to improve gene expression. Efficient termination of transcription (release of RNA Polymerase II from the DNA) is prerequisite for re-initiation of transcription and thereby directly affects the overall transcript level. Subsequent to transcription termination, the mature mRNA is released from the site of synthesis and template to the cytoplasm. Eukaryotic mRNAs are accumulated as poly(A) forms in vivo, making it difficult to detect transcriptional termination sites by conventional methods. However, prediction of functional and efficient 3' UTRs by bioinformatics methods is difficult in that there are no conserved sequences to enable easy prediction of an effective 3' UTR.

From a practical standpoint, it may be beneficial that a 3' UTR used in a transgene cassette possesses certain characteristics. For example, a 3' UTR useful in accordance with the present invention may efficiently and effectively terminate transcription of the transgene and prevent read-through of the transcript into any neighboring DNA sequence, which can be comprised of another transgene cassette, as in the case of multiple cassettes residing in one T-DNA, or the neighboring chromosomal DNA into which the T-DNA has inserted. The 3' UTR optimally should not cause a reduction in the transcriptional activity imparted by the promoter, leader, and introns that are used to drive expression of the transgene. In biotechnology, the 3' UTR is often used for priming of amplification reactions of reverse-transcribed RNA extracted from the transformed host and may be used to (1) assess the transcriptional activity or expression of the transgene cassette once integrated into the host genome; (2) assess the copy number of insertions within the host DNA; and (3) assess zygosity of the resulting progeny where appropriate. The 3' UTR may also be used in amplification reactions of DNA extracted from the transformed host to characterize the intactness of the inserted cassette.

3' UTRs useful in providing expression of a transgene in a host may be identified based upon the expression of expressed sequence tags (ESTs) in cDNA libraries made from messenger RNA isolated from seed, flower, or any other tissues derived from, for example, Big bluestem (*Andropogon gerardii*), Plume Grass [*Saccharum ravennae* (*Erianthus ravennae*)], Green bristlegrass (*Setaria viridis*), Teosinte (*Zea mays* subsp. *mexicana*), Foxtail millet (*Setaria italica*), Coix (*Coix lacryma-jobi*) among others. Using methods known to those skilled in the art, libraries of genetic material such as cDNA may be made from host cells or tissues isolated from a host species. The resulting cDNAs are sequenced using various sequencing methods known in the art. The resulting ESTs are assembled into clusters using bioinformatics software such as cic_ref_assemble_complete version 2.01.37139 (CLC bio USA, Cambridge, Mass. 02142). Transcript abundance of each cluster is determined by counting the number of cDNA reads for each cluster. The identified 3' UTRs may be comprised of sequence derived from cDNA sequence, as well as sequence derived from genomic DNA. A cDNA sequence may be used to design primers, which may then be used with GenomeWalker™ (Clontech Laboratories, Inc, Mountain View, Calif.) libraries constructed following the manufacturer's protocol to clone the 3' region of the corresponding genomic DNA sequence to provide a longer termination sequence. Analysis of relative transcript abundance either by direct counts or normalized counts of observed sequence reads for each tissue library may be used to infer properties about patters of expression. For example, some 3' UTRs may be found in transcripts more abundant in root tissue rather than leaf tissue. This suggests that the transcript is highly expressed in root and that the properties of root expression may be attributable to the transcriptional regulation of the promoter, the leader, the introns, or the 3' UTR. Empirical testing of 3' UTRs identified by the properties of expression within specific organs, tissues, or cell types can result in the identification of 3' UTRs that enhance expression in those specific organs, tissues, or cell types.

Constructs and vectors may also include transit peptide or secretion signal peptide coding sequences that express a linked peptide useful for targeting of a protein product, particularly to a chloroplast, leucoplast, or other plastid organelle; mitochondria; peroxisome; vacuole; or an extracellular location. For descriptions of the use of chloroplast transit peptides, see U.S. Pat. Nos. 5,188,642 and 5,728,925. Many chloroplast-localized proteins are expressed from nuclear genes as precursors and are targeted to the chloroplast by a chloroplast transit peptide (CTP). Examples of such isolated chloroplast proteins include, but are not limited to, those associated with the small subunit (SSU) of ribulose-1,5-bisphosphate carboxylase, ferredoxin, ferredoxin oxidoreductase, the light-harvesting complex protein I and protein II, thioredoxin F, enolpyruvyl shikimate phosphate synthase (EPSPS), and transit peptides described in U.S. Pat. No. 7,193,133. It has been demonstrated in vivo and in vitro, for example, that non-chloroplast proteins may be targeted to the chloroplast by use of protein fusions with a heterologous CTP and that the CTP is sufficient to target a protein to the chloroplast.

Transcribable Polynucleotide Molecules

As used herein, the term "transcribable polynucleotide molecule" refers to any DNA molecule capable of being transcribed into an RNA molecule, including, but not limited to, those having protein coding sequences and those producing RNA molecules having sequences useful for gene suppression. A "transgene" refers to a transcribable polynucleotide molecule heterologous to a host cell at least with respect to its location in the genome and/or a transcribable polynucleotide molecule artificially incorporated into a host cell's genome in the current or any prior generation of the cell.

A promoter of the present invention may be operably linked to a transcribable polynucleotide molecule that is heterologous with respect to the promoter molecule. As used herein, the term "heterologous" refers to the combination of two or more polynucleotide molecules when such a combination is not normally found in nature. For example, the two molecules may be derived from different species and/or the two molecules may be derived from different genes, e.g., different genes from the same species, or the same genes from different species. A promoter is thus heterologous with respect to an operably linked transcribable polynucleotide molecule if such a combination is not normally found in nature, i.e. that transcribable polynucleotide molecule is not naturally occurring operably linked in combination with that promoter molecule.

The transcribable polynucleotide molecule may generally be any DNA molecule for which expression of a RNA transcript is desired. Such expression of an RNA transcript may result in translation of the resulting mRNA molecule and thus protein expression. Alternatively, for example, a transcribable polynucleotide molecule may be designed to ultimately cause decreased expression of a specific gene or protein. In one embodiment, this may be accomplished by using a transcribable polynucleotide molecule that is oriented in the antisense direction. One of ordinary skill in the art is familiar with using such antisense technology. Briefly, as the antisense transcribable polynucleotide molecule is transcribed, the RNA product hybridizes to and sequesters a complimentary RNA molecule inside the cell. This duplex RNA molecule cannot be translated into a protein by the cell's translational machinery and is degraded in the cell. Any gene may be negatively regulated in this manner.

Thus, in one embodiment of the present invention, a regulatory element may be operably linked to a transcribable polynucleotide molecule in order to modulate transcription of the transcribable polynucleotide molecule at a desired level or in a desired pattern when the construct is integrated in the genome of a host cell. In one embodiment, the transcribable polynucleotide molecule comprises a protein-coding region of a gene, and the promoter affects the transcription of an RNA molecule that is translated and expressed as a protein product. In another embodiment, the transcribable polynucleotide molecule comprises an antisense region of a gene, and the promoter affects the transcription of an antisense RNA molecule, double-stranded RNA or other similar inhibitory RNA molecule in order to inhibit expression of a specific RNA molecule of interest in a target host cell.

Genes of Agronomic Interest

Transcribable polynucleotide molecules in accordance with the present invention may be genes of agronomic interest. As used herein, the term "gene of agronomic interest" refers to a transcribable polynucleotide molecule that, when expressed in a particular host cell, or cell type, confers a desirable characteristic, such as one associated with morphology, physiology, growth, development, product, pest resistance, and/or environmental or chemical tolerance. Genes of agronomic interest include, but are not limited to, those encoding a yield protein, a stress resistance protein, a developmental control protein, an environmentally responsive protein, a senescence protein, a hormone responsive protein, a fatty acid biosynthetic enzyme, an amino acid biosynthetic enzyme, or any other agent, such as an antisense or RNAi molecule targeting a particular gene for suppression. The product of a gene of agronomic interest may act within the host in order to cause an effect upon the cell physiology or metabolism, for example lignin degradation or depolymerization and/or production of compounds such as laccase, lignin, or a therapeutic compound.

In one embodiment of the present invention, a promoter is incorporated into a construct such that the promoter is operably linked to a transcribable polynucleotide molecule that is a gene of agronomic interest. The expression of the gene of agronomic interest is desirable in order to confer an agronomically beneficial trait. Without limitation, a beneficial agronomic trait may include, for example, modified lignin content, fungal disease resistance, virus resistance, nematode resistance, bacterial disease resistance, starch production, modified oil production, high oil production, modified fatty acid or lipid content, high protein production, biopolymers, environmental stress resistance, pharmaceutical peptides, secretable peptides, improved processing traits, improved digestibility, enzyme production, flavor, nitrogen fixation, fiber production, and biofuel production, among others. Examples of genes of agronomic interest known in the art include those for herbicide resistance (U.S. Pat. Nos. 6,803,501; 6,448,476; 6,248,876; 6,225,114; 6,107,549; 5,866,775; 5,804,425; 5,633,435; and 5,463,175), increased yield (U.S. Pat. Nos. RE38,446; 6,716,474; 6,663,906; 6,476,295; 6,441,277; 6,423,828; 6,399,330; 6,372,211; 6,235,971; 6,222,098; and 5,716,837), insect control (U.S. Pat. Nos. 6,809,078; 6,713,063; 6,686,452; 6,657,046; 6,645,497; 6,642,030; 6,639,054; 6,620,988; 6,593,293; 6,555,655; 6,538,109; 6,537,756; 6,521,442; 6,501,009; 6,468,523; 6,326,351; 6,313,378; 6,284,949; 6,281,016; 6,248,536; 6,242,241; 6,221,649; 6,177,615; 6,156,573; 6,153,814; 6,110,464; 6,093,695; 6,063,756; 6,063,597; 6,023,013; 5,959,091; 5,942,664; 5,942,658; 5,880,275; 5,763,245; and 5,763,241), fungal disease resistance (U.S. Pat. Nos. 6,653,280; 6,573,361; 6,506,962; 6,316,407; 6,215,048; 5,516,671; 5,773,696; 6,121,436; 6,316,407; and 6,506,962), virus resistance (U.S. Pat. Nos. 6,617,496; 6,608,241; 6,015,940; 6,013,864; 5,850,023; and 5,304,730), nematode resistance (U.S. Pat. No. 6,228,992), bacterial disease resistance (U.S. Pat. No. 5,516,671), plant growth and development (U.S. Pat. Nos. 6,723,897 and 6,518,488), starch production (U.S. Pat. Nos. 6,538,181; 6,538,179; 6,538,178; 5,750,876; and 6,476,295), modified oil production (U.S. Pat. Nos. 6,444,876; 6,426,447; and 6,380,462), high oil production (U.S. Pat. Nos. 6,495,739; 5,608,149; 6,483,008; and 6,476,295), modified fatty acid content (U.S. Pat. Nos. 6,828,475; 6,822,141; 6,770,465; 6,706,950; 6,660,849; 6,596,538; 6,589,767; 6,537,750; 6,489,461; and 6,459,018), high protein production (U.S. Pat. No. 6,380,466), fruit ripening (U.S. Pat. No. 5,512,466), enhanced animal and human nutrition (U.S. Pat. Nos. 6,723,837; 6,653,530; 6,541,259; 5,985,605; and 6,171,640), biopolymers (U.S. Pat. Nos. RE37,543; 6,228,623; 5,958,745; and 6,946,588), environmental stress resistance (U.S. Pat. No. 6,072,103), pharmaceutical peptides and secretable peptides (U.S. Pat. Nos. 6,812,379; 6,774,283; 6,140,075; and 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), fiber production (U.S. Pat. Nos. 6,576,818; 6,271,443; 5,981,834; and 5,869,720) and biofuel production (U.S. Pat. No. 5,998,700).

Alternatively, a gene of agronomic interest can affect an above mentioned characteristic or phenotype by encoding an RNA molecule that causes the targeted modulation of gene expression of an endogenous gene, for example via antisense (see for example, U.S. Pat. No. 5,107,065); inhibitory RNA ("RNAi," including modulation of gene expression via mechanisms mediated by miRNA, siRNA, trans-acting siRNA, and phased sRNA, e.g. as described in published applications US 2006/0200878 and US 2008/0066206, and in U.S. patent application Ser. No. 11/974,469); or cosuppression-mediated mechanisms. The RNA may also be a catalytic RNA molecule (e.g. a ribozyme or a riboswitch; see e.g. US 2006/0200878) engineered to cleave a desired endogenous mRNA product. Thus, any transcribable polynucleotide molecule that encodes a transcribed RNA molecule that affects an agronomically important phenotype or morphology change of interest may be useful for the practice of the present invention. Methods are known in the art for constructing and introducing constructs into a cell in such a manner that the transcribable polynucleotide molecule is transcribed into a molecule that is capable of causing gene suppression. For example, posttranscriptional gene suppression using a construct with an anti-sense oriented transcribable polynucleotide molecule to regulate gene expression in host cells is disclosed in U.S. Pat. Nos. 5,107,065 and 5,759,829, and posttranscriptional gene suppression using a construct with a sense-oriented transcribable polynucleotide molecule to regulate gene expression in a plant host cell is disclosed in U.S. Pat. Nos. 5,283,184 and 5,231,020. Exemplary transcribable polynucleotide molecules for incorporation into constructs of the present invention include, for example, DNA molecules or genes from a species other than the target species or genes that originate with or are present in the same species, but are incorporated into recipient cells by genetic engineering methods rather than classical reproduction or breeding techniques. The type of polynucleotide molecule may include, but is not limited to, a polynucleotide molecule that is already present in the host cell or species, a polynucleotide molecule from another host cell or species, a polynucleotide molecule from a different organism, or a polynucleotide molecule generated externally, such as a polynucleotide molecule containing an antisense message of a gene, or a polynucleotide molecule encoding an artificial, synthetic, or otherwise modified version of a transgene.

Selectable Markers

As used herein the term "marker" refers to any transcribable polynucleotide molecule whose expression, or lack thereof, can be screened for or scored in some way. Marker genes for use in the practice of the present invention include, but are not limited to transcribable polynucleotide molecules encoding β-glucuronidase (GUS, described in U.S. Pat. No. 5,599,670), green fluorescent protein and variants thereof (GFP, described in U.S. Pat. Nos. 5,491,084 and 6,146,826), proteins that confer antibiotic resistance, or proteins that confer herbicide tolerance. Useful antibiotic resistance markers, including those encoding proteins conferring resistance to kanamycin (nptII), hygromycin B (aph IV), streptomycin or spectinomycin (aad, spec/strep) and gentamycin (aac3 and aacC4), are well known in the art. Herbicides for which transgenic plant tolerance has been demonstrated and to which the method of the present invention can be applied, may include, but are not limited to: amino-methyl-phosphonic acid, glyphosate, glufosinate, sulfonylureas, imidazolinones, bromoxynil, dalapon, dicamba, cyclohexanedione, protoporphyrinogen oxidase inhibitors, and isoxasflutole herbicides. Transcribable polynucleotide molecules encoding proteins involved in herbicide tolerance are known in the art, and may include, but are not limited to, a transcribable polynucleotide molecule encoding 5-enolpyruvylshikimate-3-phosphate synthase (EPSPS for glyphosate tolerance, described in U.S. Pat. Nos. 5,627,061; 5,633,435; 6,040,497; and 5,094,945); a transcribable polynucleotide molecule encoding a glyphosate oxidoreductase and a glyphosate-N-acetyl transferase (GOX, described in U.S. Pat. No. 5,463,175; GAT, described in U.S. Patent Publication No. 20030083480; and dicamba monooxygenase, described in U.S. Patent Publication No. 20030135879); a transcribable polynucleotide molecule encoding bromoxynil nitrilase (Bxn for Bromoxynil tolerance, described in U.S. Pat. No. 4,810,648); a transcribable polynucleotide molecule encoding phytoene desaturase (crtI) described in Misawa, et al. (*Plant Journal* 4:833-840, 1993; and *Plant Journal* 6:481-489, 1994) for norflurazon tolerance; a transcribable polynucleotide molecule encoding acetohydroxyacid synthase (AHAS, aka ALS) described in Sathasiivan et al. (*Nucl. Acids Res.* 18:2188-2193, 1990) for tolerance to sulfonylurea herbicides; and the bar gene described in DeBlock, et al. (*EMBO Journal* 6:2513-2519, 1987) for glufosinate and bialaphos tolerance. The promoter molecules of the present invention may express linked transcribable polynucleotide molecules that encode for phosphinothricin acetyltransferase, glyphosate resistant EPSPS, aminoglycoside phosphotransferase, hydroxyphenyl pyruvate dehydrogenase, hygromycin phosphotransferase, neomycin phosphotransferase, dalapon dehalogenase, bromoxynil resistant nitrilase, anthranilate synthase, aryloxyalkanoate dioxygenases, acetyl CoA carboxylase, glyphosate oxidoreductase, and glyphosate-N-acetyl transferase.

Included within the term "selectable markers" are also genes that encode a secretable marker whose secretion can be detected as a means of identifying or selecting for transformed cells. Examples include markers that encode a secretable antigen that can be identified by antibody interaction, or even secretable enzymes that can be detected catalytically. Selectable secreted marker proteins fall into a number of classes, including small, diffusible proteins that are detectable, (e.g. by ELISA), small active enzymes that are detectable in extracellular solution (e.g. α-amylase, β-lactamase, phosphinothricin transferase), or proteins that are inserted or trapped in the cell wall (such as proteins that include a leader sequence such as that found in the expression unit of extension or tobacco pathogenesis related proteins, also known as tobacco PR-S). Other possible selectable marker genes will be apparent to those of skill in the art and are encompassed by the present invention.

Cell Transformation

The term "transformation" refers to the introduction of nucleic acid into a recipient host. As used herein, the term "host" refers to a bacterium, a fungus, or a plant, including any cells, tissue, organs, or progeny of the bacterium, fungus, or plant. For instance, a host cell according to the present invention may be any cell or organism, such as a plant cell, algal cell, algae, fungal cell, fungi, bacterial cell, insect cell, or the like. In an embodiment, hosts and transformed cells may include cells from: bacteria, fungi, or plants.

As used herein, the term "transformed" refers to a cell, tissue, organ, or organism into which a foreign polynucleotide molecule, such as a construct, has been introduced. The introduced polynucleotide molecule may be integrated into the genomic DNA of the recipient cell, tissue, organ, or organism such that the introduced polynucleotide molecule is inherited by subsequent progeny. A "transgenic" or "transformed" cell or organism also includes progeny of the cell or organism and progeny produced from a breeding program employing such a transgenic organism as a parent in a cross and exhibiting an altered phenotype resulting from the presence of a foreign polynucleotide molecule. The term "transgenic" refers to a bacterium, fungus, or plant containing one or more heterologous polynucleic acid molecules.

There are many methods for introducing polynucleic acid molecules into host cells. The method may generally comprise the steps of selecting a suitable host cell, transforming the host cell with a recombinant vector, and obtaining a transformed host cell. Suitable methods include bacterial infection (e.g. *Agrobacterium*), binary bacterial artificial chromosome vectors, direct delivery of DNA (e.g. via PEG-mediated transformation, desiccation/inhibition-mediated DNA uptake, electroporation, agitation with silicon carbide fibers, and acceleration of DNA coated particles, etc. (reviewed in Potrykus, et al., *Ann. Rev. Plant Physiol. Plant Mol. Biol.* 42: 205, 1991).

Technology for introduction of a DNA molecule into cells is well known to those of skill in the art. Methods and materials for transforming host cells by introducing a DNA construct or module into a host genome in the practice of this invention can include any of the well-known and demonstrated methods. Any transformation methods may be utilized to transform a host cell with one or more promoters, constructs, and/or modules of the present invention.

The transformed host cells may be analyzed for the presence of the genes of interest and the expression level and/or profile conferred by the regulatory elements of the present invention. Those of skill in the art are aware of the numerous methods available for the analysis of transformed cells. For example, methods for analysis include, but are not limited to Southern blots or northern blots, PCR-based approaches, biochemical analyses, phenotypic screening methods, field evaluations, and immunodiagnostic assays. The expression of a transcribable polynucleotide molecule can be measured using TaqMan® (Applied Biosystems, Foster City, Calif.) reagents and methods as described by the manufacturer and PCR cycle times determined using the TaqMan® Testing Matrix. Alternatively, the Invader® (Third Wave Technologies, Madison, Wis.) reagents and methods as described by the manufacturer can be used to evaluate transgene expression.

The present invention also provides for bacterial cells and cultures of bacterial cells that express one or more gene expression cassettes or modules in accordance with the invention for degradation or depolymerization of lignin to produce a bioproduct such as PHA or a lipid.

A transgenic organism of the invention may pass along a transgenic polynucleotide molecule to its progeny. Progeny may include any cell comprising the transgene derived from an ancestor cell. The transgenic organism may be homozygous for the transformed polynucleotide molecule and transmit that sequence to all offspring. The transmission may be the result of sexual reproduction, or the result of asexual reproduction, for example budding, binary fission, or the like. Progeny may be grown from, for example, seeds produced by a transgenic plant, or from bacterial or fungal cells grown in culture. Plant progeny may then be self-pollinated to generate a true breeding line of plants. The progeny from these plants, or bacteria or fungal cells may be evaluated, among other things, for gene expression. The gene expression may be detected by several common methods such as western blotting, northern blotting, immunoprecipitation, and ELISA.

Having now generally described the invention, the same will be more readily understood through reference to the following examples which are provided by way of illustration, and are not intended to be limiting of the present invention, unless specified. It should be appreciated by those of skill in the art that the techniques disclosed in the following examples represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

Example 1

Discovery of a Lignin-Degrading *Pseudomonas putida* Strain

Figure 1A:
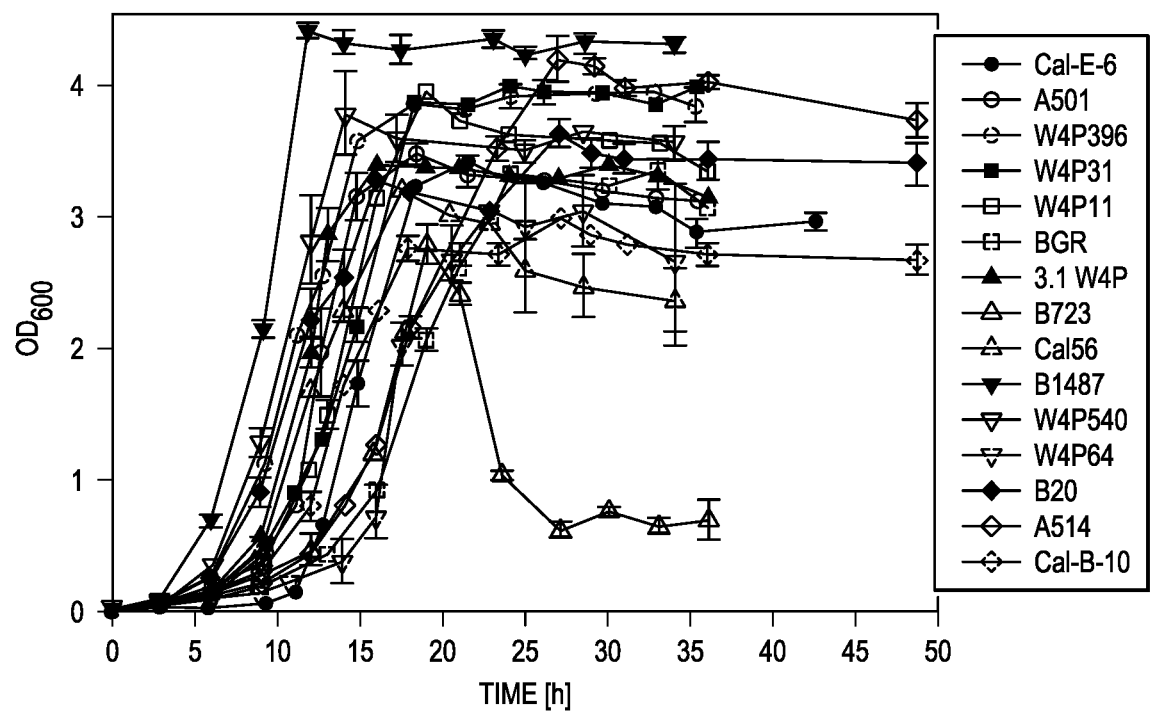
FIG. 1—Shows growth curves of fifteen *P. putida* strains in M9 medium on different carbon sources. A) Growth curves of fifteen *P. putida* strains in M9 medium with 20 mM glucose. All fifteen strains were able to grow in M9 medium with glucose. B) Growth curves of eight *P. putida* strains in M9 medium with 20 mM xylose. Only eight of the fifteen strains that were able to grow in M9 medium with xylose are shown. C) Growth curves of six *P. putida* strains in M9 medium with 20 mM vanillate. Only six of the fifteen strains that were able to grow in M9 medium with vanillate are shown. D) Growth curves of four *P. putida* strains in M9 medium with 1% (w/t) lignin.
Figure 1B:
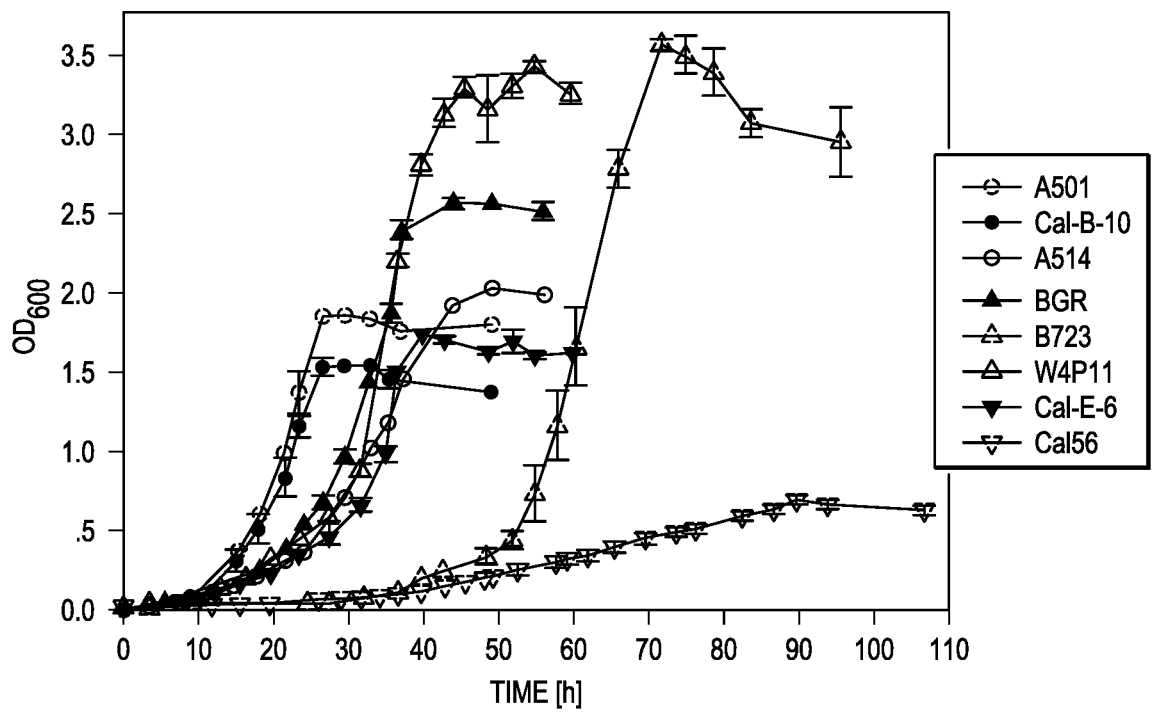
Figure 1C:
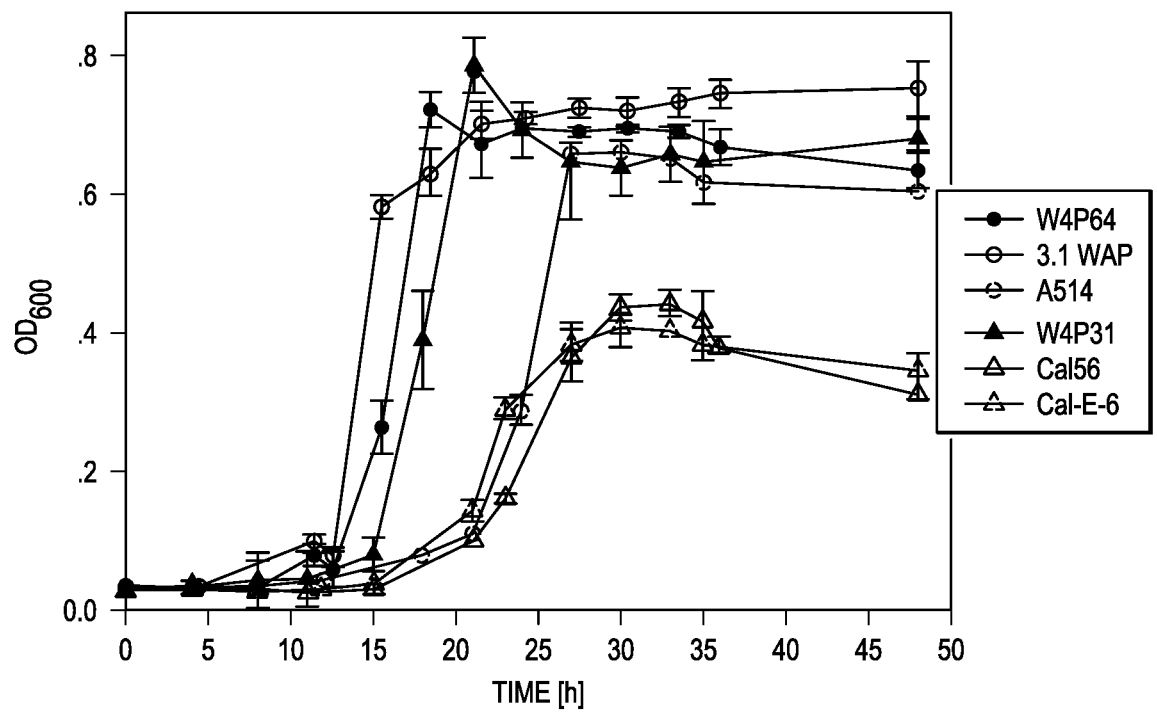
Figure 1D:
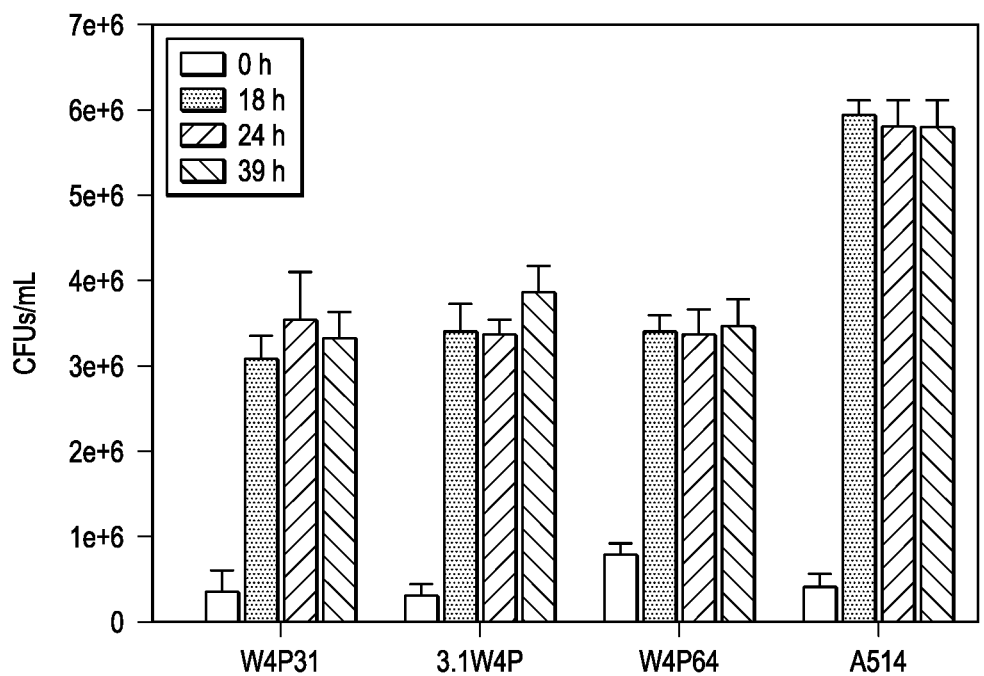
Figures 1, 2A:
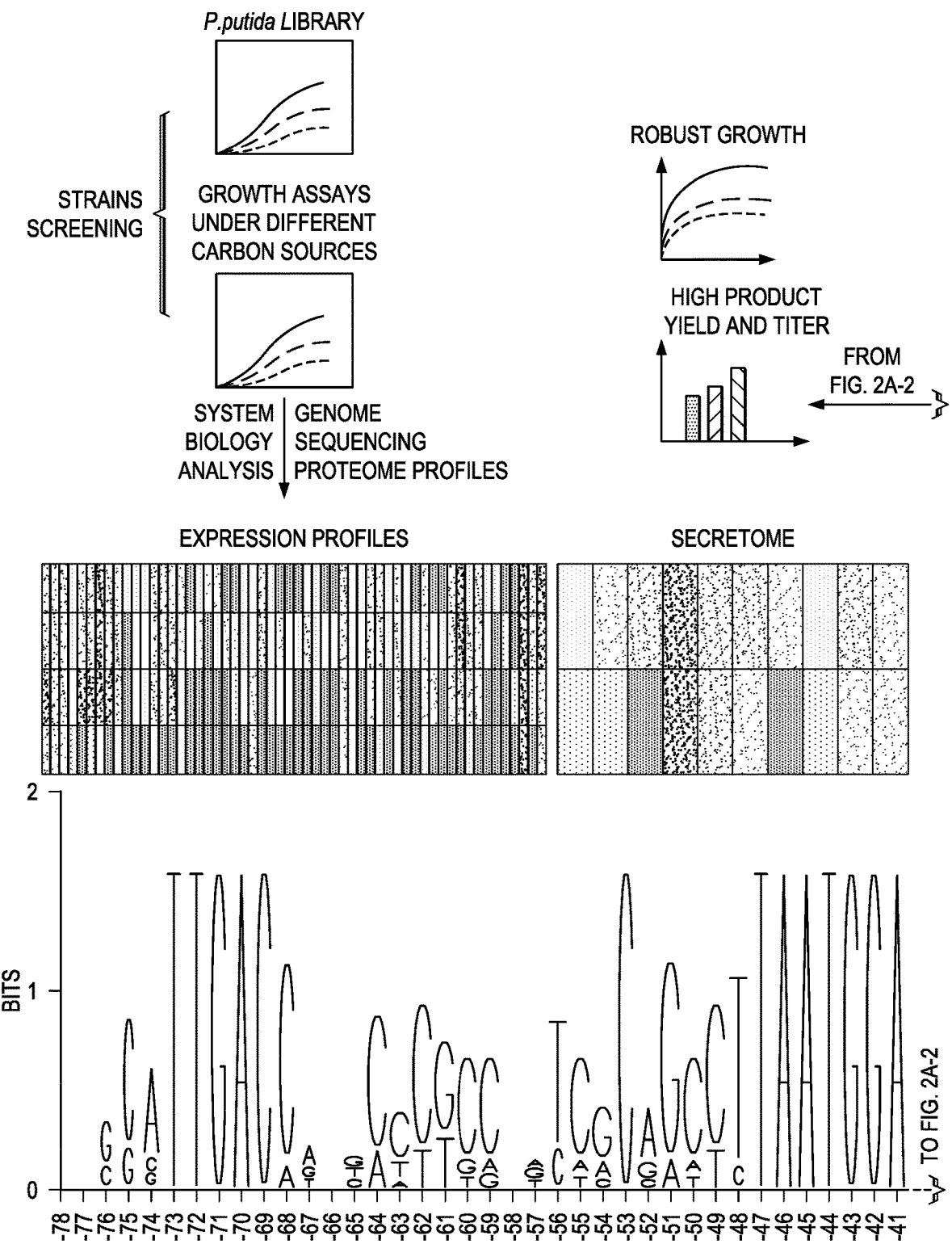
Figure 2A:
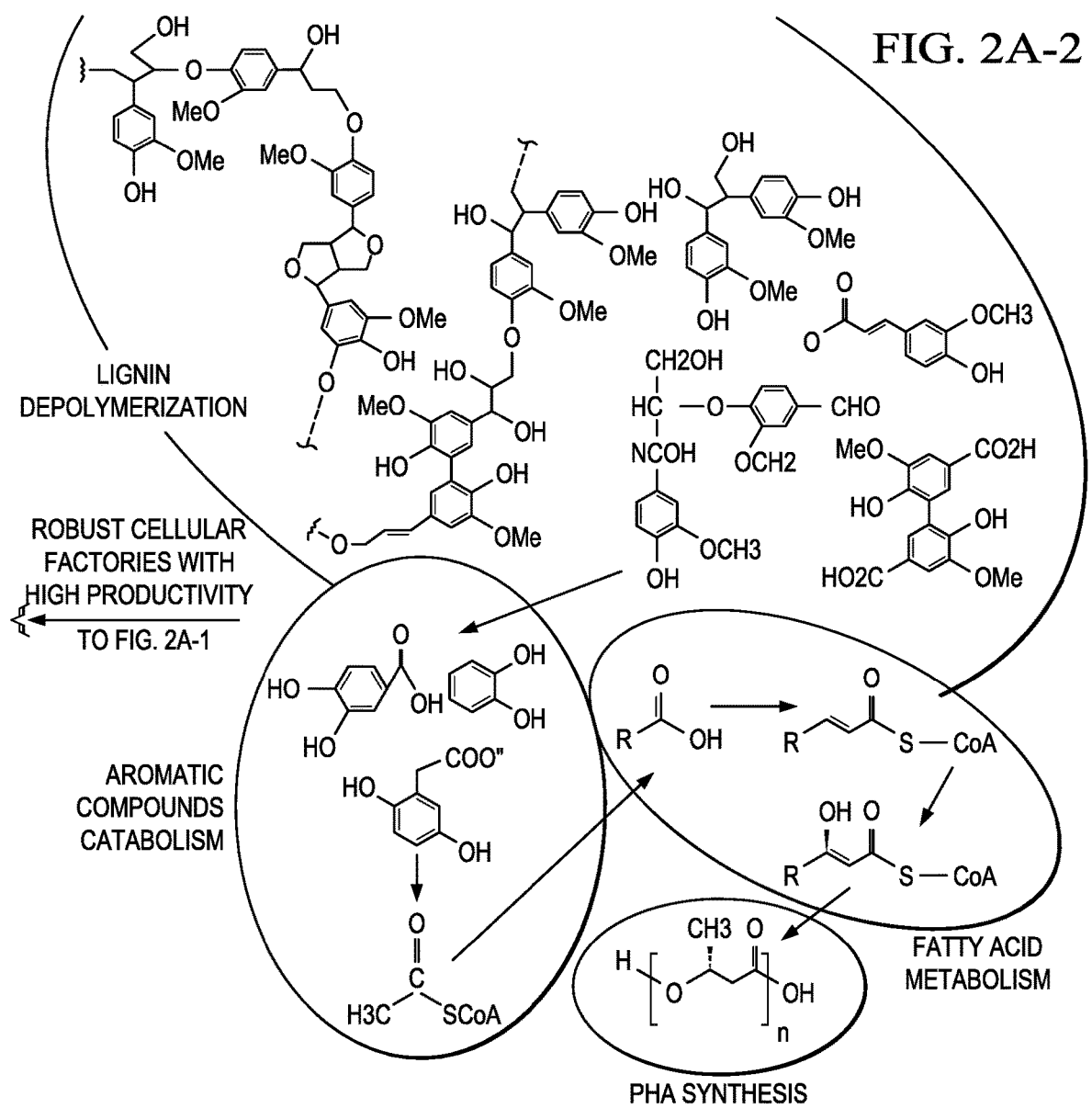
FIG. 2—Shows an experimental strategy tracking an innovative lignin-to-PHA route. (A-1 and A-2) Overview of the experimental strategy. (B) Growth curves of *P. putida* A514 in M9 medium with glucose, xylose, vanillate, or lignin as the sole carbon source. Growth on lignin is expressed as CFU (right Y axis), whereas growth on all other carbon sources is expressed as $OD_{600}$ (left Y axis). (C) Genome atlas for the chromosome of *P. putida* A514. (D) Protein expression levels ($\log_2$ E) for enzymes, regulators, and transporters involved in aromatic compound catabolic pathways.
Figure 2:
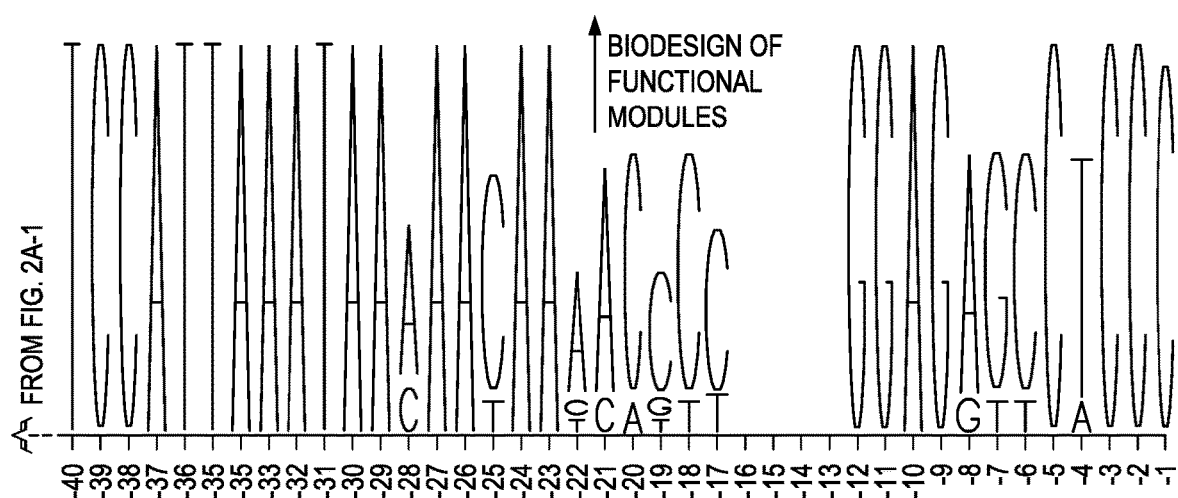
Figure 2B:
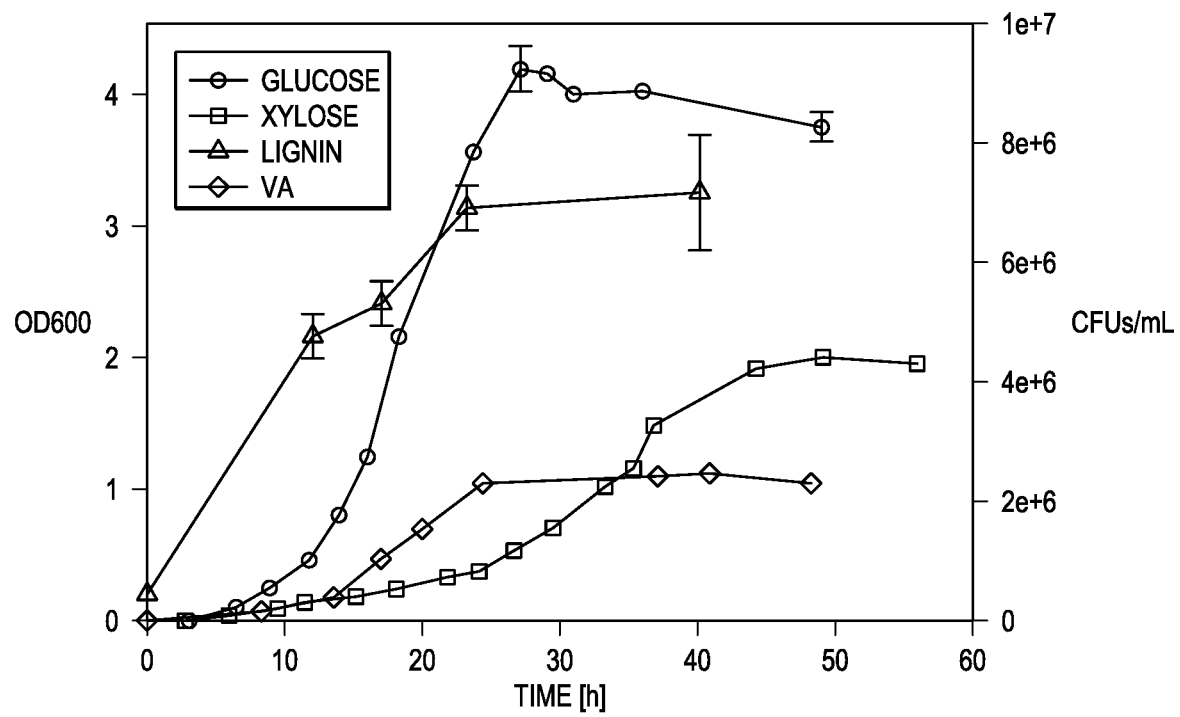

In order to discover a suitable base strain for mechanistic studies and biodesign, fifteen plant-associated *P. putida* wild-type strains isolated from different plant hosts were screened for carbon utilization and lignin consumption. Bacteria were cultivated in M9 mineral medium with different carbon sources by shaking at 30° C. (Bauchop et al., *J Gen Microbiol* 23:457-46, 1960). The four carbon sources were 20 mM glucose, 20 mM xylose, 6 mM vanillic acid (VA) and 1% lignin. Cell growth in liquid media with soluble carbon sources (glucose, xylose, and VA) was monitored by optical density readings at 600 nm ($OD_{600}$) with the corresponding blank medium as reference, whereas cell growth in the presence of 1% lignin was monitored by counting colony forming units (CFU, cell number per milliliter). For OD measurement at high concentration, the cells were diluted to 0.6 to 1 OD for accurate measurement, and the final OD number was converted by multiplying the dilution factor. When necessary, growth media was solidified by the addition of agar to a final concentration of 1.5% (w/v). For polyhydroxyalkanoate (PHA) production, recombinant *P. putida* A514 strains were grown in M9 medium with 30 μg/ml gentamicin and 15 μg/ml tetracycline as antibiotics, as well as with VA or lignin as the sole carbon source. All experiments were performed in triplicate. To optimize fermentation conditions, lignin was pretreated with sodium hydroxide. Briefly, 1% lignin in medium was adjusted to pH 12.5 with 50% NaOH solution to dissolve lignin powder. The pH was then adjusted to 7.0-7.5 with dilute 2 M HCl As shown in FIGS. 1A, B, and C, the strains displayed various carbon utilization patterns, with *P. putida* A514 (A514) being one of the few strains that can utilize broad carbon sources. Among the 15 strains studied, only three strains (Cal-E-6, Cal56, and A514) can utilize glucose, xylose, vanillic acid (VA), and lignin as the sole carbon source. *P. putida* A514 achieved the highest cell growth on glucose, xylose, and VA among these three strains (FIG. 1A-D and FIG. 2-1 and 2A-2). Furthermore, to investigate the lignin utilization capacity for these *Pseudomonas* strains, four strains with higher cell density under VA were selected to grow on Kraft lignin as the sole carbon source (FIG. 1D). As shown in FIGS. 1D and 2B, a ten-fold increase in CFU indicated that *P. putida* A514 can grow on lignin as the sole carbon source with the highest cell density among these four strains, making it an ideal base strain for studying the mechanisms for lignin utilization and designing functional modules. The comparative genomics, proteomics, and systems biology analyses were subsequently evaluated in order to identify the mechanisms and guide biodesign.

Example 2

Comparative Genomics Revealed the Lignin Degradation Capacity of *P. putida* A514

Genomic DNA of *P. putida* A514 was isolated as previously described (Lin et al., *PLoS Genet* 7:e1002318, 2011). Shot gun libraries were constructed (Camarena et al., *PLoS Pathog* 6:e1000834, 2010) and sequenced using two platforms. Illumina® sequencing was carried out by Texas A&M Agrilife Genomics Core with a paired end library of 100-bp reads on Illumina® HiSeq 2500. PacBio sequencing was carried out by Duke University, IGSP Genome Sequencing & Analysis Core Resources with a library of 5 kb insert size. Illumina® short reads were first assembled to obtain contigs using SOAPdenovo (Li et al., *Genome Res* 20:265-272, 2010), and the contigs were further analyzed using a hybrid assembly approach to integrate the pre-assembled contigs with PacBio long reads following the RS_AHA_Scaffolding analysis protocol in the SMRT Analysis v2.2.0. Gene models were predicted using the online server Prodigal v1.20 (Hyatt et al., *BMC Bioinformatics* 11:119, 2010) and BLAST against the Uniprot database for functional annotation. A whole-genome atlas for *P. putida* A514 was generated using the GeneWiz browser, v0.94 (available at cbs.dtu.dk/services/gwBrowser/).

Genome and gene sequence data of twelve *P. putida* strains with publicly available completed genomes were downloaded from NCBI (GenBank Accession Number JSVW00000000). Protein sequence similarity searches and multiple protein sequence alignments were performed to identify the genes involved in lignin depolymerization, aromatic compound catabolism, and PHA synthesis in *P. putida* A514 and an additional twelve *P. putida* strains (Bugg et al., *Nat Prod Rep* 28:1883-1896, 2011; Floudas et al., *Science* 336:1715-1719, 2012; Jimènez et al., *Environ Microbiol* 4:824-841, 2002; Masai et al., *Biosci Biotechnol Biochem* 71:1-15, 2007). The draft genome of *P. putida* A514 was annotated and compared with 12 other sequenced *P. putida* strains, including KT2440 and GB-1, as well as the known aromatic-degrading strain F1 (Table 1 and FIG. 2C). Comparative genomics analysis revealed that *P. putida* A514 has evolved mechanisms for lignin depolymerization and aromatic compound utilization with several features.

TABLE 1

Comparison of the general features of *P. putida* strains A514 with twelve additional *P. putida* strains.

| | Number of bases (Mb) | GC Content (%) | Number of coding sequences | Percentage of coding region (%) |
|---|---|---|---|---|
| A514 | 6.78 | 59.9 | 6493 | 88.2 |
| DLL-E4 | 6.48 | 62.5 | 5861 | 85.3 |
| BIRD-1 | 5.73 | 61.7 | 4960 | 86.9 |
| DOT-T1E | 6.26 | 61.4 | 5721 | 87.3 |
| F1 | 5.96 | 61.9 | 5249 | 88.7 |
| GB-1 | 6.08 | 61.9 | 5408 | 89.5 |
| H8234 | 6.87 | 61.6 | 6357 | 86.7 |
| PC9 | 5.96 | 62.6 | 5386 | 86.1 |
| KT2440 | 6.18 | 61.5 | 5350 | 86.8 |
| NBRC 14164 | 6.16 | 62.3 | 5449 | 88.8 |
| ND6 | 6.20 | 61.7 | 6289 | 88.4 |
| S16 | 5.98 | 62.3 | 5218 | 84.9 |
| W619 | 5.77 | 61.4 | 5182 | 88.9 |

Figure 2C:
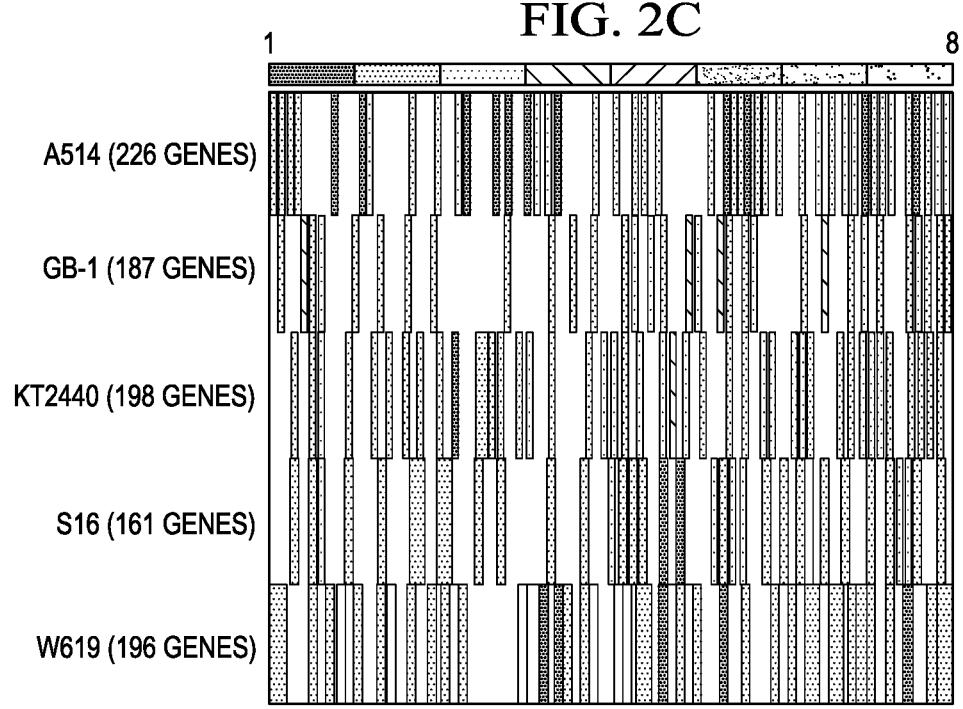

First, the *P. putida* A514 genome is enriched with genes encoding enzymes for lignin depolymerization (FIG. 2C). As compared to the 12 other genomes investigated, *P. putida* A514 genome encodes a broad range of oxidoreductases suitable for lignin depolymerization, including some unique enzymes that do not exist in other *P. putida* strains (Floudas et al., *Science* 336:1715, 2012). These enzymes include a laccase (PputA514_1683) and several peroxidases belonging to two families: the Class-II peroxidase family (generic peroxidases, PputA514_3972) and the dye-decolorizing peroxidase superfamily (PputA514_2985). In particular, one of the dye-decolorizing peroxidases (DyP, PputA514_2985) was specific to *P. putida* A514, and was shown to be induced and secreted on lignin substrate. In addition to the enzymes that directly participate in lignin depolymerization, lignin-degrading enzymes involved in peripheral reactions were identified in the *P. putida* A514 genome. These enzymes included oxidases (glyoxal oxidase, glucose oxidase, and methanol oxidase) to generate $H_2O_2$ production for sustainable peroxidase function, quinone reductases to reduce iron for the Fenton reaction, and cytochrome P450 monooxygenases for downstream events of the lignin degradation process (Floudas et al., *Science* 336:1715, 2012) (Table 1). Overall, genome analysis revealed that the *P. putida* A514 genome contains enzymes required for lignin depolymerization. In addition, this capacity can be further enhanced to promote lignin depolymerization.

Figure 3A:
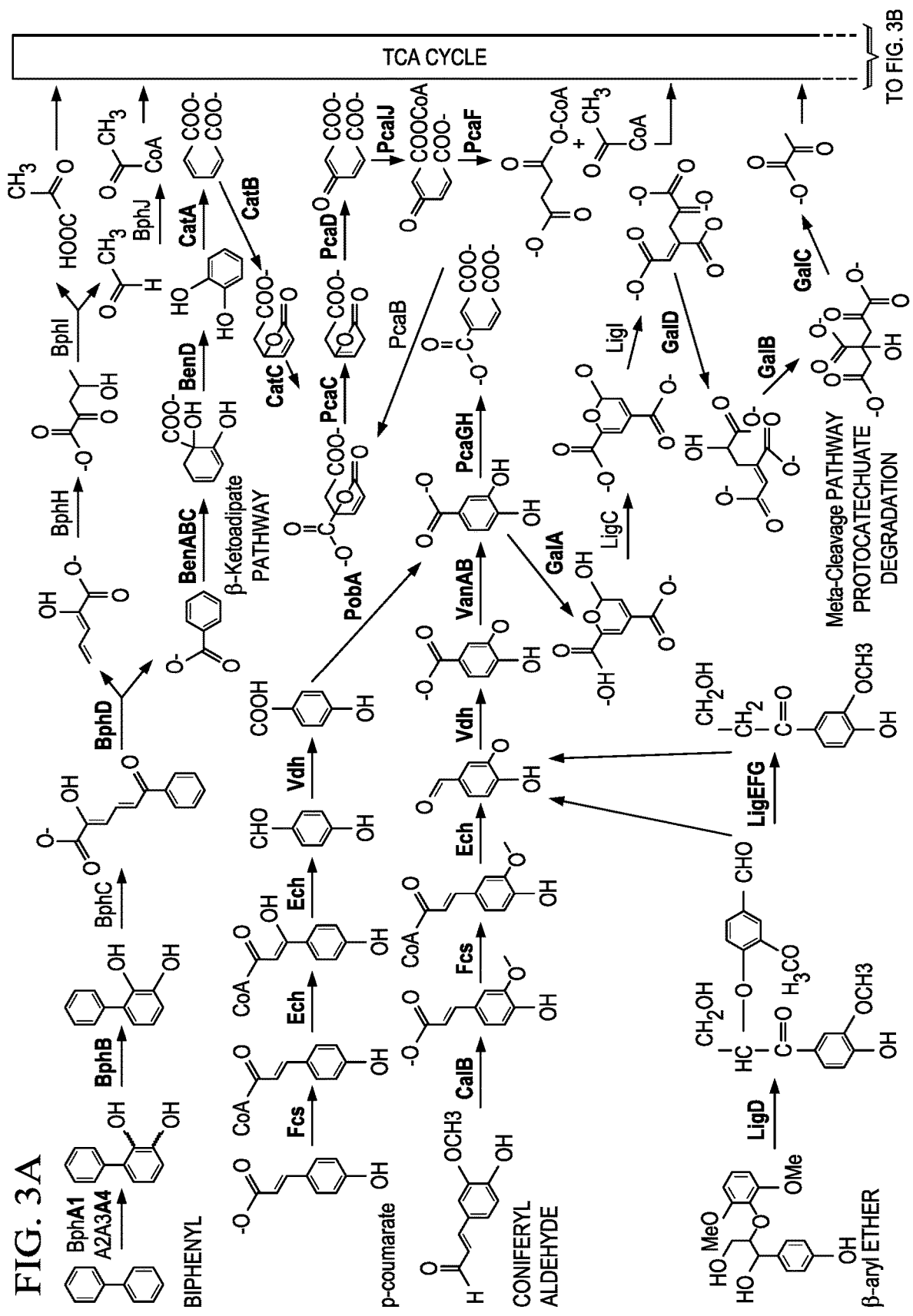
FIG. 3—Shows genes involved in aromatic catabolism in *P. putida* A514. The genes colored in red exist in the A514 genome. The genes colored in black exist in other bacteria.
Figure 3B:
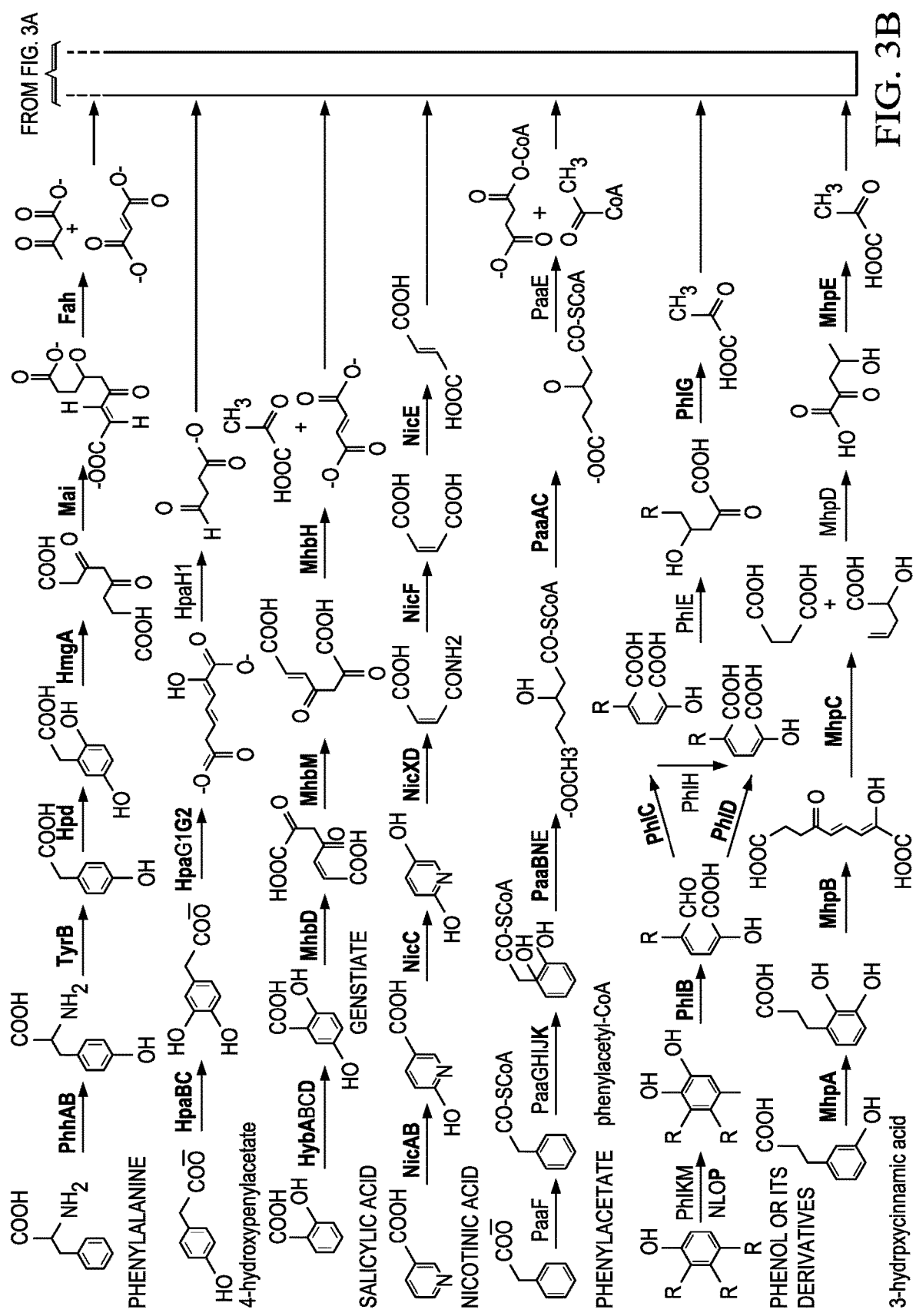
Figure 4:
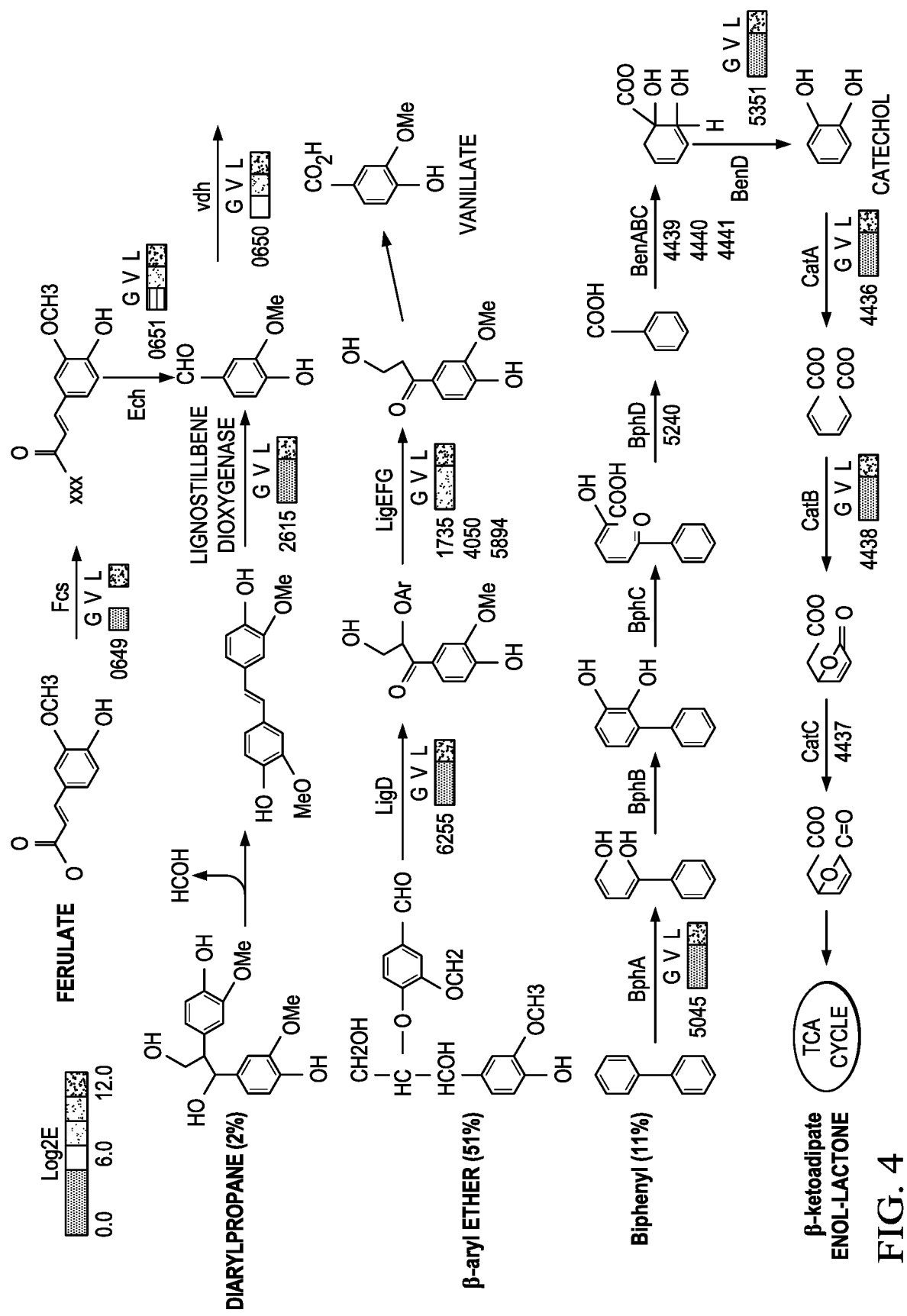
FIG. 4—Shows degradation pathways of lignin derivatives for *P. putida* A514 and expression levels (log 2E) of enzymes involved in these pathways.
Figure 5A:
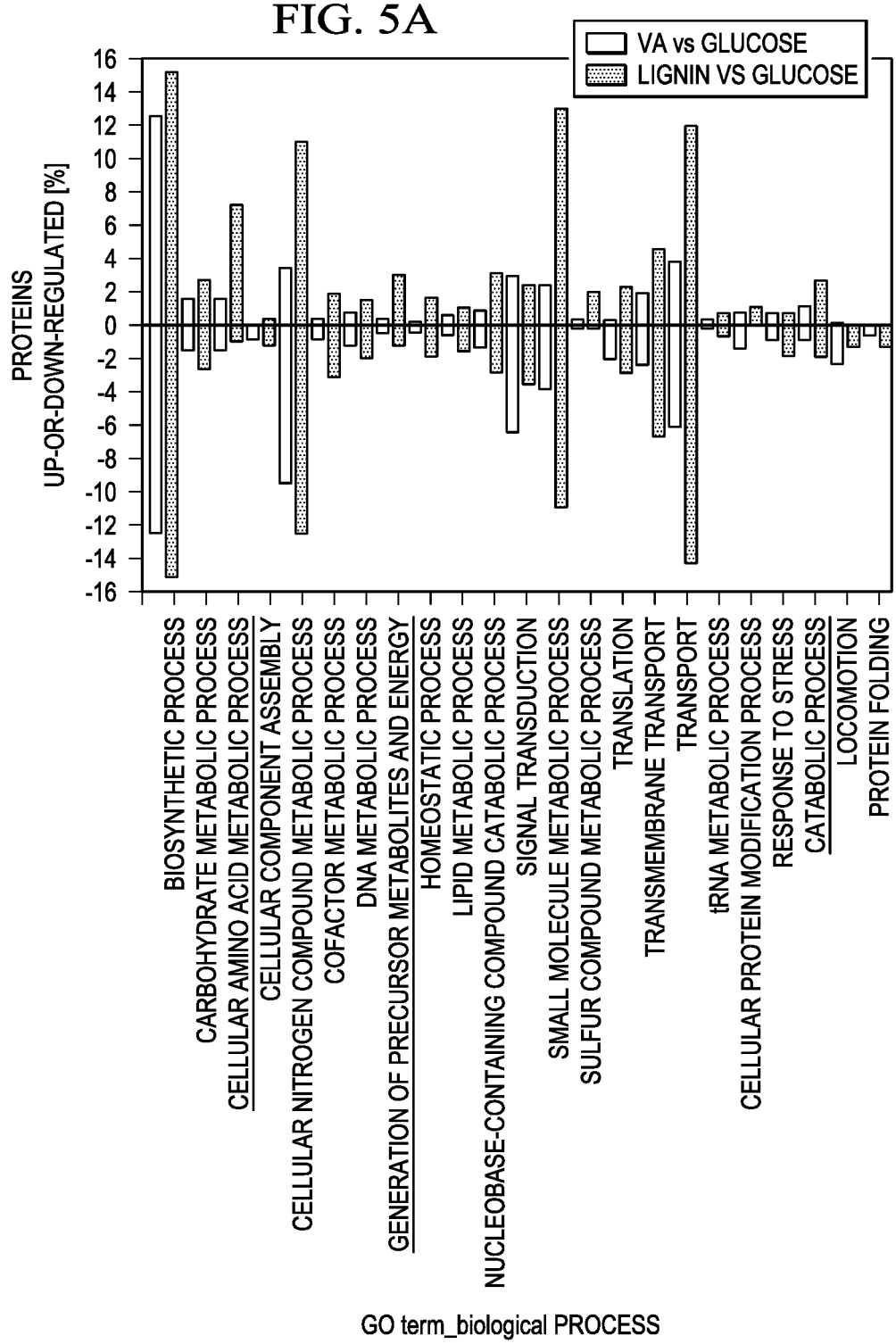
FIG. 5—Shows functional patterns of A514 proteins altered in expression when grown on three different carbon sources: glucose, VA, and lignin. A) Proportions of differentially expressed proteins under each gene ontologies (GO) term among the total number of differentially expressed genes were indicated to evaluate the disturbance of each process. Positive value indicated up-regulated expression, whereas negative value showed down-regulated expression. B) Proteins belonging to different GO categories that were over-expressed in vanillic acid as compared to glucose. C) Proteins belonging to different GO categories that were over-expressed in lignin as compared to glucose. D) Proteins belonging to different GO categories that were over-expressed in lignin as compared to VA. Red line indicated that some GO categories, where proteins were expressed at higher levels in lignin or vanillic acid as compared to glucose.
Figure 5B:
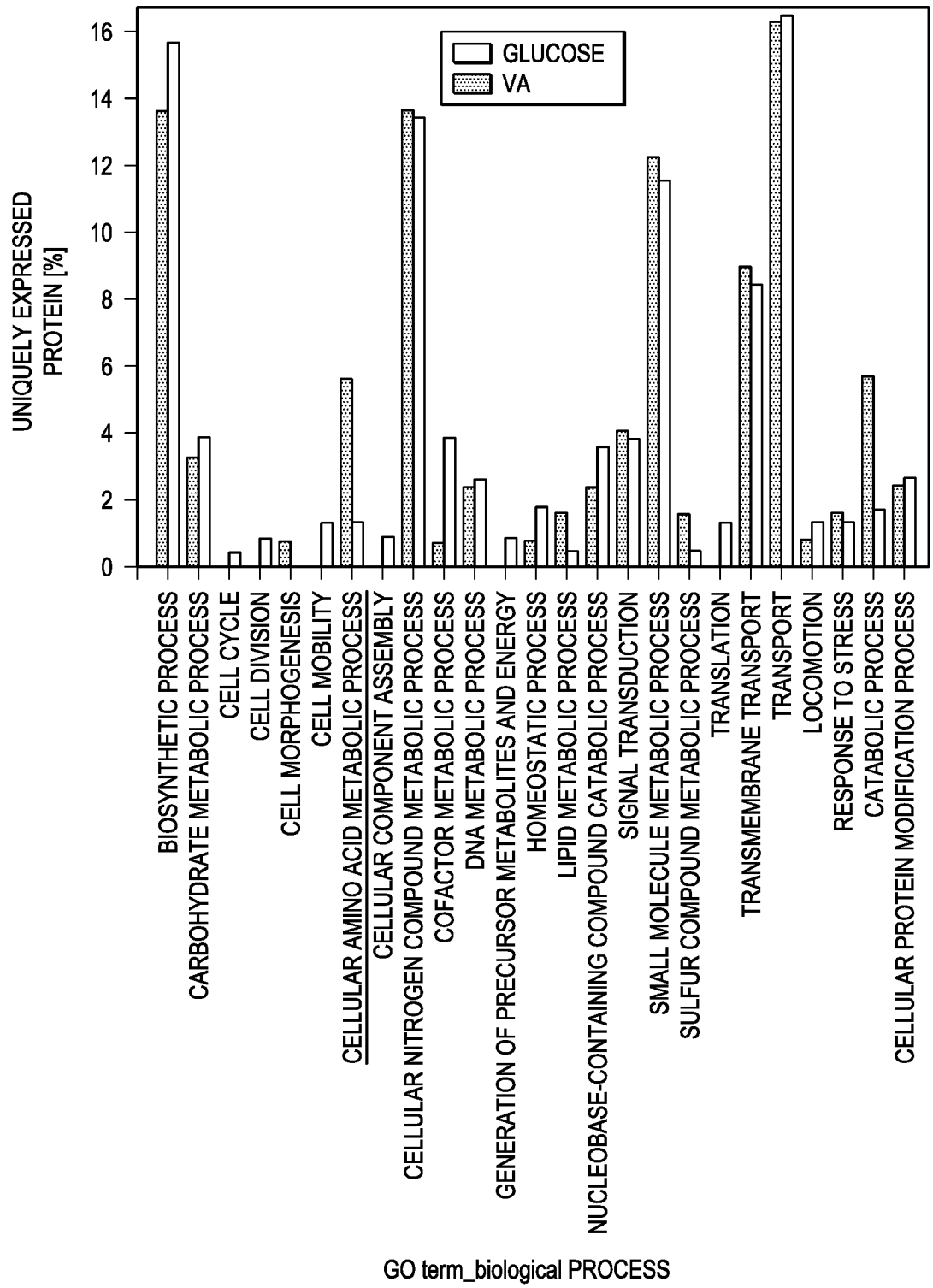
Figure 5C:
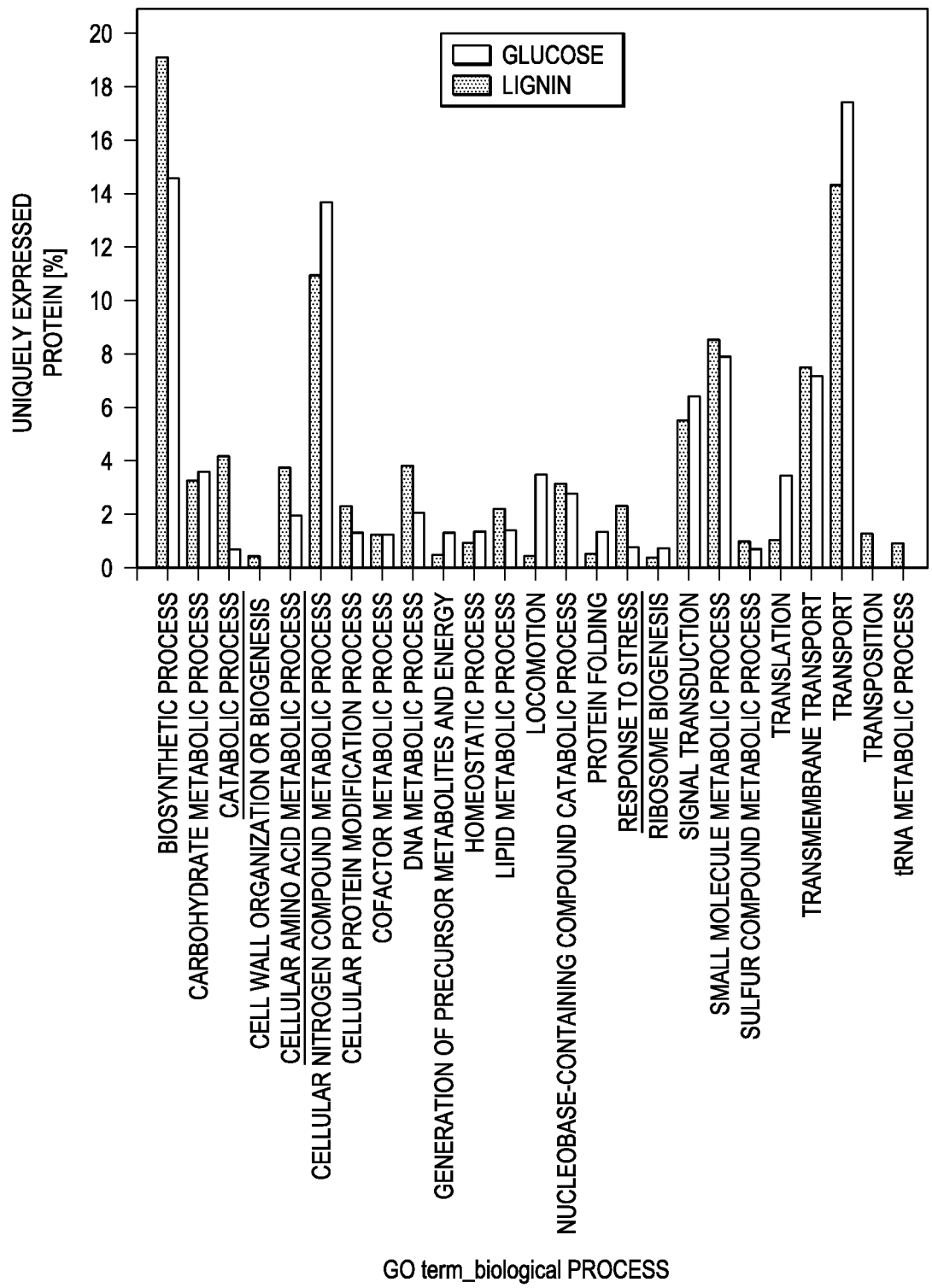
Figure 5D:
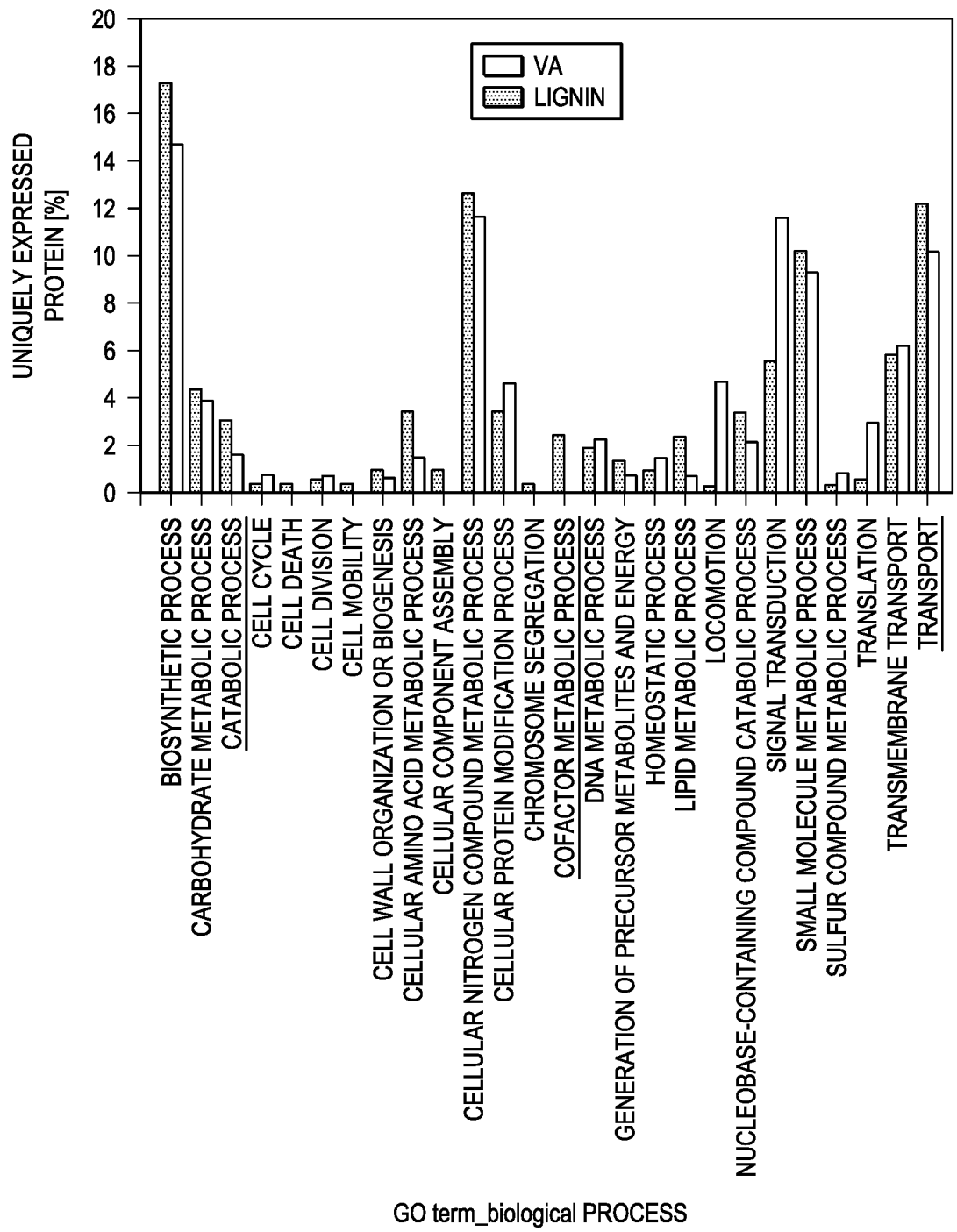

Second, *P. putida* A514 contains catabolic pathways for degrading lignin-derived aromatic oligomers into aromatic monomers (Bugg et al., *Nat. Prod. Rep.* 28:1883, 2011; Bugg et al., *Curr. Opin. Biotechnol.* 22:394, 2011). Three major pathways were identified based on gene models derived from the A514 genome (Ragauskas et al., *Science* 344:1246843, 2014; Wu et al., *FEMS Microbiol Rev* 35:299-323, 2011). These pathways include O-aryl ether degradation pathway, biphenyl degradation pathway, and diarylpropane degradation pathway as discussed in detail below (FIGS. 3 and 4). These pathways can funnel lignin-derived oligomer aromatics to the intermediates for major aromatic degradation pathways.

β-aryl ether degradation pathway: β-aryl ether is the most abundant linkage in lignin (50-70%) (Masai et al., *Biosci Biotechnol Biochem* 71:1-15, 2007) and potentially can be catabolized by a cascade of reactions in *P. putida* A514. The chemical linkage can be first oxidized by the NAD-dependent dehydrogenase LigD (PputA514_6255) and then converted to ketone aromatic monomers by a glutathione-dependent β-etherase (LigEFG, PputA514_4050, and PputA514_5894). The ketone product can then be catabolized to VA, a key central metabolite for the β-ketoadipate pathway.

Biphenyl degradation pathway: Depending on the lignin source, the biphenyl component could account for up to 10% of lignin. The bphABCD genes (PputA514_5045, PputA514_3697 and PputA514_6181) from *P. putida* A514 encode enzymes to transform the biphenyl component into chloro-benzoate, which can be further catabolized into catechol, another key intermediate of the β-ketoadipate pathway.

Diarylpropane degradation pathway: In fungi, the $C_\alpha$-$C_\beta$ bond is often cleaved by a lignin peroxidase to produce aromatic aldehyde products. The A514 genome contains a gene potentially encoding lignostilbene dioxygenase (PputA514_2615) to catalyze the oxidative cleavage of lignostilbene to produce two molecules of VA. Lignostilbene dioxygenase is expected to play an important role in catalyzing the cleavage of $C_\alpha$-$C_\beta$ linkage in relevant oligomers.

Figure 2D:
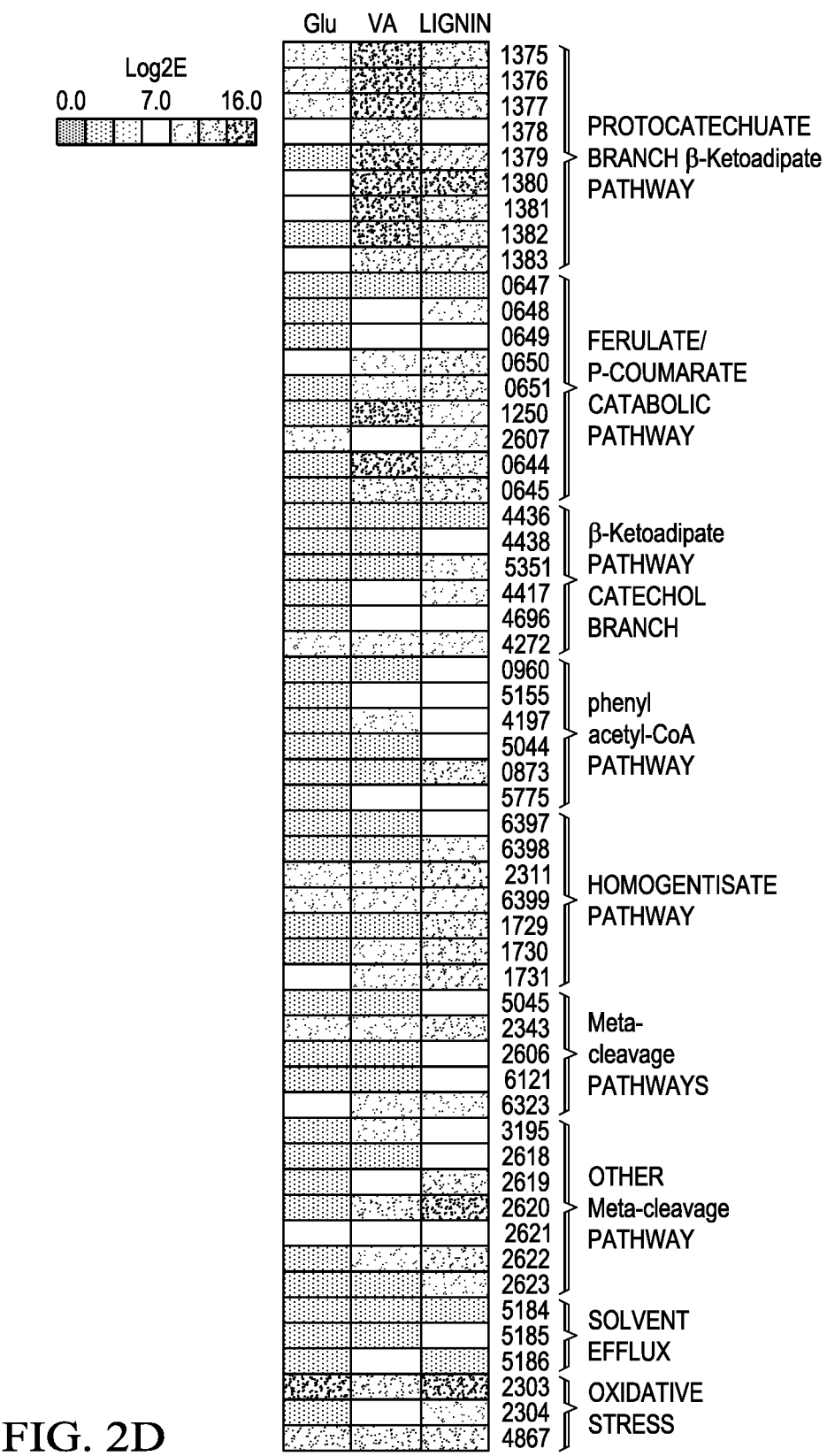

Third, the *P. putida* A514 genome also contains genes related to several major pathways for the catabolism of lignin-derived aromatic monomers into central metabolites like acetyl-CoA and succinate. These pathways include the protocatechuate (pca genes, PputA514_1375-1383) and catechol (cat genes, PputA514_4436-4438) branches of the 3-ketoadipate pathway, as well as the homogentisate pathway (phh/hpd/hmg/fah/mai genes, PputA514_1729-1731 and PputA514_6397-6399) (FIGS. 2D and 3). In addition, other aromatic compound-degradation pathways such as the homoprotocatechuate pathway (PputA514_5319-5320 and PputA514_3195) and nicotinate pathway (PputA514_2848-2856) were also found in the *P. putida* A514 genome (FIG. 3).

Overall, genome analysis revealed that *P. putida* A514 encodes enzymes involved in all major steps of lignin degradation including lignin depolymerization and aromatic compound catabolism. Based on the genomics study, proteomics and systems biology modeling were carried out to further elucidate the mechanisms for lignin conversion into bioproducts and to design three functional modules to achieve consolidated lignin bioprocessing.

Transporters for aromatic compounds: Even though aromatic compounds might enter cells by passive diffusion at high concentrations, recent studies suggested that active transport is the primary mechanism for aromatic compound catabolism. Proteomics analysis confirmed that a broad range of transporters were up-regulated when *P. putida* A514 was grown on VA and lignin substrates. Major facilitator superfamily (MFS) transporters and outer membrane porins such as PputA514_4268, PputA514_4696, PputA514_3332, and PputA514_1372 were up-regulated when *P. putida* A514 was grown on VA substrate. Lignin substrate led to the up-regulation of even more transporters including many additional MFS transporters, extracellular solute-binding proteins, and outer membrane porins as shown in both secretome and whole cell proteomics. In addition, three ABC transporters (PputA514_5668, PputA514_1753 and PputA514_3310) were also induced, which was consistent with the previous report on ABC transporter's role in aromatic compound transport. Overall, the proteomics analysis indicated that a diverse group of transporters were activated to uptake different aromatic compounds derived from lignin. The proteins involved in lignin depolymerization, aromatic compound degradation and transport thus formed a well-coordinated network to enable the lignin conversion to various products.

Aromatic catabolic pathway-specific transcriptional regulators: An effective regulatory network is essential for *P. putida* capacity to catabolize diverse lignin-derived aromatic compounds. Many transcriptional factors regulated the gene expression in aromatic compound degradation pathways to enable the coordination among lignin depolymerization, aromatic compound degradation, and downstream reactions. In particular, the AraC-type, IcIR-type and LysR-type regulators were induced to regulate the vanillic acid-related ortho-cleavage pathways, when A514 was grown on VA substrate. For example, PobR (PputA514_1251), an AraC-type regulator, was induced to activate the expression of a pobA for p-hydroxybenzoate degradation. PcaR (PputA514_1385), a well characterized IcIR-type transcriptional activator, was specifically expressed to activate the pcaIJ in the β-ketoadipate pathway. Noticeably, an uncharacterized LysR family transcriptional regulator (LTTRs) (PputA514_1263) was specifically detected when *P. putida* A514 was grown on VA substrate. All identified LTTRs were transcriptional activators involved in responses to chemical inducers. In particular, many well-known LTTRs regulated genes (e.g., CatR, CbnR) involved in ortho-cleavage pathways. This new LTTR might be a VA-specific activator for aromatic compound catabolism. Other transcriptional regulators induced by lignin included PaaX (GntR, PputA514_5564) for phenylacetate degradation, vanR (GntR, PputA514_6155) for VA degradation, and AraC-type regulator (PputA514_0323) probably regulating the meta-cleavage pathway operon. The proteomics thus suggested that a regulatory network existed to achieve coordinative degradation of various aromatic compounds derived from lignin.

Stress response: Although aromatic compounds can be used as carbon and energy sources by *P. putida*, they are also stressors for the bacteria that might be membrane-damaging and macromolecule-disrupting agents. When *P. putida* are exposed to these compounds, the bacteria often respond by expressing proteins involved in stress responses. For example, glutathione S-transferase domain-containing protein (PputA514_2989), alkyl hydroperoxide reductase (PputA514_2303) and catalase (PputA514_4867) were upregulated to alleviate oxidative damage in the presence of lignin.

Lipid metabolism and aromatic amino acids metabolism: *P. putida* A514 growing on lignin and aromatic compounds not only up-regulated a network of enzymes and regulators for aromatic compound degradation, but also had a significant changes in carbon metabolisms. The detailed changes and relevance to bioconversion was discussed in the main text. In short, the presence of PHA biosynthesis enzymes and the more active fatty acid β-oxidation pathway indicated that carbon flux can be manipulated toward PHA accumulation. Overall, the systems biology analysis revealed a well-regulated metabolic network to coordinate the lignin depolymerization and aromatic compound degradation for lignin conversion. In addition, the PHA production capacity existed in *P. putida* A514 and the increased β-oxidation could lead to new strategies to enhance PHA production using lignin as substrate.

Example 3

Proteomics Analysis Revealed that *P. putida* A514 Responds to Lignin Treatment by Coordinately Up-Regulating Enzymes and Pathways Comprehensive proteomics analysis was carried out to compare protein expression patterns when *P. putida* A514 was grown on different carbon sources including glucose, VA, and lignin.

For intracellular total protein extraction, cells from 100 ml culture were harvested at late-exponential phase by centrifugation (9000 rpm for 10 min at 4° C.) and washed twice with 10 ml PBS buffer (PH 7.4). Cells were then resuspended in 5 ml Alkaline-SDS buffer (5% SDS; 50 mM Tris-HCl, pH 8.5; 0.15 M NaCl; 0.1 mM EDTA; 1 mM $MgCl_2$; 50 mM DTT) with 1 mM PMSF. Cell lysis was performed with tip-probe sonication (Branson, Danbury, Conn.) using 4 cycles of 30 s. Lysates were then centrifuged at 12,000×g for 15 min at 4° C. to collect supernatant.

In addition, secretome proteomics analysis was carried out to study the secretion of lignin depolymerization enzymes when *P. putida* A514 was grown with lignin as the sole carbon source. For secretome analysis, extracellular protein was extracted from culture supernatants harvested at late-exponential phase by centrifugation. The supernatants (from extracellular supernatant or intracellular lysates) were precipitated with 100% Trichloroacetic acid (TCA) overnight at −20° C. The protein pellet was collected by centrifugation at 12,000×g for 30 min and washed three times with chilled acetone. SpeedVac was used to remove residual acetone, and Reagent Type 4 Working Solution provided by the total protein extraction kit (Sigma-Aldrich, St. Louis, Mo.) was used to incubate the pellet. The pellet was then centrifuged at 13,000×g for 30 minutes, and the supernatant was collected and stored at −80° C. until used for proteomics.

For MudPIT-based shotgun proteomics, approximately 100 μg of protein was digested by Trypsin Gold, Mass Spectrometry Grade (Promega, Wis., USA) and desalted using a Sep-Pak plus C18 column. The desalted sample was then loaded onto a biphasic capillary column. Two-dimensional liquid chromatography separation and tandem mass spectrometry conditions followed the previously described protocol (Zhang et al., *BMC Bioinformatics* 13 Suppl 15:S8, 2012; Zhang et al., *Mol Cell Proteomics* 12:3431-3442, 2013). Tandem mass spectra were extracted from the raw files and converted into an MS2 file. The MS2 file was searched against the *P. putida* A514 protein database generated from gene models in the genomics analysis. The ProLuCID algorithm was used to search the database using the Texas A&M Supercomputing facility (College Station, Tex.). Protein identification was assessed using DTASelect 2.0. Proteins with more than two peptides were identified as they were detected and were recorded. The differential protein expression analysis was calculated based on the normalized total peptide count as previously described (Zhang et al., *Mol Cell Proteomics* 12:3431-3442, 2013).

Proteomics-based systems biology revealed that the efficient conversion of lignin to PHA required synergy at multiple levels including lignin depolymerization, aromatic compound degradation, and PHA biosynthesis from fatty acid β-oxidation. The systems level mechanisms enabled the biodesign of efficient functional modules for lignin depolymerization, aromatic compound utilization and PHA production. The proteomics analysis identified 1500, 1303, and 1760 proteins for *P. putida* A514 grown on glucose, VA, and lignin substrates, respectively. The proteome covered 23-27% of the 6491 predicted proteins of *P. putida* A514. The proteome for each carbon source had approximately 250 to 500 uniquely expressed proteins. Differential protein expression patterns were analyzed using glucose substrate as a control. The proteomics analysis indicated that lignin and VA treatment induced expression of proteins with gene ontologies (GO) related to cellular amino acid metabolism, generation of precursor metabolites, and catabolic processes (FIG. 5). In particular, VA treatment induced the expression of genes involved in cellular amino acid metabolism, generation of precursor metabolites, energy and catabolic metabolism, catabolic processes, and lipid metabolic processes. Cells grown in lignin substrate induced expression of genes involved in cellular amino acid metabolism, catabolic metabolism, and response to stress in *P. putida* A514. These expression patterns indicated that catabolic pathways for lignin degradation and stress adaptation could be important for *P. putida* A514 to utilize lignin. Detailed pathway analysis revealed molecular and systems mechanisms for lignin utilization as described in detail below.

Figure 6A:
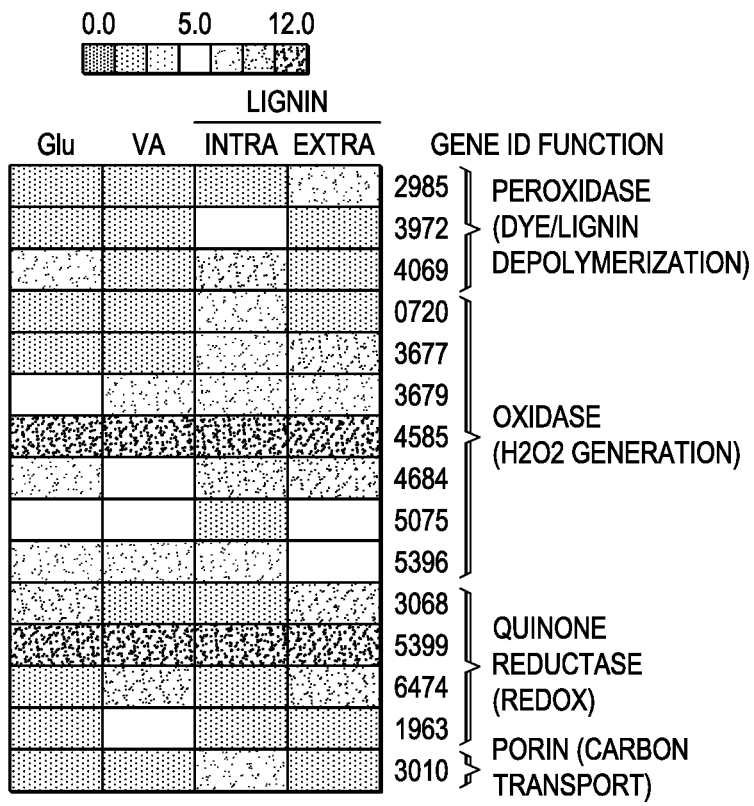
FIG. 6—Shows a biodesign of a lignin depolymerization module. (A) Protein expression levels ($\log_2$ E) of potential lignin depolymerization enzymes in *P. putida* A514 under different carbon sources. (B) Protein expression levels ($\log_2$ E) identified secretome proteomics. (C) Dyp2 enzyme activity in the extracellular space for engineered *P. putida* A514 strains with different combination of signal peptides and DYP2 enzyme. (D) Growth curves of *P. putida* A514 with the pPROBE-GT plasmid carrying either the P1099 promoter only ($A_{pGP1099}$, control), the p1099 promoter, pelB signal peptide, and dyp2 gene ($A_{pelB\_DyP2}$), or the p1099 promoter, oprI signal peptide and dyp2 gene ($A_{oprI\_DyP2}$) Strains were grown in M9 medium with 1% lignin as the sole carbon source.

Proteomics analysis correlated well with comparative genomics, in that many enzymes involved in lignin depolymerization and aromatic compound catabolism were up-regulated under lignin or VA treatment (FIGS. 2D, 4, and 6A). Systems biology analysis revealed several important aspects of lignin utilization mechanisms in *P. putida* A514, which further guided the biodesign of functional modules.

Example 4

Molecular Mechanisms for Lignin Depolymerization and Biodesign of a Lignin Depolymerization Module The proteomics of *P. putida* A514 under lignin treatment revealed complementary enzymatic systems for lignin depolymerization. Among the ten genes encoding putative peroxidases in the *P. putida* A514 genome, two (PputA514_2985 and 4069) were specifically expressed when *P. putida* A514 was grown on lignin as the sole carbon source (FIG. 6A). In particular, one of the two proteins, a DyP (PputA514_2985) was identified in the secretome under lignin treatment. Complementary to the peroxidases, enzymes participating in reactions peripheral to lignin degradation were also induced under lignin treatment. These enzymes included oxidases involved in $H_2O_2$ generation (PputA514_3677, 3679 and 4684) and quinone reductases involved in iron reduction (PputA514_3068 and 6474) (Floudas et al., *Science* 336:1715, 2012) (FIG. 6A). This complementary enzymatic system is thought to promote lignin depolymerization by a catalytic network formed by the oxidases and DYP to generate and utilize $H_2O_2$.

Even though *P. putida* A514 could utilize lignin as the sole carbon source, the relatively poor cell growth as compared to the performance of fungal strains on lignin substrate reflected the metabolic limitations for lignin utilization in bacterial species (FIG. 2B). The lignin depolymerization module was therefore designed to promote lignin degradation, cell growth, and end product titer. Because dye peroxidase (DYP) and associated enzymes already existed as a catalytic network, a strong dye peroxidase was introduced to enhance lignin depolymerization capacity.

Figure 6B:
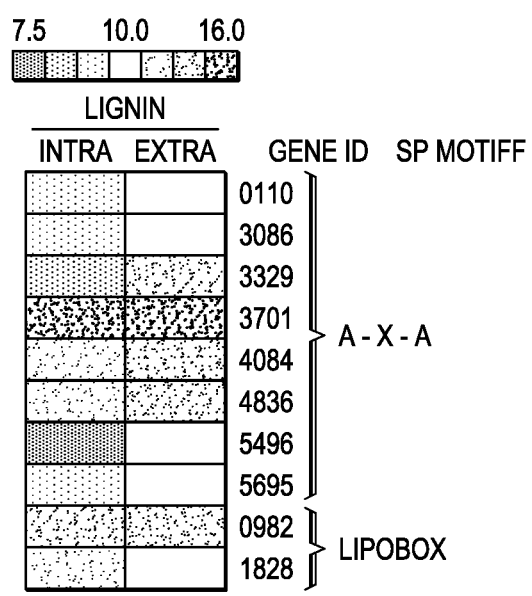
Figure 6C:
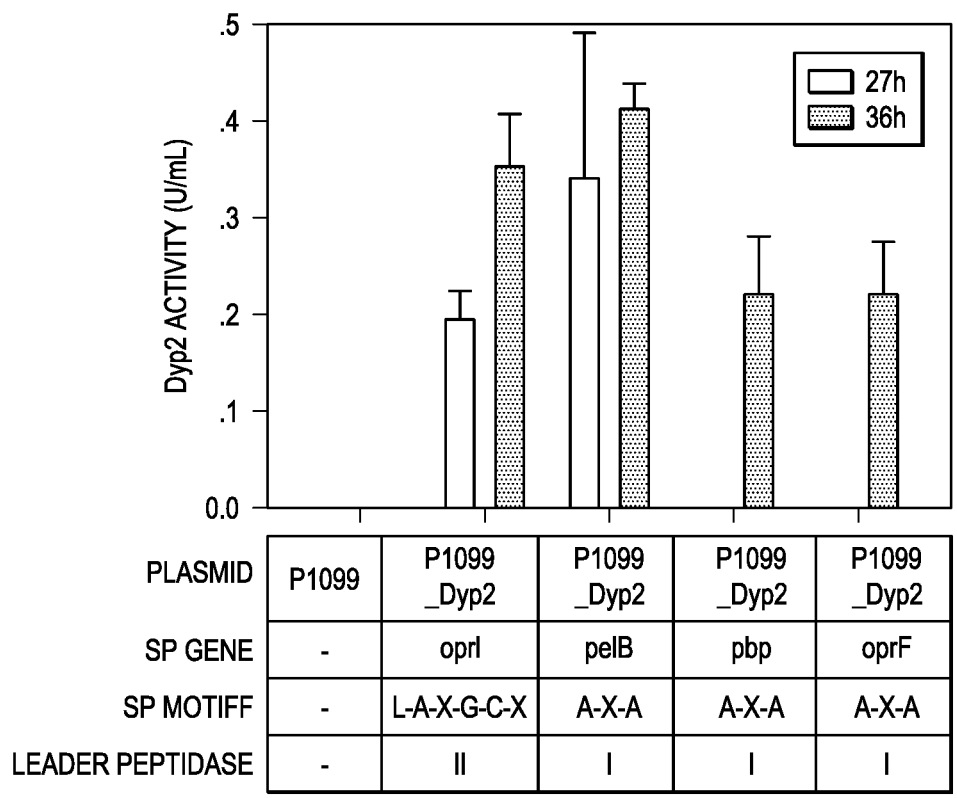

Three components were considered for an effective functional module: an efficient peroxidase enzyme, an effective promoter, and suitable secretion signal peptides. First, a multifunctional dye peroxidase (DYP2) from a lignin-degrading bacterium *Amycolatopsis* sp. 75iv2, was chosen, as this enzyme has been demonstrated to have high activity on a broad range of peroxidase substrates, as well as the capacity to depolymerize lignin (Brown et al., *ACS Chem. Biol.* 7:2074, 2012). Second, a strong constitutive promoter, p1099, from a cold-shock DNA-binding domain-containing protein, was chosen based on proteomics analysis. Third, a suitable secretion signal peptide was identified based on secretome analysis. Ten secreted proteins were analyzed to identify their secretion signal peptides, and all of the ten secretion signal peptides belonged to the Sec-pathway-dependent type II secretion system containing A-X-A and/or L-A-X-G-C-X (SEQ ID NO:35) motifs (FIGS. 6B and C) (Georgiou et al., *Curr Opin Biotechnol* 16:538-545, 2005; Choi et al., *Appl Microbiol Biotechnol* 64:625, 2004; Rezwan et al., *Microbiology* 153:652, 2007). Four out of the ten secretion signal sequences (from OprI, OprF, Pbp, and PelB) were examined for the efficiency to secrete Dyp2 (Dammeyer et al., *Microb Cell Fact* 10:11, 2011). The results suggested that all four secretion signal peptides can facilitate the secretion of Dyp2 based on extracellular peroxidase activity, although the strengths of these signal peptides are different (FIG. 6C).

Therefore, a lignin depolymerization module was built by combining the p1009 promoter, the Dyp2 enzyme, and either the pelB or OprI secretion signal peptides as described below. Empty expression vector pGP1099 was constructed by inserting constitutive promoter P1099 from the genome of *P. putida* A514 into plasmid pPROBE-GT. This plasmid was then used as a control and to build additional constructs (Miller et al., *Mol Plant Microbe Interact* 13:1243-1250, 2000). Putative signal peptide sequences were predicted using SignalP 4.0 from proteins identified from secretome analysis (Petersen et al., *Nat Methods* September 29; 8(10):785-6, 2011). The signal peptides from phosphate-binding protein (Pbp, PputA514_0110), outer membrane lipoprotein (OprI, PputA514_0982), outer membrane porin F (OprF, PputA514_3701) and the *E. carotovora* PelB (Dammeyer et al., *Microb Cell Fact* 10:11, 2011) were amplified from the genome of *P. putida* A514 and then fused to the multifunctional dye peroxidase (DYP2) coding sequence from *Amycolatopsis* sp. 75iv2 (Brown et al., *ACS Chem Biol* 7: 2074-2081, 2012) to produce the 1.4-kb PCR fragments. These fragments were sub-cloned into plasmid pGP1099 to produce constructs pGPelbDyp2, pGOprIDyp2, pGOprFDyp2, and pGPelbDyp2 (Table 2).

For the aromatic compound degradation module, a 2.3-kb PCR fragment containing vanA and vanB gene (PputA514_0644-0645), as well as their 281-bp promoter ($P_{van}$) was amplified from the *P. putida* A514 genome and ligated in the plasmid pPROBE-GT to generate construct pGVAN. For the PHA production module, a PCR fragment containing the phaJ4, $P_{van}$ promoter along with phaC1 or phaC2 genes were amplified and sub-cloned into plasmid pPROBE-GT to produce constructs pGJ4C1 and pGJ4C2 (Table 2). The resultant plasmids were transformed into *P. putida* A514 through chemical transformation (Mercer et al., *J Bacteriol* 140:37-42, 1979), followed by selection with 30 µg/ml gentamicin.

Figure 6D:
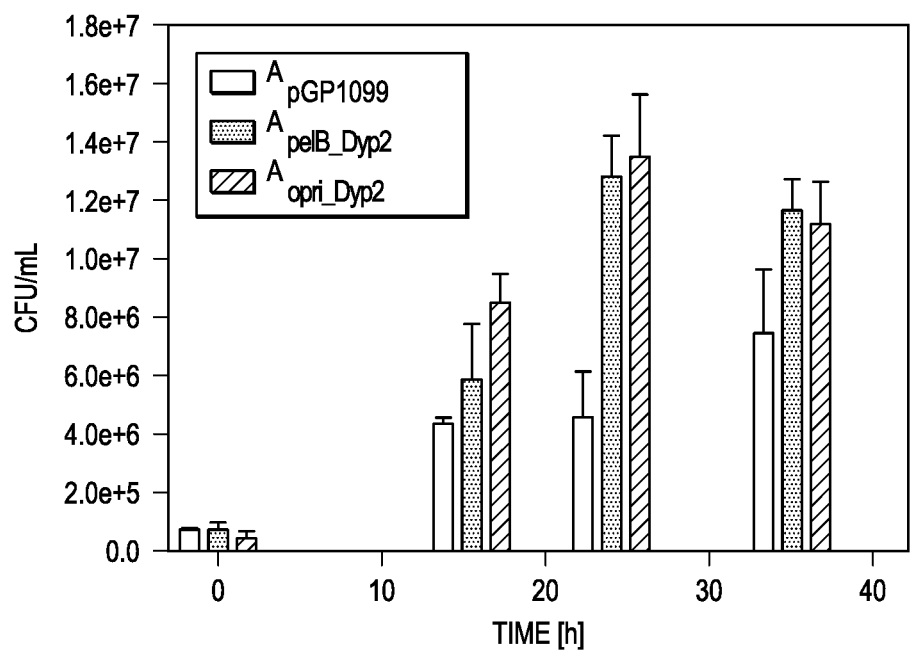

Two types of recombinant *P. putida* A514 strains were designated $A_{pelB\_DyP2}$ and $A_{oprI\_DyP2}$, whereas *P. putida* A514 carrying the control plasmid pGP1099 was designated $A_{pGP1099}$ (FIG. 6D). Both $A_{pelB\_DyP2}$ and $A_{oprI\_DyP2}$ achieved higher cell density than the negative control when grown in M9 medium supplemented with 1% lignin. The CFU of $A_{pelB/oprI\_DyP2}$ at stationary phase was 2.3 times greater than that of the control strain $A_{pGP1099}$ (FIG. 2D). Furthermore, the improved lignin degradation capacity was also demonstrated by $^{31}P$ NMR analysis of lignin degradation as discussed below. The lignin-depolymerization module thus validated the DYP-based lignin depolymerization mechanism in *P. putida* A514 and enabled more rapid cell growth through promoting more efficient depolymerization of lignin.

TABLE 2

Plasmids and bacteria used in the study.

| Strain or Plasmid | Relevant characteristics | Source or reference |
|---|---|---|
| Strains | | |
| *P. putida* A514 | Wild type, glucose, xylose, vanillate and lignin utilization | Prof. Dennis Gross lab (TAMU) |
| *P. putida* Cal-E-6 | Wild type, glucose and xylose and vanillate utilization | Prof. Dennis Gross lab (TAMU) |
| *P. putida* A501 | Wild type, glucose and xylose utilization | Prof. Dennis Gross lab (TAMU) |
| *P. putida* W4P396 | Wild type, glucose utilization | Prof. Dennis Gross lab (TAMU) |
| *P. putida* W4P31 | Wild type, glucose, xylose, vanillate and lignin utilization | Prof. Dennis Gross lab (TAMU) |
| *P. putida* W4P11 | Wild type, glucose and xylose utilization | Prof. Dennis Gross lab (TAMU) |
| *P. putida* BGR | Wild type, glucose and xylose utilization | Prof. Dennis Gross lab (TAMU) |
| *P. putida* 3.1 W4P | Wild type, glucose, xylose, vanillate and lignin utilization | Prof. Dennis Gross lab (TAMU) |
| *P. putida* B723 | Wild type, glucose and xylose utilization | Prof. Dennis Gross lab (TAMU) |
| *P. putida* Cal56 | Wild type, glucose and xylose and vanillate utilization | Prof. Dennis Gross lab (TAMU) |
| *P. putida* B1487 | Wild type, glucose utilization | Prof. Dennis Gross lab (TAMU) |
| *P. putida* W4P540 | Wild type, glucose utilization | Prof. Dennis Gross lab (TAMU) |
| *P. putida* W4P64 | Wild type, glucose, xylose, vanillate and lignin utilization | Prof. Dennis Gross lab (TAMU) |
| *P. putida* B20 | Wild type, glucose utilization | Prof. Dennis Gross lab (TAMU) |
| *P. putida* Cal-B-10 | Wild type, glucose, xylose, vanillate utilization | Prof. Dennis Gross lab (TAMU) |
| Plasmids | | |
| pPROBE-GT | | Obtained from AddGene |
| pPROBE-TT | | Obtained from AddGene |
| pGVAN | pPROBE-GT derivative, *P. putida* A514 vanAB | This study |
| pPvan | pPROBE-GT derivative, *P. putida* A514 promoter of vanAB | This study |
| pGJ4C1 | pPROBE-GT derivative, *P. putida* A514 promoter of vanAB, phaJ4 and phaC1 | This study |
| pGJ4C2 | pPROBE-GT derivative, *P. putida* A514 promoter of vanAB, phaJ4 and phaC2 | This study |
| pGPelbDyp2 | pPROBE-GT derivative, *P. putida* A514 promoter P1099, pelb (E. carotovora) and dyp2 (*Amycolatopsis* sp. 75iv2) | This study |
| pGOprIDyp2 | pPROBE-GT derivative, *P. putida* A514 promoter P1099, OprI, and dyp2 (*Amycolatopsis* sp. 75iv2) | This study |
| pGOprFDyp2 | pPROBE-GT derivative, *P. putida* A514 promoter P1099, OprF, and dyp2 (*Amycolatopsis* sp. 75iv2) | This study |
| pGPbpDyp2 | pPROBE-GT derivative, *P. putida* A514 promoter P1099, Pbp, and dyp2 (*Amycolatopsis* sp. 75iv2) | This study |
| pTP1099 | pPROBE-TT derivative, *P. putida* A514 promoter P1099 | This study |
| pGP1099 | pPROBE-GT derivative, *P. putida* A514 promoter P1099 | This study |
| pTDV | pPROBE-TT derivative, *P. putida* A514 promoter P1099, pelb, dyp2, and vanAB | This study |

Figure 9A:
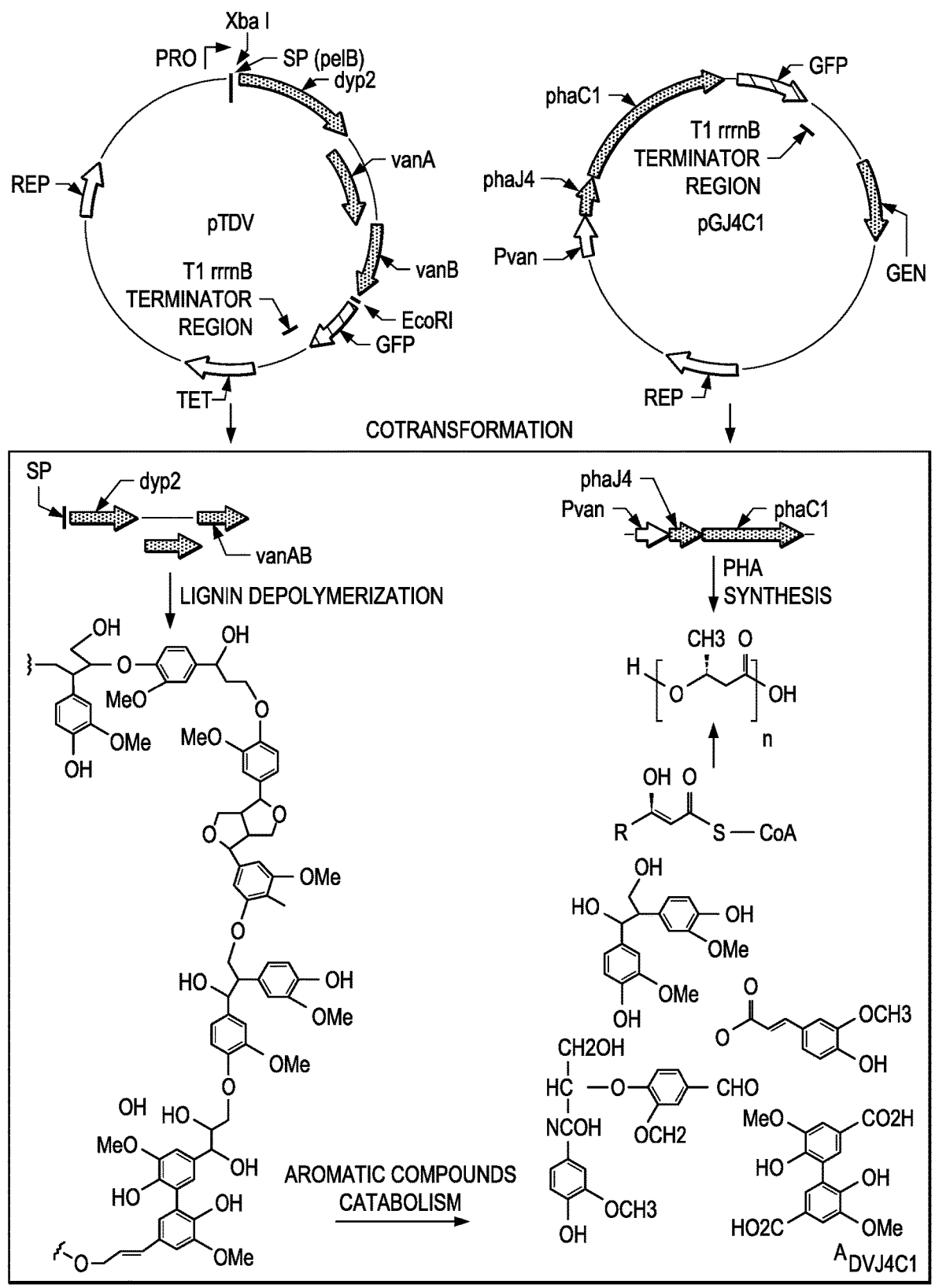
FIG. 9—Shows consolidated lignin processing (CLP) and integration of functional modules in *P. putida* A514 for lignin-to-PHA bioconversion. (A) The integration strategy for the *P. putida* A514 engineered strain ADVJ4C1 carrying modules for lignin depolymerization, aromatic compound degradation, and PHA synthesis modules. (B) Growth curves of the *P. putida* A514 engineered strain in M9 medium with 1% lignin or 1% lignin pretreated with sodium hydroxide. (C) $^{31}$P NMR quantification of the hydroxyl content of lignin remaining in the media after 40 hours growth with each strain. The hydroxyl content of lignin in the growth medium of the wild type was set to 100%, for comparison with the engineered strains. (D) PHA production of the *P. putida* A514 engineering strain in M9 medium with 1% lignin under conditions of N starvation (65 mg/l NH$_4$Cl) and N excess (1 g/l NH$_4$Cl).
Figures 10A, 10B:
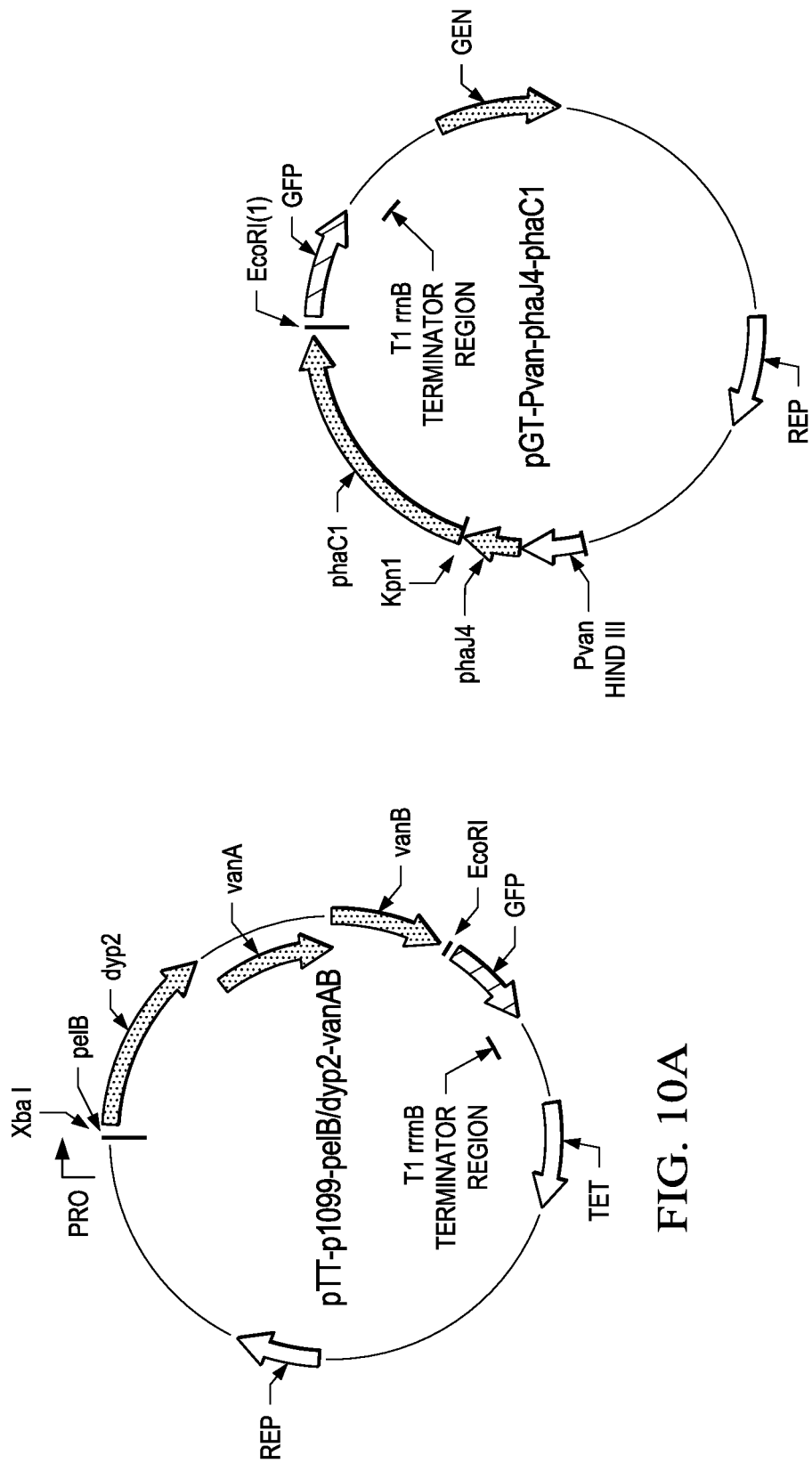
FIG. 10—Shows a lignin depolymerization module and an aromatic compound utilization module integrated into one plasmid in order to integrate all three functional modules. P1099 and pelb/dyp2 was amplified from pGPelbDyp2, and vanAB was amplified from pGVAN. The two fragments were combined into a 4-kb fragment to be subcloned into the plasmid pPROBE-TT to derive the construct pTDV.

In order to integrate all three functional modules, the lignin depolymerization module and the aromatic compound utilization module were integrated into one plasmid. $P_{1099}$ and pelb/dyp2 were amplified from pGPelbDyp2, and vanAB was amplified from pGVAN. The two fragments were combined into a 4-kb fragment to be subcloned into the plasmid pPROBE-TT to derive the construct pTDV (FIG. 9A, 10, and Table 2) (Miller et al., *Mol Plant Microbe Interact* 13:1243-1250, 2000). The plasmids pTDV and pGJ4C1 were co-transformed into *P. putida* A514 and the transformants were subjected to selection on LB agar supplemented with 30 μg/ml gentamicin and 15 μg/ml tetracycline (FIG. 9A).

Enzyme assay was performed at 25° C. using ABTS (2,2'-azino-bis (3-ethylbenzothiazoline-6-sulphonic acid, Sigma-Aldrich, St. Louis, Mo.) as the substrate with BioTek spectrophotometer. The assay reactions were performed in 300 μl mixture containing 50 mM sodium acetate buffer at pH 4.5, 0.5 mM $H_2O_2$, 2.5 mM ABTS, and 150 μl extracellular supernatants from A514/pGPbpDyp2, A514/pGOprIDyp2, A514/pGOprFDyp2, and A514/pGPelBDyp2 transformants, respectively. Activity was monitored by an increase in absorption at 420 nm ($\varepsilon_{420}=36$ mM$^{-1}$ cm$^{-1}$) (Shi et al., *Biotechnol Biofuels* 6:1, 2013). All experiments were carried out in triplicate.

Example 5

Proteomics-Guided Biodesign of an Aromatic Compound Utilization Module

Figure 7A:
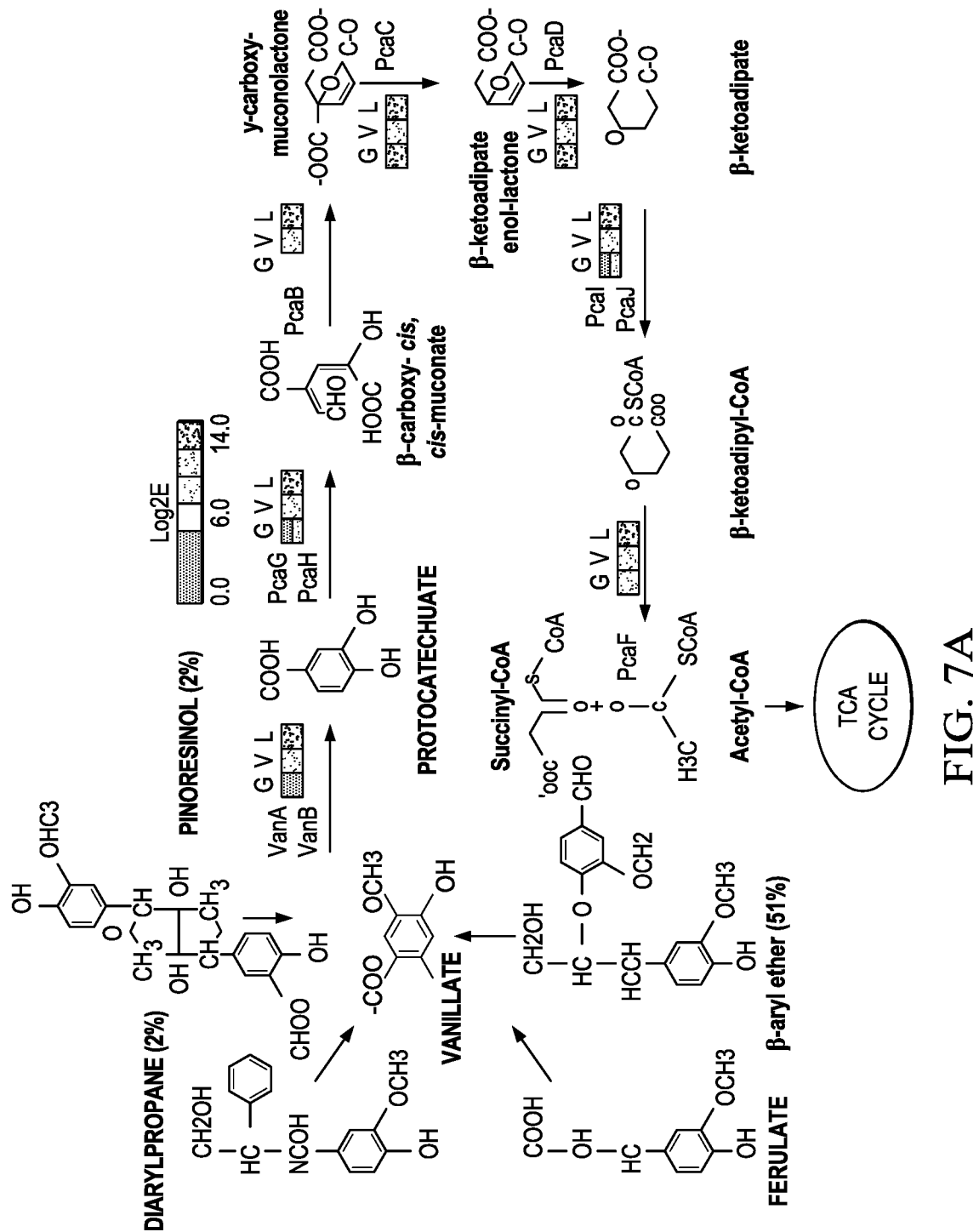
FIG. 7—Shows a biodesign of aromatic compound utilization module as well as a PHA synthesis module. (A) Protein expression in aromatic compound degradation pathways when A514 was grown in M9 medium containing either glucose, VA, or lignin. $\log_2$ E represents log (base 2) protein expression levels. (B) Growth curves and vanillate degradation curves of *P. putida* A514 having either the pPROBE-GT plasmid containing only the van promoter (control), or the promoter and the vanAB genes. Strains were grown in M9 medium with 50 mM vanillate as the sole carbon source. (C) PHA synthesis pathway and related fatty acid degradation pathway. Data showed the protein levels of the corresponding enzymes when *P. putida* A514 is grown in M9 medium containing either glucose, VA, or lignin. Log 2R represents log (base 2) expression ratio. V/G: Log 2(protein expression level under vanillic acid/protein expression level under glucose), L/G: Log 2(protein expression level under lignin/protein expression level under glucose). (D) PHA titer for the engineering strains ($A_{Pvan}$, $A_{phaJ4C1}$, and $A_{phaJ4C2}$). Strains were grown in M9 medium with 15 mM vanillate. The nitrogen concentration under N excess is 1 g/L, whereas N starvation is 65 mg/L.

Lignin depolymerization is the initial step in lignin degradation, resulting in the formation of various biaryl (e.g., β-aryl ether and biphenyl) and monoaryl compounds (e.g., ferulate, vanillin, and syringate). As shown by comparative genomics, these aromatic compounds could be degraded by a variety of peripheral pathways that funnel the structurally diverse substrates into a few key aromatic intermediates such as VA (FIG. 4). These aromatic intermediates could then be ring-cleaved and converted to central metabolites including acetyl-CoA and TCA intermediates via 'central' catabolism pathways such as the protocatechuate and catechol branches of β-ketoadipate pathways (Jiménez et al., in Handbook of Hydrocarbon and Lipid Microbiology, K. Timmis, Ed., Springer Berlin Heidelberg, pp. 1297-1325, 2010; Jiménez et al., *Environ Microbiol* 4:824, 2002). Proteomic analysis validated the comparative genomics by showing that several of the pathways described above were coordinately up-regulated when *P. putida* A514 was grown on lignin as the carbon source (FIGS. 2D and 4). In particular, both the protocatechuate and catechol branched β-Ketoadipate pathways played important roles for catabolizing phenylpropenoids from lignin (Jiménez et al., in Handbook of Hydrocarbon and Lipid Microbiology, K. Timmis, Ed., Springer Berlin Heidelberg, pp. 1297-1325, 2010). In particular, key enzymes in the peripheral pathways to convert coniferyl alcohol and p-coumarate to the central intermediates like VA or 4-hydroxybenzoate were also up-regulated in the presence of lignin. These enzymes included CalA (PputA514_0647), CalB (PputA514_0648), Fcs (PputA514_0649), Ech (PputA514_0651), and Vdh (PputA514_0650) (FIGS. 2D and 3). The VA and 4-hydroxybenzoate could then be funneled to the protocatechuate branch of the β-ketoadipate pathway, because enzymes in the protocatechuate branch of β-ketoadipate pathway (e.g. VanAB, PcaGH, PcaI and PcaJV) were up-regulated under VA and lignin treatment (FIGS. 2D, 3, and 7A). The coordinative up-regulation of peripheral pathways and the protocatechuate branch of the β-ketoadipate pathway in the presence of both VA and lignin indicated that VA may serve as a central intermediate toward degradation of some lignin-derived aromatic compounds in *P. putida* A514.

As shown in FIGS. 4 and 7A, VA is the first central metabolite in the protocatechuate branch of the β-ketoadipate pathway, where β-aryl ether, biphenyl, and ferulate could all be funneled to VA to be catabolized (FIG. 4) (Masai et al., *Biosci Biotechnol Biochem* 71:1, 2007). Considering the active β-ketoadipate pathway under lignin and VA treatment, and the amount of aromatic compounds catabolized by the pathway, it was thought that enhancing the expression of first two enzymes of β-ketoadipate pathway for VA degradation will increase the aromatic compound utilization capacity and promote cell growth in *P. putida* A514. Proteomics data suggested that the enzymes VanA and VanB were specifically induced in the presence of VA (FIG. 7A), although the absolute levels of these proteins was lower than the levels of most housekeeping proteins. Thus, an aromatic compound degradation module was designed by over-expressing vanAB.

Figure 7C:
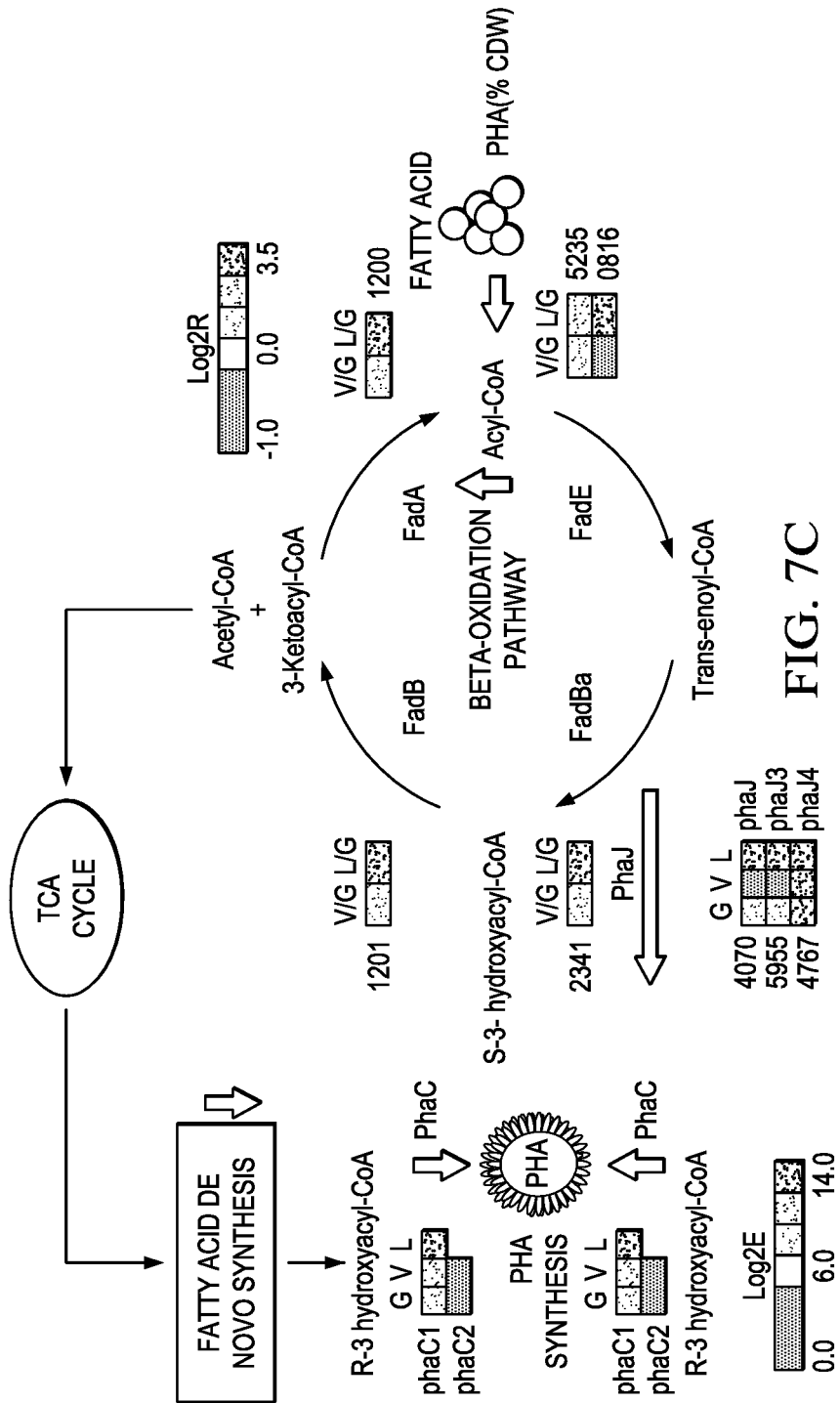

For the VA degradation assay, cells were grown in M9 minimal medium containing corresponding concentrations of VA (FIGS. 7C and 8). At the indicated time points, the 1-ml cell cultures were centrifuged for 5 min at 16,000×g, and the concentration of VA in the supernatant was measured via absorbance at 289 nm as previously described (Thanbichler et al., *Nucleic Acids Res* 35:e137, 2007).

In order to overexpress vanAB, these genes were cloned into the plasmid pPROBE-GT, and transformed into *P. putida* A514 to generate the $A_{van}$ strain. The $A_{van}$ strain showed significantly improved growth and VA degradation (FIG. 7B). The cell density increased from OD 3 to 4 for the $A_{van}$ strain as compared to the empty vector control (FIG. 7B). Similarly, the growth rate of the strain increased by about 25% compared to the control, when grown on VA as the sole carbon source (FIG. 7B). In addition, the VA degradation rate was improved on both 25 mM and 50 mM vanillic acid (FIGS. 7B and 8). The increased cell growth and VA degradation in the $A_{van}$ strain validated the important functions of VanAB and β-ketoadipate pathways in aromatic degradation in *P. putida* A514. In addition, the design was further integrated with lignin depolymerization and PHA production modules to achieve lignin to PHA production.

Example 6

Exploiting the Molecular Links Between Aromatic Compound Catabolism and PHA Synthesis to Improve PHA Titer In order to design the entire lignin-to-PHA route, carbon utilization and PHA biosynthesis on lignin substrate was further investigated. As shown in FIG. 7C, mostly PHA biosynthetic proteins (PhaC1, PhaC2, PhaJ, PhaJ4, PhaF, and PhaI) were all expressed under nitrogen excess with different carbon sources, suggesting active PHA production under nitrogen excess conditions (FIG. 7C). This is significantly different from some other *P. putida* strains, which do not accumulate PHA without inorganic nutrient limitations (Nikodinovic-Runic et al., *Microbiology* 155:3348, 2009). However, as shown in FIG. 7D, the baseline PHA production under nitrogen excess is low.

More importantly, proteomics analysis revealed that the β-oxidation pathway for fatty acid degradation was more active under VA and lignin than that under glucose (FIG. 7C). *P. putida* strains rely on the fatty acid β-oxidation or de novo biosynthetic pathways to provide substrates for mcl-PHA (middle chain length-PHA) biosynthesis (Prieto et al., in *Pseudomonas*, J.-L. Ramos, A. Filloux, Eds., Springer Netherlands, pp. 397-428, 2007). According to proteomics, the activated β-oxidation might provide CoA thioesters for PHA biosynthesis using carbon from aromatic compound or lignin catabolism. This provided a unique opportunity to enhance carbon flux from β-oxidation to PHA biosynthesis during lignin conversion. The PHA biosynthesis functional module thus was designed by over-expression of two key PHA biosynthesis genes to enhance the carbon flux from fatty acid oxidation to PHA biosynthesis. First, an (R)-specific enoyl-CoA hydratase (PhaJ, PputA514_4070, 4767, and 5955) was over-expressed to channel 3-hydroxyacyl-CoA precursors from fatty acid oxidation to PHA biosynthesis (FIG. 7C). Second, PHA polymerase PhaC (PputA514_5834 and 5836) was over-expressed to increase PHA production, as this enzyme catalyzes the PHA formation from precursors (FIG. 7C). However, both enzymes are encoded by redundant genes in the *P. putida* A514 genome. The genome has 3 phaJ genes and 2 phaC genes, which complicated the biodesign process. Proteomics analysis among different carbon sources helped to pinpoint PhaJ4 (PputA514_4767) and PhaC1 (PputA514_5834) as the key enzymes for PHA synthesis, due to their higher expression relative to the other paralogs (FIG. 7C).

Engineered strains overexpressing phaJ4 and phaC1 ($A_{phaJ4C1}$) were characterized for PHA production. Both the control strain (*P. putida* A514 carrying pPROBE-GT plasmid containing only the van promoter, $A_{Pvan}$) and the engineered strain overexpressing phaJ4 and phaC2 (AphaJ4C2) were used as reference strains to compare with $A_{phaJ4C1}$. The results confirmed the proteomics outcome in several ways. First, all strains growing on VA under N excess conditions produced PHA to a certain degree, though yield was higher under N starvation (FIG. 7D). Second, PHA production in $A_{phaJ4C1}$ is higher than $A_{phaJ4C2}$, confirming the role of PhaJ4 and PhaC1 as key players for PHA biosynthesis when *P. putida* A514 was grown on VA and lignin substrates. Third, a significant improvement in PHA titer and PHA percentage in cells was found for $A_{phaJ4C1}$ strains. Under nitrogen limitation, PHA content increased to 71% per cell dry weight (CDW) in $A_{phaJ4C1}$ and 58% in $A_{phaJ4C2}$, both of which are increased relative to the 39% in the control strain. Even under nitrogen excess, PHA content for $A_{phaJ4C1}$ reached 39%, which is higher than the 29% seen in the control strain. The increased PHA yield in $A_{phaJ4C1}$ under both N excess and N starvation conditions were statistically significant. These results again validated the activated β-oxidation on lignin substrate and the effectiveness of channeling carbon from fatty acid β-oxidation to PHA production. Since the PHA titer in $A_{phaJ4C1}$ is better than $A_{phaJ4C2}$, phaJ4 and phaC1 were used for the integration of three functional modules.

The design of three previously described functional modules not only validated the mechanisms revealed by the comparative genomics and proteomics analyses, but also enabled the integration and construction of consolidated lignin processing (CLP) in *P. putida* A514 for lignin-to-PHA bioconversion. The three functional modules addressed key metabolic steps for lignin-to-PHA production: lignin depolymerization, aromatic compound catabolism, and PHA synthesis. The plasmid pTDV was built to carry Dyp2 and vanAB for lignin depolymerization and aromatic compound catabolism modules, whereas plasmid pGJ4C1 contained the PHA biosynthesis module (FIG. 9A). These plasmids were co-transformed into *P. putida* A514, producing recombinant strain $A_{DVJ4C1}$ for the integration of three functional modules (FIG. 9A).

Figure 9B:
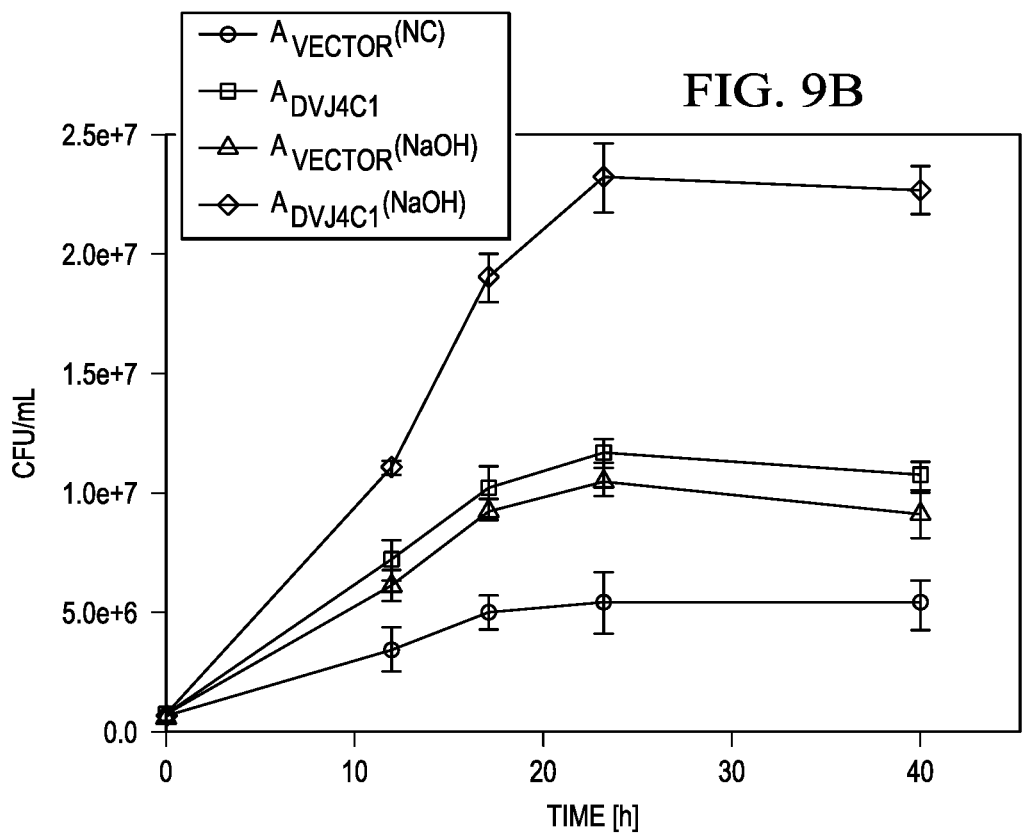

The integration of three functional modules further validated the lignin utilization mechanisms in *P. putida* A514 and proved the concept for a consolidated lignin-to-PHA process from several aspects. First, the $A_{DVJ4C1}$ strain showed significant improvement in growth, about 4-fold higher than the control strain $A_{vector}$, as measured by CFU under optimized conditions (FIG. 9B). These results demonstrated that the integration of lignin depolymerization and aromatic compound catabolism modules promoted cell growth on lignin as the carbon source. Second, the $A_{DVJ4C1}$ strain led to more lignin degradation as compared to the control strain according to the $^{31}$P NMR analysis (FIG. 9C). As shown in FIG. 9C, the phenolic functional groups showed different levels of degradation, with 0-5 phenolic group decreased most significantly. The result further confirmed that enhanced cell growth resulted from degradation of lignin polymer (FIG. 9C).

Figure 9D:
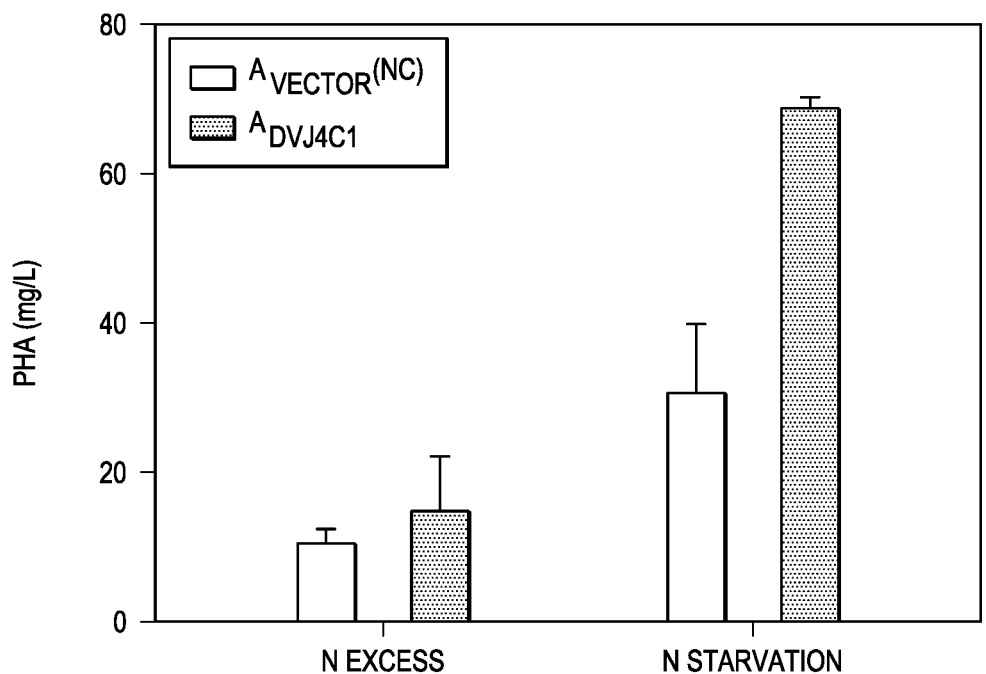
Figure 9C:
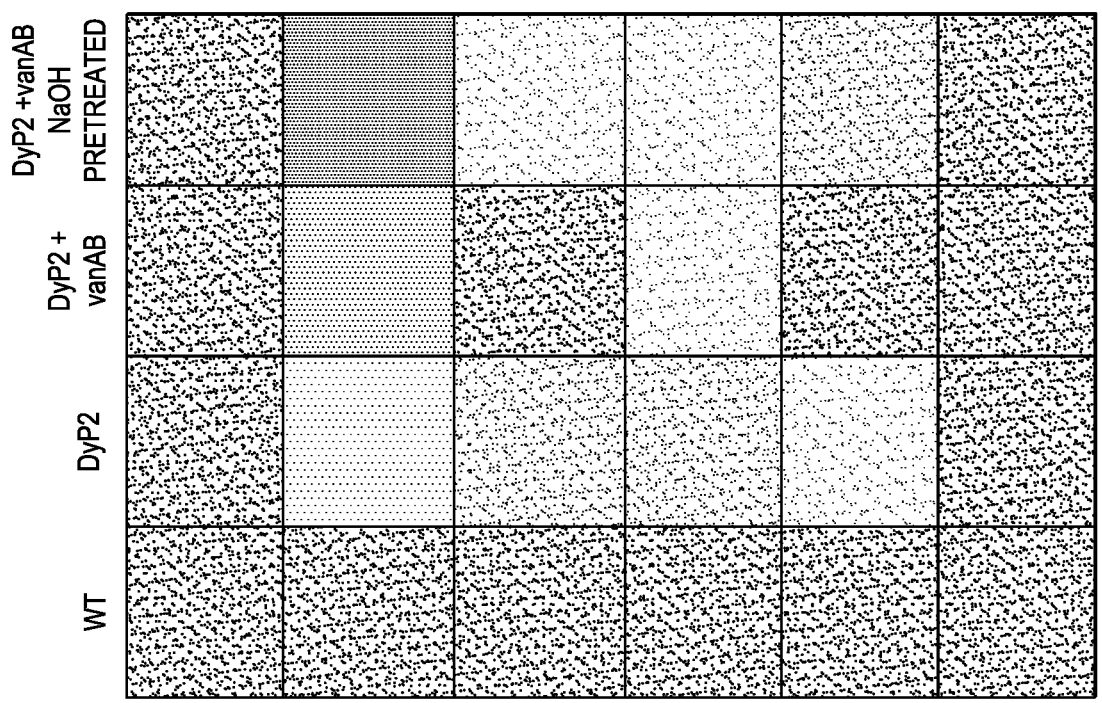

Third, the integrated strain $A_{DVJ4C1}$ increased PHA yield from lignin by more than 2-fold as compared to the control strains (FIG. 9D). Fourth, composition analysis by GC/MS revealed that a majority of PHA produced from lignin was mcl-PHA, the type of PHA with higher market value (Poirier et al., *Nat Biotechnol* 13:142-150, 1995). In particular, under N starvation condition, the C12 3HTD reached about 55% and the combination of C10 and C12 was at about 80% (Table 3). Considering the higher value for mcl-PHA, the results highlighted the potential for the new consolidated platform to contribute to the sustainability and economic viability of lignocellulosic biorefinery.

TABLE 3

GC analysis of the composition of medium-chain-length (mcl) PHA produced by recombinant *P. putida* A514 strains.

| PHA substrate | Strains | Culture | PHA Composition (mol %) | | | | | |
|---|---|---|---|---|---|---|---|---|
| | | | 3HHx (C6) | 3HO (C8) | 3HD (C10) | 3HDD (C12) | 3HTD (C14) | 3HHD (C16) |
| Vanillate | $A_{vector}$ | Low N | 7.06 ± 2.68 | 19.04 ± 3.48 | 33 ± 4.52 | 30.85 ± 1.11 | ND | 10.05 ± 2.04 |
| | $A_{JC1}$ | (65 mg/L) | 3.22 ± 0.14 | 30.14 ± 2.7 | 2.49 ± 0.07 | 15.13 ± 3.24 | ND | 49.02 ± 4.45 |
| | $A_{JC2}$ | | ND | 38.93 ± 2.41 | ND | 53.06 ± 4.29 | ND | 8.01 ± 0.21 |
| | $A_{vector}$ | High N | ND | ND | 34.78 ± 2.91 | 65.22 ± 1.24 | ND | ND |
| | $A_{JC1}$ | (1 g/L) | ND | ND | ND | 59.30 ± 1.10 | 38.78 ± 0.87 | 1.92 ± 0.24 |
| | $A_{JC2}$ | | ND | ND | 27.02 ± 3.33 | ND | 72.98 ± 2.64 | ND |
| Lignin | $A_{vectors}$ | Low N | 3.36 ± 1.87 | ND | ND | 96.64 ± 1.87 | ND | ND |
| | $A_{JC1DYP2}$ | (65 mg/L) | 4.29 ± 0.63 | 15.16 ± 2.72 | ND | 25.66 ± 12.79 | 54.89 ± 9.92 | ND |
| | Avectors | High N | 15.32 ± 3.63 | 19.16 ± 4.32 | ND | 50.05 ± 5.35 | 15.46 ± 3.61 | ND |
| | $A_{JC1DYP2}$ | (1 g/L) | 22.64 ± 13.8 | 5.12 ± 2.21 | ND | 57.23 ± 5.08 | 24.12 ± 19.5 | ND |

Example 7

Integration of Multiple Functional Modules for Consolidated Lignin Processing (CLP) for Lignin-to-PHA Bioconversion For extraction of PHA as described above, liquid cultures (100 ml) were centrifuged at 9,000 rpm for 15 min at 4° C., washed twice with 15 ml Nanopure water, and lyophilized for a minimum of 24 h. The lyophilized cells were added with chloroform at a ratio 1:15 (w/v) and shaken at 60° C. and 120 rpm overnight to extract polymer produced in the cells. The chloroform solution was filtered to remove any cell debris and concentrated by rotary evaporation. PHA was precipitated by adding a 10-fold volume of pre-chilled methanol. The methanol-chloroform mixture was decanted and the pure polymer was washed with fresh iced methanol. To obtain the pure product, the precipitant was then re-dissolved in chloroform and the process was repeated for clean-up. The collected PHA was dried at 25° C. in vacuum dryer to remove all residual solvent. The PHA content (wt %) was calculated as the percentage of the cell dry weight (CDW) represented by the poly-(3-hydroxyalkanoates) (Wang et al., *Process Biochem* 44:106-111, 2009; Wang et al., *Appl Environ Microbial* 78:519-527, 2012).

For GC/MS analysis of PHA composition, cell materials were prepared and lyophilized as described above. The dry cells (~15 mg) were dissolved in 2 ml of methanol-sulfuric acid (85:15) solution and 2 ml chloroform containing 0.01 mg/ml 3-methylbenzoic acid (internal standard), and then incubated at 100° C. for 4 h. After cooling, 1 ml of demineralized water was added and the organic phase, which contained the resulting methyl esters of monomers. The organic phase was filtered and analyzed by a GC/MS 2010 SE plus Gas Chromatograph (Shimadzu, Japan) as previously described (Wang et al., *J Biosci Bioeng* 110:653-659, 2010). All experiments were performed in triplicate Overall, the systems biology-guided biodesign uniquely elucidated and validated the molecular and systems level mechanisms including: the DYP-based system in *P. putida* A514 for lignin depolymerization; the essential role of β-ketoadipate pathway in lignin degradation; and the carbon flux channeling from fatty acid β-oxidation to PHA production. Each of the three functional modules was designed to validate the mechanisms as revealed by systems biology. Not only did the functional modules validate the hypothesis and mechanisms, but also the functional modules were integrated to prove the concept for consolidated lignin bioconversion to a fungible bioproducts. The knowledge-based biodesign offered a novel approach for future design of lignin bioconversion. Further improvement can be achieved by enhancing each of the functional modules including developing a more comprehensive lignin depolymerization enzymatic system, over-expressing key regulators for aromatic compound utilization, and optimizing the fermentation of PHA. The consolidated processing integrating lignin depolymerization, aromatic compound catabolism, and target compound production can also be applied to the production of many different products from lignin, an important biorefinery waste stream and abundant feedstock.

All NMR experiments described herein were carried out using a Bruker Avance-400 spectrometer operating at a frequency of 100.59 MHz for $^{13}$C (Hallac et al., *Energy & Fuels* 24:2723-2732, 2010; Pu et al., *Bioenerg Res* 2:198-208, 2009). HSQC spectra were acquired using deuterated dimethyl sulfoxide (500 µL) as solvent for lignin samples (~60-100 mg) at 45° C. with the following acquisition conditions: 11-ppm spectra width in F2 ($^1$H) dimension with 2048 data points (232.7-ms acquisition time), 220-ppm spectra width in F1 ($^{13}$C) dimension with 256 data points (5.8-ms acquisition time); a 1.5-s pulse delay; a $^1J_{C-H}$ of 145 Hz; and 96 scans. The central solvent peak ($\delta_C$ 39.5 ppm; $\delta_H$ 2.5 ppm) was used for chemical shift calibration. For quantitative $^{31}$P NMR analysis, lignin (~20 mg) was dissolved in a solvent of pyridine/CDCl$_3$ (1.6/1.0 v/v, 500 µL) and derivatized with 2-chloro-4,4,5,5-tetramethyl-1,3,2-dioxaphospholane (Pu et al., *Energy Environ Sci* 4:3154-3166, 2011). The spectrum was acquired using an inverse-gated decoupling pulse sequence (Waltz-16), a 90° pulse, and a 25-s pulse delay, and 128 scans were accumulated for each sample. NMR data were processed using the TopSpin 2.1 software (Bruker BioSpin) and MestreNova (Mestre Labs) software packages.

Example 8

Synergistic Enzymatic and Microbial Conversion of Lignin for Lipid-Strain and Culture Medium

*Rhodococcus opacus* PD630 was purchased from the German Collection of Microorganisms and Cell Cultures. The *Rhodococcus* Minimal (RM) medium for lignin fermentation was modified from a previous study (Kurosawa et al., *J. Biotechnol.* 147:212-218, 2010), which contained per liter: 5 g alkali lignin (Sigma-Aldrich, USA), 1.4 g (NH$_4$)$_2$SO$_4$, 1.0 g MgSO$_4$.7H$_2$O, 0.015 g CaCl$_2$.2H$_2$O, 1.0 ml trace element solution, 1.0 ml stock A solution, and 35.2 ml 1.0 M phosphate buffer.

Example 9

Lignin Fermentation

The seed culture was prepared by inoculating a single colony of *R. opacus* PD630 into 20 mL Tryptic Soy Broth (TSB) medium, and cultivated at 28° C. to OD$_{600}$ 1.5. The cultured strain were harvested by centrifuging and washed twice with equal volume of RM medium without lignin. The washed cells were resuspended in 20 ml RM medium without lignin. One milliliter of resuspended cells were added to 100 ml of lignin fermentation medium. For laccase and Fenton reaction treatments, the enzyme and chemicals were added at the same time of strain inoculation. Fermentation was conducted by cultivating at 28° C. with shaking speed of 200 rpm for 144 hours.

Example 10

Lignin Concentration Analysis by Prussian Blue Assay

After fermentation by *R. opacus* PD630, the pH of the lignin culture was adjusted to 12.5 with 10 M NaOH to completely dissolve the lignin. In order to completely dissolve lignin, the lignin sample was mixed at speed of 180 rpm under room temperature for 1 hr. The total volume was adjusted to 100 mL by adding RM medium without lignin. The samples were further diluted to an optimal concentration using ddH$_2$O to adjust the final absorbance at 700 nm to be within the range of 0.7-1.5. For the Prussian Blue assay, 1.5 mL of the diluted sample was mix with 100 µL of 8 mM K$_3$Fe(CN)$_6$ and 100 µl 0.1 M FeCl$_3$. After exactly 5 min of reaction, the absorbance of the reaction solution at 700 nm was recorded by UV/vis spectrophotometer. A standard curve was established with the same reagents and a known concentration of lignin. All experiments were carried out in triplicate.

Example 11

Cell Concentration Determination

To determine the number of living cells, 100 µl of fermentation culture was serial diluted and plated on tryptic soy agar plates. The numbers of colonies were counted from the plates and converted to colony forming unit/ml (CFU/ml).

Example 12

Total Lipid Extraction

In order to determine the total lipid produced by *R. opacus* PD630, 100 mL fermentation culture was filtered through two layers of cheese cloth and washed twice with 100 mL ddH$_2$O to remove the lignin. The cells were collected by centrifuging the totally filtered 300 mL. The pelleted cells were lyophilized for 24 hours. Three milliliters chloroform:methanol (2:1) solution were added to cells to homogenize the cells for 3 hours, followed by centrifugation at 3000 rpm to pellet the cells. The supernatant was then transferred to new weighted tubes and 0.6 mL distilled water were added. After phase separation, the upper phase was discarded. The organic phase containing total lipid was rinsed with chloroform:methanol:water (3:48:47). The upper phase was removed and the organic phase was dried down under N$_2$ stream and the lipid was weighed.

Example 13

Lignin Gel Permeation Chromatography Analysis

The lignin gel permeation chromatography (GPC) analysis was performed after acetylation on a PSS-Polymer Standards Service (Warwick, R.I., USA) GPC SECurity 1200 system featuring Agilent HPLC 1200 components equipped with four Waters Styragel columns (HR1, HR2, HR4 and HR6) and an UV detector (270 nm). Lignin was acetylated in a mixture of acetic anhydride/pyridine (1:1 v/v, 2.0 mL) for 24 h at room temperature. The reaction mixture was diluted with ethanol (30 mL) and stirred for 30 min, and then concentrated under lower pressure. The addition and removal of ethanol was repeated to remove trace acetic acid and pyridine from the samples. The samples were then dissolved in chloroform and added dropwise into diethyl ether to precipitate the samples followed by centrifugation. After air drying, the acetylated samples were dried for 24 h in a vacuum oven at 40° C. prior to GPC analysis. Tetrahydrofuran was used as the mobile phase in GPC analysis and the flow rate was 1.0 mL/min. The molecular weight of the derivatized lignin sample was acquired by using a calibration curve established with standard narrow polystyrene samples.

Example 14

Lignin Structure Analysis by Nuclear Magnetic Resonance

All NMR experiments were carried out at a Bruker Avance 400-MHz NMR spectrometer. HSQC spectra were acquired using deuterated dimethyl sulfoxide (500 μL) as solvent for lignin samples (~60-100 mg) at 45° C. with the following acquisition conditions: 11-ppm spectra width in F2 ($^1$H) dimension with 2048 data points (232.7-ms acquisition time), 220-ppm spectra width in F1 ($^{13}$C) dimension with 256 data points (5.8-ms acquisition time); a 1.5-s pulse delay; a $^1J_{C-H}$ of 145 Hz; and 96 scans. The central solvent peak ($\delta_C$ 39.5 ppm; $\delta_H$ 2.5 ppm) was used for chemical shift calibration. For quantitative $^{31}$P NMR analysis, lignin (~20 mg) was dissolved in a solvent of pyridine/CDCl$_3$ (1.6/1.0 v/v, 500 μL) and derivatized with 2-chloro-4,4,5,5-tetramethyl-1,3,2-dioxaphospholane. The spectrum was acquired using an inverse-gated decoupling pulse sequence (Waltz-16), a 90° pulse, and a 25-s pulse delay, and 128 scans were accumulated for each sample. NMR data were processed using the TopSpin 2.1 software (Bruker BioSpin) and MestreNova (Mestre Labs) software packages.

Example 15

Laccase Treatment Significantly Promotes Cell Growth on Lignin

Figure 11A:
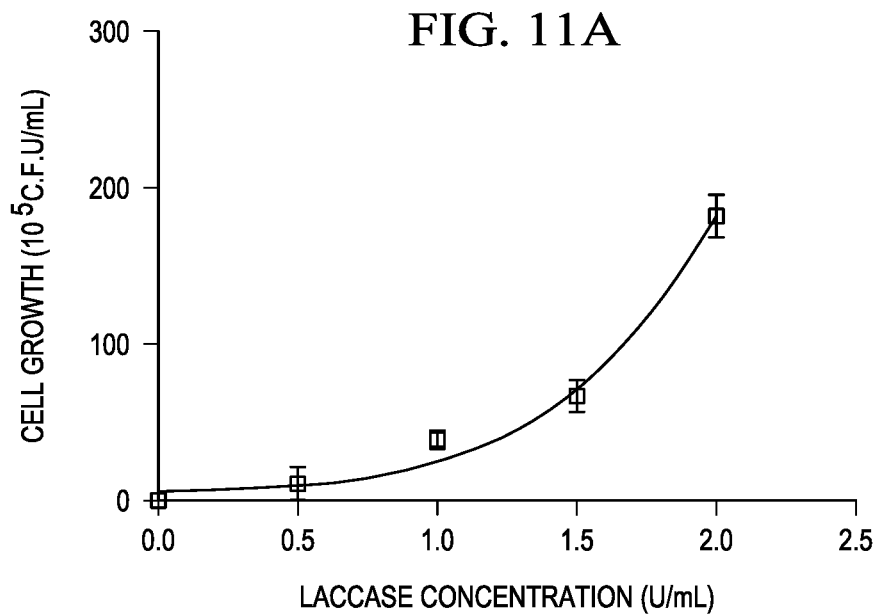
FIG. 11—Shows the increase of cell growth in response to laccase and other treatment. A) Laccase promotes *R. opacus* PD630 cells growth using lignin as a carbon source.

Laccase treatment significantly promoted the cell growth of *R. opacus* PD630 on lignin. As shown in FIG. 11, the enzymatic treatment significantly promoted *R. opacus* PD630 cell growth on kraft lignin as the sole carbon source. The CFU of *R. opacus* PD630 cells after six days of growth increases exponentially in response to the activity of laccase in the enzyme-cell system. The cell growth was very slow without laccase treatment due to the relatively low initial inoculation. However, with the increased concentration of laccase, the CFU after six days of cultivation can achieve an exponential increase to 1.85×10$^7$/ml at 2 U/ml of laccase treatment. Considering that kraft lignin is mostly insoluble, laccase treatment might lead to the depolymerization and solubilization of lignin to provide more carbon source for *R. opacus* PD630 cells, which in turn promoted the cell growth. However, the exponential increase of cell growth in response to laccase level cannot be fully explainable by lignin degradation by laccase. The result clearly indicated the synergy between laccase and cells, and such synergy was confirmed by chemical analysis.

Example 16

Fenton Reaction has Less Synergy with Cell System

Figure 11B:
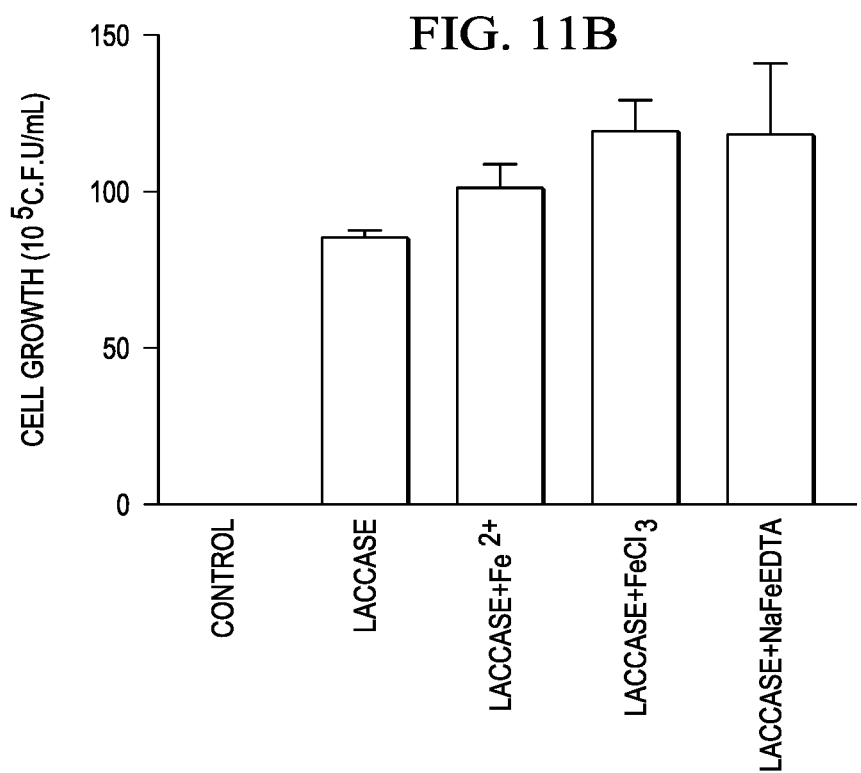

As described above, the Fenton reaction is another type of widely studied lignin degradation mechanisms (Xie et al., *Green Chemistry*, 2015). The Fenton reaction is believed to play an important role for lignin depolymerization in the termite gut and wood-degrading fungus (Xie et al., *Green Chemistry*, 2015; Brune, *Nat Rev Micro* 12:168-180, 2014; Vanden Wymelenberg et al., *Appl Environ Microbiol* 76:3599-3610, 2010; Martinez et al., *PNAS USA* 106:1954-1959, 2009). It was then determined whether a synergistic effect can be achieved for laccase treatment and Fenton reaction during bacterial lignin conversion. The classic model for the Fenton reaction is that ferrous iron is oxidized by hydrogen peroxide to ferric iron, forming hydroxyl radical which could attack lignin. Nevertheless, bacterial cells also have Quinone reductase systems that can recycle ferric iron to ferrous iron. Considering that some iron ions may lead to the precipitation of lignin, the chelated iron ions were also used in the Fenton reaction experiment (Wang et al., *Science in China Series C: Life Sciences* 51:214-221, 2008; Henriksson et al., *Applied Microbiology and Biotechnology* 42:790-796, 1995). Taking these into consideration, different types of iron ions and H$_2$O$_2$ were combined with laccase treatment to study their effect on lignin conversion by *R. opacus* PD630. As shown in FIG. 11B, different types of iron ions have limited effects in promoting lignin degradation when combined with laccase treatment. As shown in FIG. 11B, even though all types of iron-laccase combination treatment increased the CFU at six days after fermentation, the impact on cell growth is marginal compared to that of laccase treatment. In addition, there is no significant difference among different types of iron used in the treatment. Even though some synergy can be found for the Fenton reaction, laccase, and cell system, the results indicated that laccase by itself has a much stronger synergy with *R. opacus* PD630 for lignin degradation as compared to that of Fenton reaction. In nature, the Fenton reaction depends on quinones and other mediators, as well as the enzyme system to regenerate these mediators, to eventually reduce the ferric iron to ferrous iron to be used in the reaction. In addition, radicals like $H_2O_2$ are necessary for an effective Fenton reaction. The relatively limited synergistic effects between laccase and the Fenton reaction might be due to the lack of a sustainable radical or chemical mediator regeneration system. Moreover, it seems that the radicals generated by laccase did not contribute significantly to the Fenton reaction. The synergy as shown by cell growth was further confirmed by the chemical analysis of lignin structure during the fermentation.

Example 17

Changes of Lignin Molecular Weight During Cell-Enzyme Co-Fermentation

Comprehensive lignin characterization was carried out to determine the key factors contributing to synergistic effects between laccase and *R. opacus* PD630 cells. GPC (gel permeation chromatography) analysis was carried out to evaluate the changes of molecular weight under different fermentation conditions (Ben et al., *RSC Advances* 2:12892-12898, 2012). Five different conditions were compared as shown in Tables 6 and 7, and FIG. 12, and these conditions included a reference lignin sample without any bacterial or enzymatic treatment (no cells, Treatment I), lignin after bacterial fermentation (cells only, Treatment II), lignin after bacterial fermentation with laccase treatment (cell+laccase, Treatment III), lignin after bacterial fermentation with laccase and ferrous iron treatment (cell+laccase+ferrous iron, Treatment IV), and lignin after bacterial fermentation with enzymatic and Fenton reaction treatment (cell+laccase+ferrous iron+$H_2O_2$, Treatment V). These five fermentation conditions represented different combinations of bacterial, enzymatic, and chemical treatments, including *R. opacus* PD630 only, *R. opacus* PD630 with laccase enzyme, and *R. opacus* PD630 with both laccase and the Fenton reaction.

As shown in Table 4, laccase treatment (Treatment III) led to the most significant increase in molecular weight as compared to the cell-only (Treatment II) and no-cell reference (Treatment I). The number average molecular weight ($M_n$) for cell-only fermentation (Treatment II) was not significantly different from no-cell reference (Treatment I), indicating that *R. opacus* PD630 has limited capacity for lignin depolymerization. However, a significant increase in $M_n$ was observed when adding laccase into the fermentation (Treatment III vs. Treatment II). No significant differences in $M_n$ were found among Treatments III, IV, and V, indicating limited synergy of the Fenton reaction and laccase on lignin degradation. In addition, even though the Polydispersity index and $M_w$ had relatively larger variation, the trends were the same as $M_n$, where laccase led to the most significant increase in molecular weight. This increase could be due to two reasons. First, laccase treatment may have significantly improved the usage of low molecular weight lignin, when combined with *R. opacus* PD630 fermentation. Second, the increase of $M_w$ and $M_n$ may also be due to the polymerization of low molecular weight lignin caused by laccase. However, the increased cell growth and lignin consumption, as well as the subsequent NMR analysis all indicated that laccase and *R. opacus* PD630 synergy led to more efficient depolymerization and consumption of low molecular weight lignin.

TABLE 4

GPC analysis of lignin molecular weights upon different treatment.

| Lignin Sample | $M_n$ | $M_w$ | Polydispersity index |
|---|---|---|---|
| I[a] | $1.73 \times 10^3$ | $8.08 \times 10^3$ | 4.66 |
| II[b] | $1.67 \times 10^3$ | $7.58 \times 10^3$ | 4.55 |
| III[c] | $2.12 \times 10^3$ | $2.68 \times 10^4$ | 12.7 |
| IV[d] | $2.15 \times 10^3$ | $3.30 \times 10^4$ | 15.3 |
| V[e] | $2.12 \times 10^3$ | $1.90 \times 10^4$ | 8.98 |

I[a] No cell
II[b] Cell only
III[c] Cell + Laccase
IV[d] Cell + Laccase + Fe
V[e] Cell + Laccase + Fe + $H_2O_2$

TABLE 5

Decrease of lignin functional groups after different treatments.

| Functional Group | Integration region (ppm) | Examples | hydroxyl contents/(mmol/g lignin) | | | | |
|---|---|---|---|---|---|---|---|
| | | | I[a] | II[b] | III[c] | IV[d] | V[e] |
| Aliphatic OH | 150.0-145.2 | | 2.38 | 2.32 | 1.88 | 1.98 | 1.99 |
| $C_5$ substituted condensed Phenolic OH | β-5 144.6-142.9 | | 0.15 | 0.02 | 0.02 | 0.01 | 0.01 |

TABLE 5-continued

Decrease of lignin functional groups after different treatments.

| Functional Group | Integration region (ppm) | Examples | hydroxyl contents/(mmol/g lignin) | | | | |
|---|---|---|---|---|---|---|---|
| | | | I[a] | II[b] | III[c] | IV[d] | V[e] |
| 4-O-5 | 142.9-141.6 | (structure) | 0.01 | 0.02 | 0.01 | 0.02 | 0.01 |
| 5-5 | 141.6-140.1 | (structure) | 0.00 | 0.05 | 0.02 | 0.03 | 0.03 |
| Guaiacyl phenolic OH | 140.1-138.8 | (structure) | 1.32 | 1.40 | 0.98 | 1.00 | 1.02 |
| Catechol type OH | 138.8-138.2 | (structure) | 0.04 | 0.02 | 0.01 | 0.02 | 0.02 |
| p-hydroxy-phenyl-OH | 138.2-137.3 | (structure) | 0.08 | 0.06 | 0.02 | 0.03 | 0.03 |
| Carboxylic acid OH | 136.6-133.6 | (structure) | 0.50 | 0.15 | 0.16 | 0.29 | 0.06 |

I[a] No cell
II[b] Cell only
III[c] Cell + Laccase
IV[d] Cell + Laccase + Fe
V[e] Cell + Laccase + Fe + $H_2O_2$ Example 18

Laccase and *R. opacus* PD630 Cells Synergized Lignin Degradation as Revealed by Functional Group Content Complementary to GPC analysis, comprehensive NMR analysis revealed that laccase and *R. opacus* PD630 cells synergistically degraded different chemical structures in lignin (Table 5). The changes of hydroxyl group content in lignin was determined by $^{31}P$ NMR spectra of the lignin derivatized with TMDP (2-chloro-4,4,5,5-tetramethyl-1,3,2-dioxaphospholane). TMDP reacts with the hydroxyl functional groups of lignin to form phosphitylated derivatives that can be detected by $^{31}P$ NMR (Pu et al., *Energy & Environmental Science* 4:3154-3166, 2011). In particular, the aliphatic hydroxyl, phenolic, and carboxylic acids groups of lignin were identified based on characteristic chemical shifts (Ben et al., *Energ Fuel* 25:2322-2332, 2011) and then quantified by peak integration. $^{31}P$ NMR spectra of the lignin samples from the five treatments described above were analyzed to evaluate how laccase, cells, and the Fenton reaction impacted lignin degradation. The abundance of various —OH groups was normalized by the internal standard NHND (endo-N-hydroxy-5-norbornene-2,3-dicarboximide) using peak integration (Table 5).

*R. opacus* PD630 cells, laccase, and the Fenton reaction could all lead to lignin degradation as indicated by decreased functional group content from $^{31}P$ NMR analysis. As shown in Table 5, the degradation pattern can be classified into three categories. The first category included functional groups such as β-5 condensed phenolic OH and catechol-type OH, both of which were able to be degraded significantly by *R. opacus* PD630 cell-only treatment (Treatment II vs. I). These results demonstrated that *R. opacus* PD630 alone could cause lignin structural changes, yet the lignin degradation capacity is very limited in terms of the types of chemical bonds and the degree of functional group reduction.

The second category includes aliphatic OH, guaiacyl phenolic OH, and p-hydroxyl-phenyl OH groups. The abundance of these functional groups was significantly decreased with the addition of laccase into fermentation using *R. opacus* PD630 (Treatment III vs. II). For example, the degradation of the aliphatic OH group was increased from 2.5% to 21% after laccase treatment. More importantly, the two most abundant functional groups in lignin, aliphatic OH, and guaiacyl phenolic OH groups, were both in this category, with enhanced degradation mainly due to laccase treatment in fermentation. These results correlated with the GPC data and cell growth data, where laccase treatment had the most significant impact on lignin utilization and cell growth.

The third category mainly included carboxylic acid OH, which was decreased upon cell-only fermentation (Treatment I) and the addition of Fenton reaction reagents (Fe and $H_2O_2$, Treatment V). As shown in Table 5, the functional group was degraded by almost two-thirds after fermentation with *R. opacus* PD630 (Treatment II vs. I), yet remained unchanged upon laccase treatment (Treatment III vs. II). However, the addition of Fenton reaction agent (Treatment V vs. IV) promoted further degradation of the functional group, suggesting synergy of the Fenton reaction with cell treatment for the degradation of carboxylic acid groups.

Overall, the results revealed synergistic lignin degradation by *R. opacus* PD630 cell, laccase, and the Fenton reaction. Among the different treatments, the fermentation with laccase and cells together led to the significant degradation of the most abundant functional groups in lignin, such as aliphatic OH and guaiacyl phenolic OH. These results indicated that laccase and *R. opacus* PD630 could synergistically promote lignin degradation, which was consistent with the increased cell growth (FIG. 11) and lignin molecular weight upon laccase treatment (Table 4). The $^{31}$P NMR data was further validated by the lignin quantification using $^1$H-$^{13}$C heteronuclear single quantum coherence (HSQC) NMR analysis (FIG. 12) and Prussian Blue assay. Lignin degradation was significantly improved when fermented with both laccase and *R. opacus* PD630 cells. Even though the Prussian Blue assay is semi-quantitative for lignin quantification, the results correlated well with the $^{31}$P NMR and cell growth data, in that laccase and cells synergistically promoted lignin degradation and utilization.

The two dimensional (2D) $^1$H-$^{13}$C HSQC was also used to determine the mechanism of lignin degradation. HSQC spectra of lignin were measured for the treatments described above. The overlapping signals in one-dimensional NMR were readily resolved and clearly assigned to specific structure type. As shown in FIG. 12, the diagnostic signals in guaiacyl units (i.e., $G_2$, $G_5$, and $G_6$) for a softwood lignin were well observed at $\delta_C/\delta_H$ of 110.8/7.06, 115.1/6.78, and 119.8/6.81 ppm, with the existence of p-hydroxyphenyl (H) unit (i.e., its $C_{2/6}/H_{2/6}$ correlation signal $\delta_C/\delta_H$ around 128.1/7.20 ppm). In the aliphatic region of HSQC spectra, the interunit linkage of β-O-4 was evident with its signals at 71.2/4.81 ($C_\alpha/H_\alpha$, $A_\alpha$), 84.2/4.32 ($C_\beta/H_\beta$, $A_\beta$), and 59.8/3.48 ppm ($C_\gamma/H_\gamma$, $A_\gamma$), respectively. Signals for resinol (β-β linkage) subunits were also observed with its C/H correlations around $\delta_C/\delta_H$ 85.0/4.66 ($C_\alpha/H_\alpha$), 3.06/53.9 ($C_\beta/H_\beta$), and 70.9/3.78,4.15 ($C_\gamma/H_\gamma$) ppm in the HSQC spectra. Among all treated lignin samples, the cells plus laccase (Treatment III) treated lignin had the least signal intensities of H unit and resinol subunits (β-β linkage), suggesting a significant degradation of these lignin structures in the treated lignin. This further demonstrated that the synergy between cells and laccase had the most significant impact on lignin degradation. The cell plus laccase treatment (Treatment III) also resulted in lignin with the lowest relative abundance of end group cinnamyl alcohol (Cγ/Hγ correlation signal at $\delta_C/\delta_H$ 61.6/4.13 ppm), with its lowest signal intensity shown in the HSQC spectra. The reduction of cinnamyl alcohol would contribute to the decrease of aliphatic hydroxyl group content, which further supported the $^{31}$P NMR results that the lignin from the cell plus laccase treatment (Treatment III) had the lowest aliphatic hydroxyl group content.

Overall, the NMR and lignin quantification analysis revealed synergistic degradation of lignin by both *R. opacus* PD630 cells and laccase with the following features. First, the degradation of lignin by *R. opacus* PD630, laccase, and the Fenton reaction were functional group-specific. Unlike cellulose degradation with glucose as the single subunit, lignin is a heteropolymer with diverse aromatic monomer units (Xu et al., BMC Bioinformatics 8:1471-2105, 2009; Xie et al., Curr. Opin. Biotechnol. 27:195-203, 2014). These different monomers were further connected by various types of chemical bonds and linkages (Boerjan et al., Annu Rev Plant Biol 54:519-546, 2003). The three categories of functional groups as shown in Table 5 indicated that *R. opacus* PD630, laccase, and the Fenton reaction each degrade different chemical structures. The functional group-specific degradation by *R. opacus* PD630, laccase, and the Fenton reaction provided a basis for synergistic effects for cell-enzyme fermentation. In particular, the synergy between *R. opacus* cells and laccase provided an important and diverse capacity to achieve efficient lignin depolymerization and utilization, as the cellular system and laccase had different specificity for various types of chemical bonds.

Second, based on chemical analysis, laccase played an essential role for lignin degradation, because the enzyme specifically cleaves the most abundant chemical bonds in lignin. In particular, among the three categories of functional groups, both aliphatic OH and guaiacyl phenolic OH groups belonged to the category that was specifically degraded by laccase. The two functional groups represented two types of the most abundant chemical groups in lignin (Pu et al., J of Photochemistry and Photobiology A: Chemistry 163:215-221, 2004; Ghaffar et al., Biomass and Bioenergy 57:264-279, 2013). The selective degradation of abundant monomers by laccase was consistent with the cell growth and GPC data demonstrating that laccase led to the most significant changes.

Third, the strong synergy of laccase and *R. opacus* cells on lignin degradation indicated that the efficient consumption of monomers and oligomers generated by laccase promoted the depolymerization direction of the reaction. Laccase could catalyze both polymerization and depolymerization of lignin (Munk et al., Biotechnol. Adv 33:13-24, 2015; Lundquist et al., Biochem. J 229:277-279, 1985). The removal of depolymerization products might have promoted the reaction toward depolymerization rather than polymerization. Four aspects of data were consistent to support this conclusion, including the degradation of different functional groups as shown by $^{31}$P-NMR, the significant improvement of cell growth upon laccase treatment, the increases in molecular weight as shown by GPC, and the overall higher lignin consumption by the cell-laccase treatment.

Example 19

Simultaneous Depolymerization and Fermentation (SDF) Significantly Improved Lipid Production It has been established that R. opacus PD630 fermentation of lignin produces lipid, including TAG (triacylglycerol) as the biodiesel precursor (Kosa et al., Green Chemistry 15:2070-2074, 2013). The simultaneous depolymerization and fermentation (SDF) by the cell-enzyme system not only promoted cell growth and lignin degradation, but also led to significantly increased lipid production by 17-fold to 145 mg/L (FIG. 13). This increase in lipid content suggests that efficiently degraded lignin monomers provide R. opacus cells with sufficient carbon source to accumulate lipid.

Overall, this study demonstrated mechanisms for an effective synergy between R. opacus cells and laccase for lignin degradation at both the chemical processing and the cell growth levels. The synergistic lignin degradation for laccase and cells was revealed at both the chemical and biological levels in terms of selective degradation of different functional groups and increased cell growth. The mechanistic study could enable a SDF process to significantly improve lignin utilization and cell growth. As compared to the Fenton reaction, laccase treatment in this study had a much more significant impact on lignin degradation, probably due to the capacity to self-generate radicals. Other enzymes or reactions for lignin depolymerization often depends on a sustainable system to either generate radicals like $H_2O_2$ or quinones. Laccase thus not only serves as a good enzyme for SDF, but also can potentially be engineered for consolidated lignin processing.

Example 20

Figure 15A:
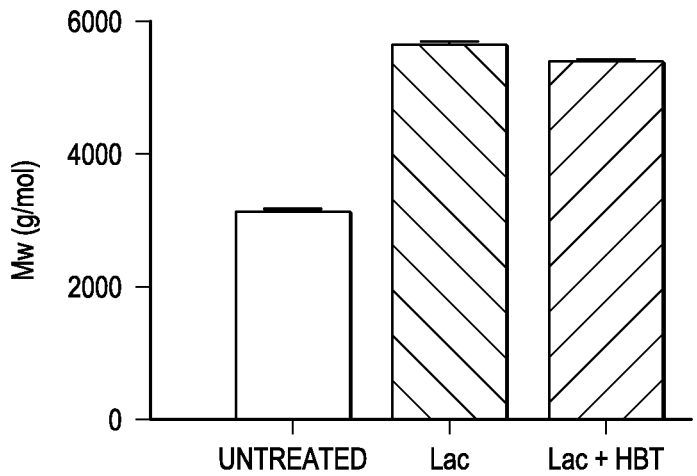

Enzyme-Mediator System Promotes Lignin Degradation by Promoting Enzymatic Lignin Depolymerization and Solubilization in a Mediator-Specific Way An efficient laccase-mediator system was first designed to solubilize >35% of insoluble kraft lignin. Kraft lignin is among the most recalcitrant and insoluble lignin. In general, laccase itself could only carry out oxidative attack on the phenol structure, which accounts for only a small portion of lignin.[13] To achieve effective lignin depolymerization, it is necessary to establish an efficient laccase-mediator system, where the electron mediator can facilitate the redox transfer during the oxidation by laccase and the subsequent non-enzymatic attack on non-phenolic lignin (FIG. 14).[13-15] However, different mediators may have various impacts on the laccase-based lignin depolymerization reaction and could promote either polymerization or depolymerization reactions. We first screened four different types of mediators in combination with a well-studied commercial laccase from Trametes versicolor. In order to well integrate with downstream bioconversion by bacteria Rhodococcus opacus PD630, the pH for lignin depolymerization by laccase-mediator system was adjusted to 7. As shown in FIG. 15A, the weight loss analysis revealed that most of the electron mediators significantly promoted lignin depolymerization. As compared to the laccase only treatment control, essentially all electron mediators can increase the soluble fraction of kraft lignin in water (FIG. 15A).

Figure 15B:
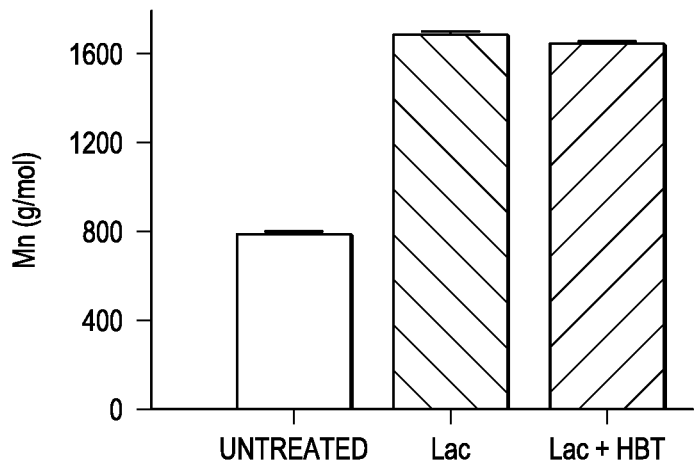
Figure 15C:
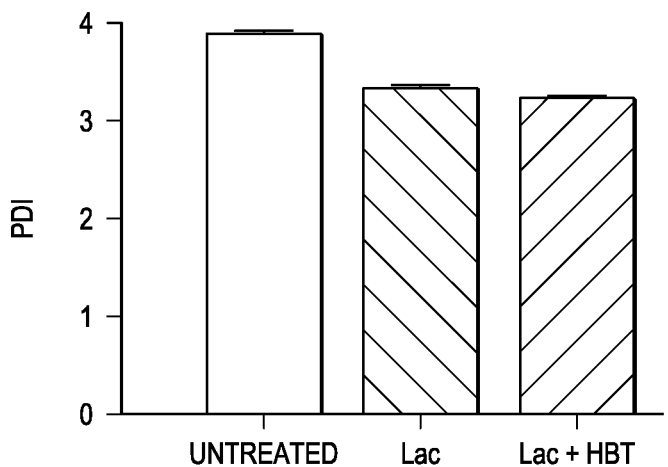

The efficiency for lignin depolymerization varies substantially among different mediators (FIG. 14). For example, the laccase-HBT (1-hydroxybenzotriazole) system could lead to the most efficient lignin depolymerization with more than 35% of the kraft lignin released into water. Only about 15%, 22% and 13% of lignin was solubilized, when ABTS (2,2'-azino-bis(3-ethylbenzothiazoline-6-sulphonic acid)), acetosyringone, and phenol were used as mediators, respectively. The data from weight loss analysis was further confirmed by Prussian Blue assay of total aromatic compounds solubilized (FIG. 15B). As shown in FIG. 15B, the HBT-laccase system led to the highest concentration of aromatic compounds in water. The GC/MS analysis was further carried out to analyze the soluble monomer compounds released after lignin depolymerization by different laccase-mediator systems (FIG. 15C). The GC/MS analysis revealed that laccase in combination with various mediators released different aromatic monomer compounds, indicating possible selective targeting of different chemical linkages during lignin oxidation.

Overall, the invention demonstrates that an efficient laccase-mediator system could substantially promote lignin fragmentation and solubilization. Various mediators have different efficiency and selectivity for facilitating the lignin depolymerization reactions. We therefore focused on the most efficient mediator, HBT, to study the chemical mechanisms for electron mediators to promote lignin degradation and to investigate the feasibility of coupling laccase-mediator-based lignin solubilization with microbial bioconversion.

Example 21

Figure 16A:
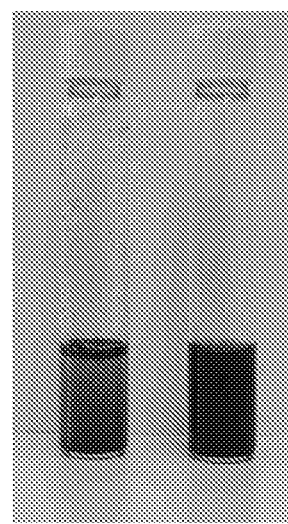
Figure 16B:
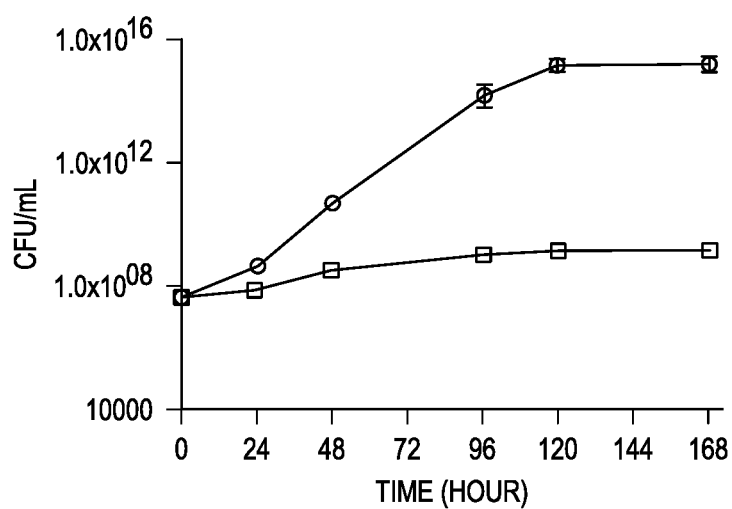

Lignin Depolymerization by an Efficient Laccase-Mediator System Increased the Molecular Weight of Insoluble Lignin and Promoted Degradation of Functional Groups In an effort to determine the effect of laccase-mediator system on the molecular weight distribution of kraft lignin, gel permeation chromatography (GPC) was employed to analyze the insoluble portion of lignin before and after the laccase-mediator treatment. There was a significant increase of molecular weights of insoluble lignin after the laccase and laccase-HBT treatment. $M_w$ of lignin increased from 3122 to 5595 and 5337 g/mol for laccase and laccase-HBT treatment, respectively. $M_n$ of lignin increased from 801 to 1678 and 1652 g/mol for laccase and laccase-HBT treatment, respectively. (FIG. 16A, 16B). GPC analysis also revealed the decrease of polydispersity index (PDI) in the insoluble fraction of the treated lignin (FIG. 16C), which could be attributed to the behavior of $M_n$ and $M_w$. PDI was obtained through dividing $M_w$ by $M_n$, and any changes on those two parameters could result in the altered PDI. The decreased PDI suggested that the insoluble lignin after laccase and mediator treatment became more uniform in molecular weight distribution.

Quantitative $^{31}P$ NMR technique was applied to monitor the changes of aliphatic, phenolic hydroxylic and carboxylic functional groups in kraft lignin. The $^{31}P$ NMR analysis of insoluble fraction of kraft lignin provided an accurate and quantitative way to illustrate the effects of laccase-HBT system on lignin chemical bonds cleavage. As shown in Table 6, the kraft lignin used in the study was mainly composed of guaiacyl (G) and p-hydroxyphenyl (H) units, as revealed by the presence of G and H spectra signal and the absence of syringyl (S) spectra signal. The $^{31}$P NMR revealed that laccase-HBT system treatment could lead to much more significantly decrease of non-condensed structures including guaiacyl, p-hydroxyphenyl and aliphatic OH structure by 42.1%, 45.5% and 26.1%, respectively, as compared to those of untreated lignin. The decrease of these functional groups by laccase alone treatment was much less significant, where only 27.9% decrease of guaiacyl group was observed, and no significant changes of p-hydroxyphenyl structure and aliphatic OH structure were found (Table 6). Moreover, the major interlinkages including β-5, 4-O-5 and 5-5 in kraft lignin were significantly decreased after laccase-HBT treatment by 45.3%, 29.7% and 32.2%, respectively. However, only 22.6% decrease of β-5 was observed in laccase alone treatment and no significant decrease of 4-O-5 and 5-5 linkages were observed (Table 6). Meanwhile, C5 condensed structure and carboxylic group in the insoluble lignin after laccase-HBT treatment were found significantly decreased as compared to those in untreated lignin and laccase-treated lignin. It should be noted that carboxylic group is one of the major hydrophilic groups in lignin. The significant decrease of carboxylic group in the insoluble lignin fraction after laccase-HBT treatment might result from the release of such group into the fragmented small molecular compounds soluble to water. All of these results strongly suggested that laccase-HBT could depolymerize lignin in a much higher efficiency than that of laccase alone treatment. The higher efficiency was achieved by significantly improved cleavage of the aromatic interlinkages to release aromatic monomers and/or oligomers into water. Taken together with the lignin solubilization data and GPC analysis of insoluble lignin, the results highlighted that electron mediators like HBT could facilitate the electron transfer for attacking the abundant chemical groups and linkages to significantly increase the solubilization of kraft lignin.

TABLE 6

Decrease of non-condensed structures observed in laccase treatment.

| Chemical shift range (ppm) | Assignment | Structure sample | Consistency (mmol/g) | | |
|---|---|---|---|---|---|
| | | | Untreated lignin | Lac | Lac + HBT |
| 150.0-145.5 | Aliphatic OH | | 2.57 | 2.33 | 1.90 |
| 144.70-142.92 | β-5 | | 0.53 | 0.41 | 0.29 |
| 142.92-141.70 | 4-O-5 | | 0.37 | 0.35 | 0.26 |
| 141.70-140.20 | 5-5 | | 0.59 | 0.51 | 0.40 |
| 140.20-138.81 | Guaiacyl | | 1.90 | 1.37 | 1.10 |
| 138.18-137.30 | p-hydroxylphenyl | | 0.22 | 0.21 | 0.12 |

TABLE 6-continued

Decrease of non-condensed structures observed in laccase treatment.

| Chemical shift range (ppm) | Assignment | Structure sample | Consistency (mmol/g) | | |
|---|---|---|---|---|---|
| | | | Untreated lignin | Lac | Lac + HBT |
| 136.60-133.60 | Carboxylic acid OH | (L-phenyl-COOH structure) | 0.46 | 0.32 | 0.14 |
| 144.7-140.0 | C5 substituted "condensed" | (condensed lignin structure) | 1.56 | 1.35 | 0.98 |

Example 22

Solubilized Lignin by the Laccase-HBT System Significantly Promoted Cell Growth and Lipid Yield During Bioconversion We further investigated if the solubilized lignin from laccase-mediator system can be used for bioconversion. Although recent technology breakthroughs have enabled several chemical/physical methods to pre-process lignin for efficient fractionation,[18-20] the combination of these methods with bioconversion leads to limited increase of bioproduct yield from lignin as compared to that from model compounds.[21] Considering the potentially less toxic compounds produced by enzymatic lignin fragmentation as compared to chemical fragmentation, we investigated the compatibility of this laccase-mediator system with microbial bioconversion. The soluble fraction of laccase-HBT depolymerized kraft lignin was used as fermentation substrate for an oleaginous bacteria R. opacus PD630. The results highlighted that the lignin depolymerization by the laccase-mediator treatment could significantly promote lignin consumption and enable a record level of bioproduct yield on lignin. When the solubilized lignin was used as the sole carbon source for R. opacus PD630 fermentation, cell growth increased by $10^6$ folds as compared to the cells grown on untreated kraft lignin (FIG. 17A). The lipid yield achieved 1.02 g/L, which was 10 time higher than the cells grown on untreated lignin. The GC/MS analysis of the aromatic monomer compounds in the medium before and after fermentation indicated the consumption of several major compounds including cinnamic acid, 4-hydroxybenzaldehyde, 4-hydroxybenzoic acid, phenol, vanillin, and others. In addition, several new aromatic compounds like 1,3-diacetylbenzene, octopamine and 1,4-cyclohexadiene were also found in the media after the fermentation. The results indicated that R. opacus PD630 not only utilized the aromatic monomers, but also degraded the aromatic oligomers to release monomers. Overall, the significant increases in lipid yield and cell growth indicated that the enzyme-mediator system for lignin fragmentation was very compatible with a variety of bioconversion platforms to process highly recalcitrant and insoluble lignin like kraft lignin.

Example 23

Laccase-HBT Treated Lignin can be Used to Improve Asphalt Binder and Carbon Fiber Quality The lignin derived from the Laccase-HBT treatment was broadly used for some new functions. First, we used the laccase-HBT treated lignin fractions to serve as asphalt binder to improve the asphalt performance. As shown in the FIG. 34, the treated lignin can be used as asphalt binder to increase the high temperature and low temperature performance. Basically, for the insoluble portion of Laccase-HBT treated lignin could significantly improve high temperature property and reduce low temperature cracking property of asphalt binder.

In addition, as shown in FIG. 37, the kraft lignin fiber with Laccase-HBT treatment has un-uniform diameters, and some knot-like defects (indicated by the red arrow). On the other side, the soluble fraction of laccase-HBT treated Kraft lignin fiber exhibited more uniform and thinner fibers (in nano diameter). The results indicated that without Laccase-HBT treatment, the lignin-PAN composite is easier to form aggregates, which will make it difficult to spin and make it challenging to produce high quality fiber.

The conventional carbon fiber is mainly made of PAN, whose cost closes to 60% of the total production cost. Lignin as a bio-renewable and cheap paper industry byproduct, has a carbon content as high as 60%, therefore it can be used as an alternative of PAN to reduce the carbon fiber production cost. However, lignin is a heterogeneous polymer composed of molecules with different molecular weight, several kinds of functional groups, and variable interunitary linkages. This intrinsic heterogeneity property largely hindered the conversion from lignin into high mechanical performance carbon fiber. There have several approaches to facilitate this conversion: 1) chemically modify lignin functional group (Maradura et al 2012, Xia et al 2016, Ding et 2016); 2) blend lignin with other polymers which acted as plasticizers (Kadla et al 2001); 3) find new lignin type with less heterogeneity (Dixon et al 2015). However, most of these carbon fibers are still too weak to commercialize. As we known, the best mechanical strength of lignin carbon fiber nowadays was made by blending with a high MW PAN at only 35% lignin loading and can close Toray T300 level PAN-based carbon fiber (Husman 2012). The problem is the percentage of the high cost PAN, as 65%, is still high. In our claim, we used a new method to modify lignin, namely laccase/HBT enzymatic treatment. The hydroxyl groups of lignin can be significantly reduced, and the molecular weight distribution of lignin was narrowed (Zhao et al 2016). Up-to-date, we can blend lignin with PAN at a 50% ratio to get lignin fiber (Figure . . . ), which means the cost of PAN precursor can be further decreased by using our treated lignin. Moreover, based on the modifications of function group and molecular weight distribution with the enzymatic treatment, this lignin derived nanofiber shows high potential in making high mechanical performance carbon fiber.

Example 24

R. opacus PD630 Promotes Lignin Depolymerization and Lipid Production

R. opacus PD630 was combined with laccase and different electron mediators to promote lignin depolymerization and lipid production to lead to higher lignin consumption and lipid yield. The laccase-HBT treatment depolymerized lignin better and thus promoted lignin utilization during the fermentation. The efficacy of different electron mediators is shown in FIG. 14. The pretreated lignin with laccase and electron mediator promoted lignin solubilization and lipid production (FIG. 15).

Example 25

R. opacus PD630 Engineered to Secrete Laccase to Lead to Higher Lignin Consumption and Lipid Yield To reach the goal of producing high levels of extracellular laccase for lignin depolymerization, an R. opacus PD630 strain was engineered for a laccase secretive expression system based on systemic design through optimizing the following four aspects: transcription/translation, signal peptide efficiency, membrane protein transporter capacity, and cultivation conditions (FIG. 16). Based on the genomic and secretomic analysis, most of the highly secreted proteins were found to have predicted signal peptides involving the twin-arginine translocation (Tat) system, which can transport structured protein and is thought to be the major protein transportation system in many gram-positive bacteria. Therefore, the Tat system was chosen as the target secretion system for laccase extracellular expression. Eighteen different predicted Tat system signal peptides were screened from a group of secreted proteins with relatively high expression levels based on secretomic analysis, among which the signal peptide S2587 led to the most efficient laccase secretion (FIG. 17). Next, the small laccase heterologous expression was optimized in R. opacus PD630 by integrating different promoters/ribosomal binding sites (RBS) with 52587 (FIG. 18). The promoters/RBSs selected were among three constitutive expressed proteins representing three different expression levels in R. opacus PD630 based on proteomics. Under these promoters/RBSs, laccase could be constantly expressed to display extracellular laccase activity, which was needed to continually depolymerize lignin and release carbon for the microbe.

Heterologous expression of secretable laccase at high levels may lead to overloading of the protein membrane transporters, which results in low efficiency of laccase secretion. In addition, the inefficient extracellular transportation of laccase from the cytoplasm may also cause degradation of laccase that is not secreted, which will in turn result in microbial energy and carbon source wastage. Therefore, the transportation capacity of the Tat system was further optimized in R. opacus PD630 by overexpression of the key components of the Tat system, TatA and TatC (FIG. 19). The TatA and TatC genes were integrated into the same operon with laccase. The overexpression of TatAC with their native RBSs increased extracellular laccase activity by over 60% compared to that without overexpression of TatAC grown in glucose (FIG. 19). The transportation capacity of Tat system was further increased by overexpressing TatA and TatC with two stronger RBSs, R704 (the RBS from gene OPAG_00704) and R756 (the RBS from gene OPAG_07756), respectively, resulting in an almost two-fold increase of extracellular laccase activity (12.32 U/mL) compared to that without overexpression of TatAC (6.21 U/mL) grown in glucose (FIG. 17D).

Considering the high activity of this small laccase to broad substrates, it was thought that high levels of heterologous expression of the laccase in R. opacus PD630 may cause a toxicity response in the cell, which would decrease laccase production. To overcome this barrier, laccase was first produced in apoprotein form by cultivating the engineered strain in non-copper medium. Without integrating with copper ions, the apoprotein has no laccase activity and thus it has no toxicity to the cell. In this way, the engineered strain could produce 5-fold higher extracellular total protein than the wild type strain (FIG. 20). The apoprotein could be refolded to recover its laccase activity by recruiting copper ions to its active sites when incubated with copper. This cultivation method would result in the strain having a very stable laccase production capacity, even after several batches of cultivation. More importantly, this method could also result in an extracellular laccase activity reaching 75 U/mL after 4 days of growth in glucose, which is 7-fold higher than when directly cultured in medium with copper (FIG. 21).

Example 26

Engineering a FASI Synthase Increases Lipid Production

Most of the aromatic compounds released from lignin after depolymerization will be metabolized to acetyl-CoA, which could either be used as substrates for citrate cycle pathway or fatty acid synthesis pathway. To increase the efficiency of lipid production from lignin, we optimized the triacylglycerols (TAG) synthesis pathway to drive more carbon flux into fatty acid synthesis pathway. Based on our comparative proteomics analysis, we found two of the genes, fasI (fatty acid synthase I) and atf2 which showed bifunctional wax ester synthase/acyl-CoA:diacylglycerol acyltransferase (WS/DGAT) activity, were significantly overexpression under high lipid production condition (FIG. 16A). Fatty acid synthase I in R. opacus PD630 is a highly integrated multienzyme, which contains seven functional domains, could catalyze all the fatty acid synthesis initiation and elongation reactions by coordinating with phosphopantotheinyl transferase (PTT) which was expressed in the same operon with fasI[20, 28, 29]. WS/DGAT encoded by atf2 catalyzes the final step in biosynthesis of TAG which is the main storage form of lipid.

Based on these analyses, we believed that overexpression of a fasI operon and atf2 would drive more carbon flux into lipid biosynthesis by recruiting more acetyl-CoA into fatty acid synthesis pathway instead of citrate cycle. We proved this hypothesis by overexpression both fasI operon and atf2 in R. opacus PD630 (PD630_FA) with a benzoate-inducible promoter from Rhodococcus RHA1 as described by previous publication[30]. We first evaluated the lipid production ability of this engineered strain PD630_FA from glucose which could also be catabolized into acetyl-CoA for both citrate cycle and fatty acid synthesis pathway. PD630_FA performed significant better in lipid accumulation from glucose compared to wild type strain under test conditions (FIG. 16B). For example, PD630_FA made a total lipid yield to 2.916 g/L and lipid content to 54.76% after 4-days cultivation in glucose, while wild type strain only reached 0.915 g/L and 21.03%, respectively. However, it didn't significantly change the cell biomass yield.

Figure 16C:
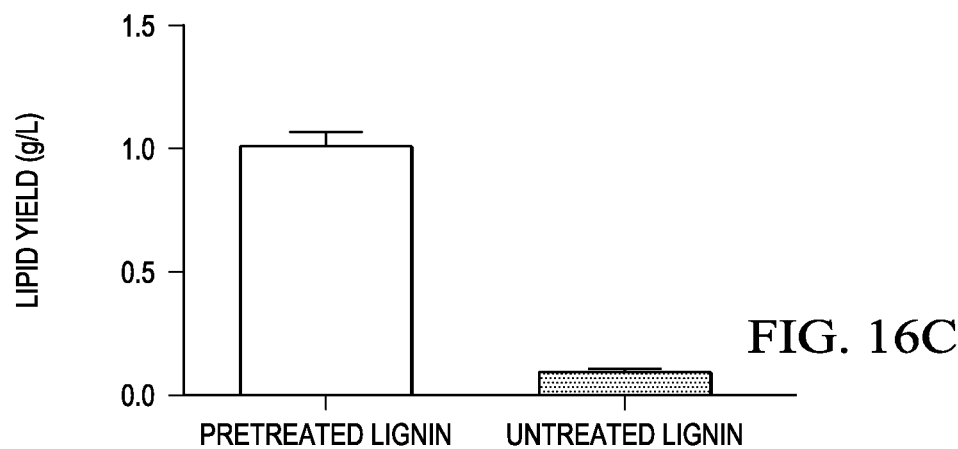

After we equipped R. opacus PD630 with the highly laccase secretive system, we evaluated the performance of this engineered strain (PD630_LT) for lignin depolymerization. To make sure PD630_LT could maintain its original laccase production capacity before inoculating for lignin fermentation, the seed culture was prepared by cultivating PD630_LT in 0.5% glucose medium without copper for 4 days after all the glucose was consumed. Considering the laccase present in seed culture could be used for initial lignin depolymerization, we inoculated the bacterial as well as its culture supernatant into lignin medium for fermentation. As proven by our previous study, the presence of the right mediator could significantly improve the efficiency of lignin depolymerization by laccase. Here we chose acetosyringone as the redox mediator for the small laccase. After 7 days of fermentation in lignin medium, the CFU of PD630_LT was approximately 1000-fold higher than the control strain (FIG. 16C). All these results clearly highlighted that secreted laccase system could significantly improve lignin depolymerization and lignin conversion efficient in R. opacus PD630.

Example 27

R. opacus PD630 Engineered to Produce a Broad Range of Enzymes and Proteins of Value The aforementioned the optimized secretion expression system included a signal peptide, a strong promoter and RBS, a target protein, and an over-expressed tat system. The system can be used to produce a variety of proteins and enzymes as shown in FIGS. 30, 31, 32 and 33. As shown in FIG. 30, the heterologous expression of a termite endogluconanse in Rhodococcus opacus PD630 with the aforementation engineered secretive system can lead the to a high expression activity. In the same way, the heterologous expression of cattle rumen endogluconanse, cellobiohydrolase and xylanase from different symbiotic bacteria in rumen using the engineered secretive expression system led to high enzyme activity and productivity. In addition, the same engineered secretive expression system has been exploited to produce a xylanase enzyme from filamentous fungus Trichoderma reesei in Rhodococcus and achieved high activity and productivity. Moreover, the same engineered expression system has been used to heterologously express an anticancer peptide lunasin in Rhodococcus opacus PD630 with high productivity and activity. An effective secretive expression system in gram positive bacteria is not trivial. It is both novel and highly transformative because of broad applications.

Example 28

Conversion of Lignin into Lipid

Lignin could be pretreated by laccase to release aromatic compounds. Rhodococci could use the pretreated lignin as carbon source to produce lipid (FIG. 22). At the other end, Rhodococci engineered with laccase also could consolidate converse lignin as growth carbon source for lipid production (FIG. 23). To increase the lipid yield, the strain could be optimized to its triacylglycerols (TAG) synthesis pathway to drive more carbon flux into fatty acid synthesis pathway (FIG. 24). The overexpression of genes FAS (fatty acid synthase) and atf (bifunctional wax ester synthase/acyl-CoA:diacylglycerol acyltransferase) could significantly increase its lipid yield (FIG. 25).

Example 29

Bio-Pretreatment of Lignocellulose Biomass for Efficient Saccharification

The Rhodococci engineered with lignin degradation-related enzymes were used for pretreatment of lignocellulose biomass. Rhodococci could degrade lignin to decrease its recalcitrance to enzymatic saccharification, and use part of degraded lignin as carbon source for growth and leave most of the sugar. Different lignin degradation enzymes including but are not restrict to laccase, lignin peroxidase, manganese peroxidase, versatile peroxidase, DyP-type peroxidase and cellobiose dehydrogenase. These lignin degradation enzymes could be heterologous expressed in Rhodococci according aforementioned genetic engineering system. To drive the strain to use degraded lignin as carbon resource but not sugar, the strain was further mutated to disrupt its sugar transporter.

The invention claimed is:

1. A method of lignin fractionation comprising contacting a sample of biomass comprising lignin with 1) at least one bacterium that secretes a lignin degradation enzyme, and 2) at least one electron mediator or a chemical selected from the group consisting of iron ions, hydrogen peroxide and formic acid, wherein the result of said contacting is said lignin is depolymerized, wherein said lignin degradation enzyme is a peroxidase or a laccase from a bacterial species different than the at least one bacterium, wherein the at least one bacterium is a *Rhodococcus* or a *Pseudomonas* bacterium, and wherein the resulting depolymerized lignin is processed to separate the depolymerized lignin into different fractions.

2. The method of claim 1, wherein the peroxidase is selected from the group consisting of a dye-decolorizing peroxidase, a lignin peroxidase, a manganese peroxidase, and a versatile peroxidase.

3. The method of claim 1, wherein the at least one electron mediator is selected from the group consisting of 1-hydroxy-benzotriazole (HBT), 2,2'-azino-bis-(3-ethylbenzothiazoline-6-sulfonic acid) (ABTS), acetosyringone, phenol, and violuric acid.

4. The method of claim 1, wherein the at least one bacterium is *Rhodococcus opacus* PD630 or *Pseudomonas putida* A514.

5. The method of claim 1, wherein said depolymerized lignin has undergone fermentation.

6. The method of claim 1, wherein the different fractions comprise a soluble fraction and an insoluble fraction, and the soluble fraction is mixed with an asphalt binder.

7. The method of claim 5, wherein the fermentation uses a bacterium selected from the group consisting of *Rhodococcus* and *Pseudomonas*.

8. The method of claim 1, wherein a fraction of the depolymerized lignin is processed to produce a bioplastic.

* * * * *